(12) United States Patent
Karayiorgou et al.

(10) Patent No.: US 6,395,482 B1
(45) Date of Patent: May 28, 2002

(54) METHOD OF DETERMINING SUSCEPTIBILITY TO SCHIZOPHRENIA

(75) Inventors: Maria Karayiorgou; Joseph A. Gogos, both of New York, NY (US)

(73) Assignee: The Rockfeller University, New York, NY (US)

( * ) Notice: Subject to any disclaimer, the term of this patent is extended or adjusted under 35 U.S.C. 154(b) by 0 days.

(21) Appl. No.: 09/277,262

(22) Filed: Mar. 26, 1999

Related U.S. Application Data

(63) Continuation-in-part of application No. 09/229,530, filed on Jan. 13, 1999, now abandoned.

(51) Int. Cl.[7] .................... C12Q 1/68; C12P 19/34; C07H 21/04
(52) U.S. Cl. .................... 435/6; 435/7.1; 435/91.2; 536/23.5; 536/24.31; 536/24.33
(58) Field of Search .................... 536/23.1, 23.5, 536/24.31, 24.33; 435/325, 69.1, 6, 7.1, 91.2

(56) References Cited

U.S. PATENT DOCUMENTS 5,542,601 A    8/1996   Fallon et al.

OTHER PUBLICATIONS

M. Karayiorgou et al., Molecular Psychiatry, "Dissecting the genetic complexity of schizophrenia," Feb. 1997, 2, pp. 211–223.*
H. D. Campbell et al., Hum Genet, "Human homologue of the *Drosophila melanogaste* sluggish–A(proline oxidase) gene maps to 22q11.2, and is a candidate gene for type–I hyperprolinaemia," (1997)101:69–74.*
D. C. Haywaard et al., Neurobiology, GenBank data base (accession no L07330), Proc. Natl. Acad. Sci. USA, Apr. 1993, vol. 90, 2979–2983.*
R. Berry et al., Nature Genet, Accession No. T16832, Jul. 1996.*
H. D. Campbell et al., Gen Bank, Accession No. U 82381.*
D. C. Hayward et al., Gen Bank, Accession No. L07330.*

* cited by examiner

Primary Examiner—Deborah Crouch
Assistant Examiner—Joseph T. Woitach
(74) Attorney, Agent, or Firm—Klauber & Jackson

(57) ABSTRACT

Variations in the DNA sequence of the human proline dehydrogenase gene (PRODH) which correlate to an increased susceptibility to, or presence of schizophrenia or a disease or disorder related thereto, such as obsessive compulsive disorder (OCD), bipolar disorder (BP), or major depressive disorder (MDD) are provided, along with assays to diagnosing schizophrenia or a disease or disorder related thereto, and evaluating potential drugs or agents for using in treating such diseases or disorders.

1 Claim, 16 Drawing Sheets

FIG. 1A

```
                                                                                                                    H. sapiens
                                                                                                                    M. musculus
  1   ------------------------------------------------------------                                                  D. melanogaster
  1   MALLRSLSAQRTAISLVYGRNSSKSSNSVAVAACRSFHQRGNGSTSIAGEGAASESTRGVNGARFLHSGDRPLQASTLVQPEVVSSETVKRSMKQESSQE            S. cerevisiae 1   ------------------------------------------------------------MLEFVMREWKKSRKLLGQRLFNKLMKMTFYGHFVAGEDQESIQPLLRHYRAFG  H. sapiens
  1   ------------------------------------------------------------MFERIMKMTFYGHFVAGEDQESIRPLIRHNKAFG                    M. musculus
101   KNPSPAGSPQRDPLDVSFNDPIAAFKSKTTGELIRAYLVVMICSSENLVEHNMTLMKWSKNVLGQRLFTLLMKATFYGHFVAGEDQIKIIPTLERLRSFG              D. melanogaster
  1   ------------------------------------------------------------MIASKSSLLVTKSRIPSLCFPLIKRSYVS                        S. cerevisiae 54   VSAILDYGVEEDLSPEEAEHKEMESC-TSAAERDGSGTNKRDKQYQAHRAFGDRRNGVISARTYFYANEAKCDSHMETFLRCIEA-SGRVSDDGFIAIKL              H. sapiens
 35   VGFILDYGVEEDLSPEEAERKEMESC-TSEAERDGSGANKREKQYQVHPAFGDRRDGVISARTYFYANEAKCDNYMENLLQCIKA-SGGASDGFSAIKL              M. musculus
201   VKPILDYSVEEDITQEEAEKREVESSVSSAGDKKEEGSM---PQYHVDKSFADRRYKVSSARTYFYLNEATCERNMEIFIKCLEAVSGATFGTGITAIKL             D. melanogaster
 30   KTPTHSNTAANLMVETPAANPNGNSVMAPPNSINFLQTLPKKELFQLG-FIGIATLNSFFLNTIIKLFPYIPIPVIKFFVSSLYCGGENFKEVIECGKRL             S. cerevisiae 152   TALGRPQFTLQFSEVLAKWRCFFHQMAVEQGQAGLAAMDTKLEVAVLQESVAKLGIASRAEIEDWFTAETLGVSGTMDLLDWSSLIDSRTKLSKHLVVP-             H. sapiens
133   TALGRPQFTLQFSDVLTRWRFFHQMAAEQGQAGRAAVDTKLEVAVLQDSIAKMGIASRAEIEGWFTEPTLGVSGTVDLLDWNSLIDSRTRLSRHLVVP-             M. musculus
298   TALGRPQLLLQLSEVIMRTRKYMEDMVGGQGN---VLTHHKTIDLEKYYATLG-DNKDVKEFLNNVTSDKEGILHLFPWSGIVDEDSQLSDTFRVP-               D. melanogaster
129   QKRGISNMML--------------SLTIENSEGTKSLSSTPVDQIVKETISSVHNILLPNIIGQLESKPITDIAPGYIALKPSALVDNPHEVLYNFSNPA             S. cerevisiae 251   -NAQTGQLEPLLSRFTEEEELQMTRMLQRMDVLAKKRATEMGVRLMV----DAEQTYFQPAISRLTLEMQRKFNVEKPL----IFNNTYQCYLKDAYDNVTLD           H. sapiens
232   -NVQTGQLEPLLSRFTEEEEQQMKRMLQRMDVLAKKAKEAGVRLMI----DAEQSYFQPAISRLTLEMQRRFNVDKPF----IFNNTFQCYLKDAYDNVTLD           M. musculus
391   -DPQTGQMRRLISQIPPKEEMFRNMIRRLNTIVKRAADLLDVRIMV----DAEQTYFQPAISRITLEMVRKYNKDKAI----VFNNTYQCYLRETFREVNTD           D. melanogaster
215   YKAQRDQLIENCSKITKE-------IFELNQSLLKKYPERKAPFMVSTIDAEKYDLQENGVYELQRIIFQKFNPTSSKLISCVGTMQLYLRDSGDHILHE              S. cerevisiae 343   VELARREGWCFGAKLVRGAYLAQERARAAEIGYEDPINPTYEATNAMYHRCLDYVLEELK--------HNAKAKVMVASHNEDTVRFALRRMEELGLHPAD             H. sapiens
324   MELARREGWCSGAKLVRGAYLVRRAYMAQERVRAAEIGYEDPINPTYEATNAMYHRCLNYVLEELK--------HSTKAEVMVASHNEDTVHFTLCRMKEIGLHPAD       M. musculus
483   LEQAKRQNFYFGAKLVRGAYMDQERDRAKSLGYPDPVNPTFEATTDMYHRTLSECLRRIKLMKDCDDDARKIGIMVASHNEDTVRFAIQQMKEIGISPED             D. melanogaster
308   LKLAQENGYKLGLKLVRGAYIHSEKNRNQII-FGDK------TGTDENYDRIITQVVNDLI---INGEDSYFGHLVVASHNYQSQMLVTNLLKSTQDNSYA             S. cerevisiae 436   HQV-YFGQLLGMCDQISFPLGQAGY--PVYKYVPYGPVMEVLPYLSRRALENSSLMKGTHREROLLWLELLRRLRTGNLFHRPA                              H. sapiens
417   GQV-CFGQLLGMCDQISFPLGQAGF--PVYKYVPYGPVMEVLPYLSRRALENSSIMKGAQREROLLWQELRRRLRTGSLFHHPA                              M. musculus
583   K-VICFGQLLGMCDYITFPLGQAGY--SAYKYIPYGPVEEVLPYLPYLSRRAQENKGVLKKIKKEKRLLSEIRRRLMRGQLFYKPKGNYVPI                     D. melanogaster
399   KSNIVLGQLLGMADNVTYDLITNHGAKNIIKYVPWGPPLETKDYLLRRLQENGDAVRSDN-GWPLIKAIAKSIPKRVGL                                  S. cerevisiae
```

FIG. 6

```
ATGCTGGAATTTGTGATGAGAGAGTGGAAAAAATCCAGGAAACTTCTAGGACAGAGGCTATTCAACAAGCTCATGAAGATGACCTTCTATGGGCATTTTG  100
TAGCCGGGGAGGACCAGGAGTCCATCCAGCCCCCTGCTTCGCACTACAGGGCCTTCGGTGTCAGCGCCATCCTGGACTATGAGTGGAGGAGGACCTGAG  200
CCCCGAGGAGGCAGAGCACAAGAGATGGAGTCCTGCACCTCAGCTGCGAGAGGATGGCAGTGGACAAGCGGGACAAGGAATAAGCGGGACAATACCAGCCCAC  300
CGGGCCTTCGGGGACCGCAGGAGTAGAGTCAGCGATGACGGCTTCATAGACCCGCCCACCTACTTCTACGCCAAGTGCCGACAGCCACATGGAGACATTCTTGCGCT  400
GCATCGAAGCCTCAGTAGAGTCAGCGATGACGGCTTCATGACGGCTTCATAGACCCGCCCACCTACTTCTACGCCAAGTGCCGACAGCCACATGGAGACATTCTTGCGCT  400
GGCCAAGTGGAGGTGCTTCTTTCACCAAATGGCTGTGAGATTGAGGACTGGTTCCCCAAGCACCTGTCTCCCAAGCAACCCCTGGAGTGTCTGGCACCATGGAGGTGCGGTGCTGCTGGACTGA  700
AGTGTCGCAAAGTTGGGCATCGACAGAGGACCAGGACACAGAGCTGTCCAAGCTGTCCAAGCACCTGTCTCCCAAGCAACCCCTGGAGTGTCTGGCACCATGGAGGTGCGGTGCTGCTGGACTGA  700
GCAGCCCTCATCGACACAGCAGGACTACAGCGACGCTGGAGATGCAGCGGAAGTTCAATGTGGAAGAAGCCGCTCATCTTCAACACATACCAGTGCTACCTCAAGG  1000
GGAGGAGCTACAGCCAGGACTACAGCGACGCTGGAGATGCAGCGGAAGTTCAATGTGGAAGAAGCCGCTCATCTTCAACACATACCAGTGCTACCTCAAGG  1000
TACTTCCAGCCCAGCCCATCAGCCGACCCTGGACGTGGAGCTCGCCGTGGAGCGTGGTGTTTGGGGCGACTGGTGTTTGGGGCGCATACCTGGCCCAGGAGCG  1100
ATGCCTATGACAAATGTGACCCTGGACGTGGAGCTCGCCGTGGAGCGTGGTGTTTGGGGCGACTGGTGTTTGGGGCGCATACCTGGCCCAGGAGCG  1100
AGCCCGTGCGCAGAGATCGGCTATGAGGACCCCATCAACCCACGTACGAGGCCATGTGCCTGGACACGTACCTGTGTTGGAGAG  1200
CTGAAGCACAACGCCAAGGCCAAGTGATGGTGGCCTCGTAGGACAGCTGCTAGGACATGTGTGACCAGATGTGACCAGATGTGACCCCGTGTACAAGTACGTGCCCTA  1400
CTGACCACCAGGTGTACTTTGGACAGCTGCTGCCCTACTTGTCCCGCCGTGACCCAGATGTGACCAGATGTGACCCCGTGTACAAGTACGTGCCCTA  1400
TGGCCCCCGTGATGGAGGTGCTGCCCTACTTGTCCCGCCGTGACCAGATGTGACCAGATGTGACCCCGTGTACAAGTACGTGCCCTA  1400
GAGCTCTTGAGGCGGCTCCGAACTGGCAACCTCTTCCATCGCCCTGCCTAG  1551
```

FIG. 7

| | |
|---|---|
| MLEFVMREWKKSRKLLGQRLFNKLMKMTFYGHFVAGEDQESIQPLLRHYR | 50 |
| AFGVSAILDYGVEEDLSPEEAEHKEMESCTSAAERDGSGTNKRDKQYQAH | 100 |
| RAFGDRRNGVISARTYFYANEAKCDSHMETFLRCIEASGRVSDDGFIAIK | 150 |
| LTALGRPQFLLQFSEVLAKWRCFFHQMAVEQGQAGLAAMDTKLEVAVLQE | 200 |
| SVAKLGIASRAEIEDWFTAETLGVSGTMDLLDWSSLIDSRTKLSKHLVVP | 250 |
| NAQTGQLEPLLSRFTEEEELQMTRMLQRMDVLAKKATEMGVRLMVDAEQT | 300 |
| YFQPAISRLTLEMQRKFNVEKPLIFNTYQCYLKDAYDNVTLDVELARREG | 350 |
| WCFGAKLVRGAYLAQERARAAEIGYEDPINPTYEATNAMYHRCLDYVLEE | 400 |
| LKHNAKAKVMVASHNEDTVRFALRRMEELGLHPADHQVYFGQLLGMCDQI | 450 |
| SFPLGQAGYPVYKYVPYGPVMEVLPYLSRRALENSSLMKGTHRERQLLWL | 500 |
| ELLRRLRTGNLFHRPA | 517 |

FIG. 8

```
ATGTTCGAGAGATTGATGAAGATGACCTTCTATGGCCATT    40
TTGTGGCTGGCGAAGACCAGGAGTCTATCAGGCCTCTGAT    80
CCGGCACAACAAAGCCTTTGGTGTTGGCTTTATCCTGGAC   120
TATGGAGTGGAGGAAGATCTGAGCCCTGAGGAGGCGGAGC   160
GCAAAGAGATGGAGTCATGCACTTCTGAAGCAGAGAGAGA   200
TGGCAGTGGAGCAAATAAGAGGGAGAAGCAGTATCAGGTG   240
CACCCCGCCTTTGGAGACCGCAGAGATGGTGTCATCAGTG   280
CCCGCACCTACTTCTATGCCAATGAAGCCAAGTGTGACAA   320
CTACATGGAGAACTTACTGCAGTGCATCAAGGCCTCAGGT   360
GGAGCCAGTGATGGTGGTTTCTCAGCCATTAAGCTCACTG   400
CACTGGGGAGACCACAGTTTCTGCTGCAGTTCTCAGACGT   440
GCTGACCAGGTGGAGACGGTTCTTCCATCAAATGGCTGCA   480
GAGCAGGGACAGGCTGGGCGTGCTGCTGTAGACACAAAGC   520
TGGAGGTGGCGGTGCTCCAGGACAGCATCGCAAAGATGGG   560
CATCGCATCCAGGGCTGAGATTGAAGGGTGGTTCACGCCA   600
GAGACGCTGGGAGTGTCTGGCACCGTGGACTTGCTGGACT   640
GGAACAGCCTCATTGACAGCAGGACCCGGCTCTCCAGGCA   680
CTTGGTGGTCCCCAATGTGCAGACTGGCCAGCTGGAGCCC   720
CTGCTGTCACGGTTCACTGAGGAGGAAGAGCAGCAGATGA   760
AAAGGATGCTGCAGAGGATGGATGTACTGGCCAAGAAAGC   800
AAAAGAAGCAGGTGTGCGCCTGATGATTGATGCTGAGCAG   840
AGCTACTTCCAACCAGCCATCAGCCGCCTGACCCTGGAGA   880
TGCAGCGCAGGTTCAATGTGGATAAGCCGTTCATCTTCAA   920
CACATTCCAGTGCTACCTCAAGGATGCCTATGACAATGTG   960
ACCTTGGATATGGAACTGGCTCGCCGTGAGGGCTGGTGTT  1000
CCGGGGCCAAGCTGGTACGTCGTGCATACATGGCCCAAGA  1040
GCGTGTCAGGGCAGCAGAGATCGGTTATGAAGACCCCATC  1080
AACCCTACATATGAAGCCACCAATGCTATGTACCACAGGT  1120
GCCTTAACTATGTTCTGGAGGAGCTGAAGCACAGCACCAA  1160
GGCAGAAGTGATGGTGGCTTCCACAACGAGGACACCGTG  1200
CACTTCACKTTGTGCAGGATGAAGGAGATAGGCCTGCATC  1240
CTGCTGATGGTCAGGTGTGCTTCGGACAGCTGCTGGGGAT  1280
GTGTGACCAAATCAGCTTCCACTAGGCCAGGCAGGCTTT   1320
CCTGTGTACAAGTATGTGCCCTATGGCCCTGTGATGGAGG  1360
TACTCCCTTACCTGTCCCGCCGTGCCCTGGAGAACAGCAG  1400
CATCATGAAGGGTGCTCAGCGAGAGAGGCAGCTGCTATGG  1440
CAGGAGCTCCGCAGGCGGCTGCGCACTGGCAGCCTCTTCC  1480
ACCATCCGGCCTAG  1494
```

FIG. 9

| | |
|---|---|
| MFERLMKMTFYGHFVAGEDQESIRPLIRHNKAFGVGFILD | 40 |
| YGVEEDLSPEEAERKEMESCTSEAERDGSGANKREKQYQV | 80 |
| HPAFGDRRDGVISARTYFYANEAKCDNYMENLLQCIKASG | 120 |
| GASDGGFSAIKLTALGRPQFLLQFSDVLTRWRRFFHQMAA | 160 |
| EQGQAGRAAVDTKLEVAVLQDSIAKMGIASRAEIEGWFTP | 200 |
| ETLGVSGTVDLLDWNSLIDSRTRLSRHLVVPNVQTGQLEP | 240 |
| LLSRFTEEEEQQMKRMLQRMDVLAKKAKEAGVRLMIDAEQ | 280 |
| SYFQPAISRLTLEMQRRFNVDKPFIFNTFQCYLKDAYDNV | 320 |
| TLDMELARREGWCSGAKLVRRAYMAQERVRAAEIGYEDPI | 360 |
| NPTYEATNAMYHRCLNYVLEELKHSTKAEVMVASHNEDTV | 400 |
| HFTLCRMKEIGLHPADGQVCFGQLLGMCDQISFPLGQAGF | 440 |
| PVYKYVPYGPVMEVLPYLSRRALENSSIMKGAQRERQLLW | 480 |
| QELRRRLRTGSLFHHPA | 498 |

FIG. 10A

```
AGCGCGTCTTCTTGCTGCGGTCGGTGGCACCACGCGTCGC   40
TGCCCTCTCAACCAAACCGCAAGCCCAGGAACAGCCTCCC   80
GCGAGCCCTGAGGCTCTTCGGGGATGTGGGGCGGCCAAGG  120
CTGTGCGGCCGCCTGTGCCAGCCGTGGACTTCACCAACAC  160
GCAGGAGGCGTATCGCAGCCGGCGGAGTTGGGAGTTGGTG  200
CGCAACCTGCTAGTGCTGCGGCTGTGTGCGTCGCCGGTGC  240
TGCTAGCGCACCACGAGCAGTTGTTCCAAGTTGCCAGGAA  280
GCTTCTGGGGCAAAGGATGTTCGAGAGATTGATGAAGATG  320
ACCTTCTATGGCCATTTTGTGGCTGGCGAAGACCAGGAGT  360
CTATCAGGCCTCTGATCCGGCACAACAAAGCCTTTGGTGT  400
TGGCTTTATCCTGGACTATGGAGTGGAGGAAGATCTGAGC  440
CCTGAGGAGGCGGAGCGCAAAGAGATGGAGTCATGCACTT  480
CTGAAGCAGAGAGAGATGGCAGTGGAGCAAATAAGAGGGA  520
GAAGCAGTATCAGGTGCACCCCGCCTTTGGAGACCGCAGA  560
GATGGTGTCATCAGTGCCCGCACCTACTTCTATGCCAATG  600
AAGCCAAGTGTGACAACTACATGGAGAACTTACTGCAGTG  640
CATCAAGGCCTCAGGTGGAGCCAGTGATGGTGGTTTCTCA  680
GCCATTAAGCTCACTGCACTGGGGAGACCACAGTTTCTGC  720
TGCAGTTCTCAGACGTGCTGACCAGGTGGAGACGGTTCTT  760
CCATCAAATGGCTGCAGAGCAGGGACAGGCTGGGCGTGCT  800
GCTGTAGACACAAAGCTGGAGGTGGCGGTGCTCCAGGACA  840
GCATCGCAAAGATGGGCATCGCATCCAGGGCTGAGATTGA  880
AGGGTGGTTCACGCCAGAGACGCTGGGAGTGTCTGGCACC  920
GTGGACTTGCTGGACTGGAACAGCCTCATTGACAGCAGGA  960
CCCGGCTCTCCAGGCACTTGGTGGTCCCCAATGTGCAGAC 1000
TGGCCAGCTGGAGCCCCTGCTGTCACGGTTCACTGAGGAG 1040
GAAGAGCAGCAGATGAAAAGGATGCTGCAGAGGATGGATG 1080
TACTGGCCAAGAAAGCAAAGAAGCAGGTGTGCGCCTGAT  1120
GATTGATGCTGAGCAGAGCTACTTCCAACCAGCCATCAGC 1160
CGCCTGACCCTGGAGATGCAGCGCAGGTTCAATGTGGATA 1200
AGCCGTTCATCTTCAACACATTCCAGTGCTACCTCAAGGA 1240
TGCCTATGACAATGTGACCTTGGATATGGAACTGGCTCGC 1280
CGTGAGGGCTGGTGTTCCGGGGCCAAGCTGGTACGTCGTG 1320
CATACATGGCCCAAGAGCGTGTCAGGGCAGCAGAGATCGG 1360
TTATGAAGACCCCATCAACCCTACATATGAAGCCACCAAT 1400
GCTATGTACCACAGGTGCCTTAACTATGTTCTGGAGGAGC 1440
TGAAGCACAGCACCAAGGCAGAAGTGATGGTGGCTTCCCA 1480
CAACGAGGACACCGTGCACTTCACKTTGTGCAGGATGAAG 1520
GAGATAGGCCTGCATCCTGCTGATGGTCAGGTGTGCTTCG 1560
GACAGCTGCTGGGGATGTGTGACCAAATCAGCTTCCCACT 1600
AGGCCAGGCAGGCTTTCCTGTGTACAAGTATGTGCCCTAT 1640
GGCCCTGTGATGTAGGTACTCCCTTACCTGTCCCGCCGTG 1680
CCCTGGAGAACAGCAGCATCATGAAGGGTGCTCAGCGAGA 1720
GAGGCAGCTGCTATGGCAGGAGCTCCGCAGGCGGCTGCGC 1760
```

FIG. 10B

```
ACTGGCAGCCTCTTCCACCATCCGGCCTAGTCACCGCAGG 1800
AGCCTTGCCCACCCGCTCGTACTCCACTCAACCCCTTACC 1840
TCTGGGGCTTCAGGCGGGGCACAGCTTGGGATTGGGCTGG 1880
GGTTCCTTAACCCAACCTGCCCAGACACAGTTCACCTTTT 1920
TATGCCCAAGGCTTTTTATGCCCAAGGCGGGATTTCATCA 1960
GTGGACAGTTCCTGAGGAACAGTGCCCAAGATGGTCGTCT 2000
GGTCACAGAGGCTGCCTTCTGGGACTTCCTGTACCCCAAG 2040
GAACAGACACTCAGGAGTGGGGTCAGTTAGAGCCCTGGG 2080
AGCTGCCCCACTAATTTGAGTAAGCACTGACCACTTCTGC 2120
AGGTTACAGAGCCCTAGTCCAGGATTAACCTTCTGCCAGG 2160
GTCTAACCCATTTTCCCTGCACTGGGCAGAGGACAGACTA 2200
GGAAGCCTGTTTAGTCAATAAATCATCCTGTAACAGAGTC 2240
```

FIG. 11

```
MFERLMKMTFYGHFVAGEDQESIRPLIRHNKAFGVGFILD  40
YGVEEDLSPEEAERKEMESCTSEAERDGSGANKREKQYQV  80
HPAFGDRRDGVISARTYFYANEAKCDNYMENLLQCIKASG 120
GASDGGFSAIKLTALGRPQFLLQFSDVLTRWRRFFHQMAA 160
EQGQAGRAAVDTKLEVAVLQDSIAKMGIASRAEIEGWFTP 200
ETLGVSGTVDLLDWNSLIDSRTRLSRHLVVPNVQTGQLEP 240
LLSRFTEEEEQQMKRMLQRMDVLAKKAKEAGVRLMIDAEQ 280
SYFQPAISRLTLEMQRRFNVDKPFIFNTFQCYLKDAYDNV 320
TLDMELARREGWCSGAKLVRRAYMAQERVRAAEIGYEDPI 360
NPTYEATNAMYHRCLNYVLEELKHSTKAEVMVASHNEDTV 400
HFTLCRMKEIGLHPADGQVCFGQLLGMCDQISFPLGQAGF 440
PVYKYVPYGPVM 452
```

FIG. 12A

```
TAATGAGAGGGAAAACAAGTATGAAGCTGTGTGGCTGAAA  40
CCGTCTTGGCAAGTTAGGGAAAGAAAACGGAAGTCACTGG  80
GGCTGATCACAGTGCTAAGCATGAGAGCACTGCAAGATGA  120
GGTCACGGAGGTGGGCAGGGACCGGCTTGTGCCAGGCCTT  160
GCTGGCAGGGTGAAGAGTTTGCCTTTTCTCTGCGTACAAT  200
GGAAAGGAGAAGAGGTTTTAAGCAAGAGAATGGCTTGGTC  240
ATGTGTATGTCTTTGAGACACCCTGGCTAGTCTATGTATG  280
ATGCAAAAGGTGGGTGGGCAGGGTGACAAGAAAATACTG  320
TTCCGGAGCTTCCTGTGGCTGTGCCTATAAGAGGTGGTGG  360
TGGTGGTGTGGAAGGAGGTGTGGCAGTGAATAAACAGAGA  400
TGTAGAAACAGCGTGTACATATATTTTAAGGAACACTGAG  440
GACGTGATGCTGGAATTTGTGATGAGAGAGTGGAAAAAAT  480
CCAGGAAACTTCTAGGACAGAGGCTATTCAACAAGCTCAT  520
GAAGATGACCTTCTATGGGCATTTTGTAGCCGGGGAGGAC  560
CAGGAGTCCATCCAGCCCTGCTTCGGCACTACAGGGCCT  600
TCGGTGTCAGCGCCATCCTGGACTATGGAGTGGAGGAGGA  640
CCTGAGCCCCGAGGAGGCAGAGCACAAGGAGATGGAGTCC  680
TGCACCTCAGCTGCGGAGAGGGATGGCAGTGGCACGAATA  720
AGCGGGACAAGCAATACCAGGCCCACCGGGCCTTCGGGGA  760
CCGCAGGAATGGTGTCATCAGTGCCCGCACCTACTTCTAC  800
GCCAATGAGGCCAAGTGCGACAGCCACATGGAGACATTCT  840
TGCGCTGCATCGAAGCCTCAGGTAGAGTCAGCGATGACGG  880
CTTCATAGCCATTAAGCTCACAGCACTGGGGAGACCCCAG  920
TTTCTGCTGCAGTTCTCAGAGGTGCTGGCCAAGTGGAGGT  960
GCTTCTTTCACCAAATGGCTGTGGAGCAAGGGCAGGCGGG  1000
CCTGGCTGCCATGGACACCAAGCTGGAGGTGGCGGTGCTG  1040
CAGGAAAGTGTCGCAAAGTTGGGCATCGCATCCAGGGCTG  1080
AGATTGAGGACTGGTTCACGGCAGAGACCCTGGGAGTGTC  1120
TGGCACCATGGACCTGCTGGACTGGAGCAGCCTCATCGAC  1160
AGCAGGACCAAGCTGTCCAAGCACCTGGTAGTCCCCAACG  1200
CACAGACAGGACAGCTGGAGCCCTGCTGTCCCGGTTCAC  1240
TGAGGAGGAGGAGCTACAGATGACCAGGATGCTACAGCGG  1280
ATGGATGTCCTGGCCAAGAAAGCCACAGAGATGGGCGTGC  1320
GGCTGATGGTGGATGCCGAGCAGACCTACTTCCAGCCGGC  1360
CATCAGCCGCCTGACGCTGGAGATGCAGCGGAAGTTCAAT  1400
GTGGAGAAGCCGCTCATCTTCAACACATACCAGTGCTACC  1440
TCAAGGATGCCTATGACAATGTGACCCTGGACGTGGAGCT  1480
GGCTCGCCGTGAGGGCTGGTGTTTTGGGGCCAAGCTGGTG  1520
CGGGGCGCATACCTGGCCCAGGAGCGAGCCCGTGCGGCAG  1560
AGATCGGCTATGAGGACCCCATCAACCCCACGTACGAGGC  1600
CACCAACGCCATGTACCACAGGTGCCTGGACTACGTGTTG  1640
GAGGAGCTGAAGCACAACGCCAAGGCCAAGGTGATGGTGG  1680
CCTCCCACAATGAGGACACAGTGCGCTTCGCACTGCGCAG  1720
GATGGAGGAGCTGGGCCTGCATCCTGCTGACCACCAGGTG  1760
TACTTTGGACAGCTGCTAGGCATGTGTGACCAGATCAGCT  1800
TCCCGCTGGGCCAGGCCGGCTACCCCGTGTACAAGTACGT  1840
GCCCTATGGCCCCGTGATGGAGGTGCTGCCCTACTTGTCC  1880
CGCCGTGCCCTGGAGAACAGCAGCCTCATGAAGGGCACCC  1920
```

FIG. 12B

```
ATCGGGAGCGGCAGTTGCTGTGGCTGGAGCTCTTGAGGCG 1960
GCTCCGAACTGGCAACCTCTTCCATCGCCCTGCCTAGCAC 2000
CCGCCAGCACACCCTCAGCCTCCAGCACCCCCGCCCCG 2040
CCCAGGCCATCACCACAGCTGCAGCCAACCCCATCCTCAC 2080
ACAGATTCACCTTTTTTCACCCCACACTTGCAGAGCTGCT 2120
GGAGGTGAGGTCAGGTGCCTCCCAGCCCTGCCCAGAGTAT 2160
GGGCACTCAGGTGTGGGCCGAACCTGATACCTGCCTGGGA 2200
CAGCCACTGGAAACTTTTGGGAACTCTCCTCGAATGTGTG 2240
GCCCAAGGCCCCCACCTCTGTGACCCCATGTCCTTGGAC 2280
CTAGAGGATTGTCCACCTTCTGCCAAGGCCAGCCCACACA 2320
GCCCGAGCCCCTTGGGGAGCAGTGGCCGGGCTGGGGAGGC 2360
CTGCCTGGTCAATAAACCACTGTTCCTGC 2389
```

METHOD OF DETERMINING SUSCEPTIBILITY TO SCHIZOPHRENIA

CROSS REFERENCE TO A RELATED APPLICATION

This Application is a continuation-in-part of U.S. application Ser. No. 09/229,530, filed Jan. 13, 1999 entitled "Methods of Determining Susceptibility to or presence of schizophrenia, or a disorder related thereto" now abadboned, which is hereby incorporated by reference in its entirety.

FIELD OF THE INVENTION

The present invention relates to isolated nucleic acid molecules which encode human and murine proline dehydrogenase, and methods for determining susceptibility to, or the presence of schizophrenia or a disease or disorder related thereto, such as obsessive compulsive disorder, bipolar disorder (BP), or major depressive disorder in a subject by determining levels of proline dehydrogenase (PRODH) in a bodily sample. Furthermore, the present invention comprises polymorphisms of the human proline dehydrogenase (PRODH) gene which correlate to a phenotype closely related to schizophrenia or a disease or disorder related thereto. The present invention also relates to various assays for drugs or agents that can treat schizophrenia or a disease or disorder related thereto.

BACKGROUND OF THE INVENTION

It has been posited that the amino acid proline serves as a modulator of synaptic transmission in the mammalian brain, due to the selective expression of a brain specific high affinity proline transporter in a subset of glutamatergic pathways (Fremeau et al., 1996). Proline transporter is modulated by enckephalins, the expression of which may be decreased in the brains of patients with schizophrenia and elevated proline concentration. Furthermore, recent analysis indicates that endogenous extracellular proline may regulate the basal function of some glutamate synapses by maintaining them in a partially potentiated state. Also, elevated proline concentration has also been previously associated with behavioral and neurological effects.

Evidence of an association between schizophrenia susceptibility and hemizygous deletions in chromosome 22q11 has been reported. More specifically, three hemizygous cryptic deletions at 22q11 in a sample of 300 unrelated schizophrenic patients have been reported and characterized [Karayiorgou et al., Proc. Natl. Acad. Sci. U.S.A. 92, 7612 (1995); Karayiorgou et al., Amer. J. Med. Genet. 74, 677 (1997)]. The frequency of this microdeletion in the general population is estimated to be approximately 0.02% and no deletions were found in a sample of 200 healthy controls. The identified locus (approximately 1.5 Mb in size) is located in the proximal part of a region at chromosome 22q11 and has been implicated independently in schizophrenia susceptibility through linkage studies [Karayiorgou & Gogos, Neuron 19, 967–979 (1997)]. This locus overlaps with the critical region involved in the etiology of Velocardio-facial (VCFS)/DiGeorge (DGS) syndromes [Driscoll et al. 1993]. Furthermore, it has been shown that approximately 29% VCFS children with 22q11 deletions develop schizophrenia or schizoaffective disorder in adolescence and adulthood [Pulver et al., 1994], an estimate confirmed by a more recent independent study [Murphy and Owen, Am. J. Med. Genet., 74, 660 (1997)]. Deletions in chromosome 22, band q11 (22q11) have been identified among schizophrenia patients of diverse ethnic origins (Chinese, Israeli, British, Danish [L. Y. Chow et al., Am. J. Med. Genet. 74, 677 (1997); D. Gothelf et al., Am. J. Med. Genet. 72, 455 (1997); O. Mors and H. Ewald, Am. J. Med. Genet. 74, 677 (1997); Hodginson et al, Am. J. Med. Genet. 61, 565 (1997)]) and the 22q11 region has been implicated in early-onset schizophrenia [Yan et al., 1998]. In addition, the increased rates of comorbid obsessive compulsive disorder (OCD) or symptoms (OCS) among schizophrenic patients with the 22q11 microdeletion locus [Karayiorgou et al., 1996, 1997; Papolos et al., 1996] and similarly increased rates of anxiety, OCS and OCD in children and adults with the 22q11 microdeletion in the absence of schizophrenia [Papolos et al., 1996], potentially indicate that the 22q11 genomic region may harbor one or more genes predisposing to obsessive compulsive disorder (OCD).

Moreover, it has been observed that approximately 20% of schizophrenia patients report obsessions and compulsions, features that are found in only 1–2% of the general population [Eisen & Rasmussen 1993; Berman et al., 1995]. Hence, it is possible that schizophrenia and OCD may share some pathophysiological and genetic components. One common central processing mechanism that seems to be affected in patients with schizophrenia and OCD is sensorimotor gating. Patients with schizophrenia and OCD demonstrate poor sensorimotor gating of the startle response as measured by impaired prepulse inhibition of an acoustic response, and this may lead to sensory overload, distractibility and cognitive fragmentation.

However, there is no genetic marker available which is indicative of a subject's susceptibility to schizophrenia, or a disease related thereto, such as obsessive compulsive disorder (OCD), bipolar disorder (BP), or major depressive disorder (MDD).

Accordingly, what is needed is a genetic marker to assess a subject's susceptibility to schizophrenia or a disease or disorder related thereto. Also needed is a genetic marker to diagnose schizophrenia, and the development of potential drugs or agents that have applications in treating schizophrenia or a disease or disorder related thereto, such as OCD, bipolar disorder, or major depressive disorder.

The citation of any reference herein should not be construed as an admission that such reference is available as "Prior Art" to the instant application.

SUMMARY OF THE INVENTION

There is provided, in accordance with the present invention, an isolated nucleic acid molecule which encodes human proline dehydrogenase, and the amino acid sequence of human proline dehydrogenase. Also provided is an isolated nucleic acid molecule comprising a DNA sequence which encodes murine proline dehydrogenase, and the amino acid sequence of murine proline dehydrogenase. Furthermore, there is provided, in accordance with the present invention, methods for determining a subject's susceptibility to schizophrenia or a disease or disorder related thereto, such as a schizoaffective disorder or disorders related thereto, like OCD, bipolar disorder, or major depressive disorder, using a variant allele of the gene encoding PRODH. Detection of such a variant allele in the genome of a subject may be indicative of the subject's susceptibility to schizophrenia. Furthermore, a variant allele of the PRODH gene can also be used to assay drugs and agents for potential use in treating schizophrenia or a disease or disorder related thereto, such as obsessive compulsive disorder (OCD), bipolar disorder (BP) or major depressive disorder (MDD).

Thus broadly, the present invention extends to an isolated nucleic acid molecule encoding human proline dehydrogenase, wherein the isolated nucleic acid molecule comprises a DNA sequence of SEQ ID NO:1, degenerate variants thereof, fragments thereof, or analogs or derivatives thereof.

Furthermore, the present invention extends to an isolated nucleic acid molecule hybridizable under standard hybridization conditions to the isolated nucleic acid molecule comprising a DNA sequence of SEQ ID NO:1, degenerate variants thereof, fragments thereof, or analogs or derivatives thereof.

The present invention also extends to an isolated nucleic acid molecule comprising a DNA sequence of SEQ ID NO:1, degenerate variants thereof, fragments thereof, or analogs or derivatives thereof, or an isolated nucleic acid molecule hybridzable thereto under standard hybridization conditions, wherein the nucleic acid molecule is detectably labeled. Numerous detectable labels have applications in the present invention. Examples include a radioactive element, such as the isotopes $^3$H, $^{14}$C, $^{32}$P, 35S, $^{36}$Cl, $^{51}$Cr, $^{57}$Co, $^{58}$Co, $^{59}$Fe, $^{90}$Y, $^{125}$I, $^{131}$I, and $^{186}$Re, to name only a few, chemicals which fluoresce, or enzymes such as alkaline phosphatase or horseradish peroxidase conjugated to an isolated nucleic acid molecule of the invention.

Moreover, the present invention extends to an isolated nucleic acid molecule comprising a DNA sequence of SEQ ID NO:1, degenerate variants thereof, fragments thereof, or analogs or derivatives thereof, or an isolated nucleic acid molecule hybridizable under standard hybridization conditions thereto, wherein the nucleic acid molecule encodes human PRODH comprising an amino acid sequence of SEQ ID NO:2, conservative variants thereof, fragments thereof, or analogs or derivatives thereof.

Naturally, the present invention extends to an isolated human proline dehydrogenase protein (PRODH) comprising an amino acid sequence of SEQ ID NO:2, conservative variants thereof, fragments thereof, or analogs or derivatives thereof.

Also, the present invention extends to an antibody having human proline dehydrogenase comprising an amino acid sequence of SEQ ID NO:2, conservative variants thereof, fragments thereof, or analogs or derivatives thereof, as an immunogen. Such an antibody can be polyclonal, monoclonal, or chimeric. Further, an antibody of the invention having human PRODH as an immunogen can be detectably labeled. As explained above, examples of detectable labels having applications herein include, but certainly are not limited to radioactive isotopes, such as $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re, to name only a few. Chemicals which fluoresce, or enzymes such as alkaline phosphatase or horseradish peroxidase, can also be used as detectable labels.

In addition, the present invention extends to cloning vectors for creating copies or "cloning" an isolated nucleic acid molecule of the invention. More specifically, the present invention extends to a cloning vector comprising an isolated nucleic acid molecule comprising a DNA sequence of SEQ ID NO:1, degenerate variants thereof, fragments thereof, or analogs or derivatives thereof, and an origin of replication. In another embodiment, the invention extends to a cloning vector comprising an origin of replication and an isolated nucleic acid molecule hybridizable under standard hybridization conditions to an isolated nucleic acid molecule comprising a DNA sequence of SEQ ID NO:1, degenerate variants thereof, fragments thereof, or analogs or derivatives thereof.

Numerous cloning vectors which are commercially available to the skilled artisan can be used as a cloning vector of the invention. Further, it is readily within the skill of one of ordinary skill in the art to insert an isolated nucleic acid molecule comprising a DNA sequence of SEQ ID NO:1, a degenerate variant thereof, a fragment thereof, or an analog or derivative thereof, or an isolated nucleic acid molecule hybridizable thereto under standard hybridization conditions into a readily available cloning vector using recombinant DNA techniques to produce a cloning vector of the invention. In particular, numerous commercially available cloning vectors have a polylinker site. One of ordinary skill in the art can readily cut open a cloning vector at its polylinker using a variety restriction endonucleases, and then insert the isolated nucleic acid molecule into the vector using DNA ligase. Furthermore, a skilled artisan can also manipulate the ends of an isolated nucleic acid molecule of the invention or fragment thereof to comprise particular restriction sites, and cut those cites with restriction endonucleases which also were used to cut open the vector. The restricted isolated nucleic acid molecule of the invention can then be readily inserted into a cloning vector of the invention. Any remaining gaps in the DNA sequence of the vector can then be filled in using individual deoxynucleotides and DNA ligase. Particular cloning vectors which have applications in the present invention include, but are not limited to E. coli, bacteriophages such as lambda derivatives, plasmids such as pBR322 derivatives, and pUC plasmid derivatives such as pGEX vectors, or pmal-c, pFLAG, to name only a few.

Naturally, the present invention extends to an expression vector for expressing an isolated nucleic acid molecule of the invention in order to produce human PRODH, conservative variants thereof, fragments thereof, or analogs or derivatives thereof. In particular, an expression vector of the invention comprises an isolated nucleic acid molecule comprising a DNA sequence of SEQ ID NO:1, degenerate variants thereof, fragments thereof, or analogs or derivatives thereof, operatively associated with a promoter. In another embodiment, an expression vector of the invention comprises an isolated nucleic acid molecule operatively associated with a promoter, wherein the isolated nucleic acid molecule is hybridzable under standard hybridization conditions to an isolated nucleic acid molecule comprising a DNA sequence of SEQ ID NO:1, degenerate variants thereof, fragments thereof, or analogs or derivatives thereof.

Numerous expression vectors can be used to express an isolated nucleic acid molecule comprising a DNA sequence of SEQ ID NO:1, degenerate variants thereof, fragments thereof, or analogs or derivatives thereof, or an isolated nucleic acid molecule hybridizable thereto under standard hybridization conditions. In particular, such expression vectors are generally commercially available to the skilled artisan, and like cloning vectors, comprise polylinker sites. As a result, commercially available expression vectors can be manipulated in a fashion similar to to the manipulation of a cloning vector, which is described above. Hence a skilled artisan can readily insert an isolated nucleic acid molecule of the invention into an expression vector such that the isolated nucleic acid molecule is operatively associated with a promoter. Examples of expression vectors having applications herein are described infra.

Moreover, the present invention extends to a unicellular host transformed or transfected with an expression vector comprising an isolated nucleic acid molecule operatively associated with a promoter, wherein the isolated nucleic acid molecule encodes a human proline dehydrogenase protein comprising an amino acid sequence of SEQ ID NO:2, conservative variants thereof, fragments thereof, or analogs or derivatives thereof. In one embodiment, the present invention extends to a unicellular host transformed or transfected with an expression vector comprising an isolated nucleic acid molecule operatively associated with a promoter, wherein the isolated nucleic acid molecule comprises a DNA sequence of SEQ ID NO:1, degenerate variants thereof, fragments thereof, or analogs or derivatives thereof. In another embodiment, the invention extends to a unicellular host transformed or transfected with an expression vector comprising an isolated nucleic acid molecule operatively associated with a promoter, wherein the isolated nucleic acid molecule comprises a DNA sequence hybridizable under standard hybridization conditions to an isolated nucleic acid molecule comprising a DNA sequence of SEQ ID NO:1, a degenerate variant thereof, a fragment thereof, or an analog or derivative thereof. Numerous unicellular hosts which are readily available to the skilled artisan have applications in the present invention. Examples include, but certainly are not limited to, *E. coli,* Pseudonomas, Bacillus, Strepomyces, yeast, CHO, R1.1, B-W, L-M, COS1, COS7, BSC1, BSC40, BMT10 and Sf9 cells.

Naturally, the present invention extends to method for producing a PRODH comprising an amino acid sequence of SEQ ID NO:2, conservative variants thereof, fragments thereof, or analogs or derivatives thereof. In one embodiment, the method comprises the steps of:

a) culturing a unicellular host transformed or transfected with an expression vector comprising an isolated nucleic acid molecule which comprises a DNA sequence of SEQ ID NO:1, a degenerate variant thereof, a fragment thereof, or an analog or derivative thereof, operatively associated with a promoter, under conditions that provide for expression of the isolated nucleic acid molecule to produce a protein comprising an amino acid sequence of SEQ ID NO:2, a conservative variant thereof, a fragment thereof, or analog or derivative thereof; and b) recovering the protein from the unicellular host, the culture, or both.

In another embodiment, the method comprises the steps of:

a) culturing a unicellular host transformed or transfected with an expression vector comprising an isolated nucleic acid molecule operatively associated with a promoter, wherein the isolated nucleic acid molecule is hybridizable under standard hybridization conditions to an isolated nucleic acid molecule comprising a DNA sequence of SEQ ID NO:1, a degenerate variant thereof, a fragment thereof, or an analog or derivative thereof, operatively associated with a promoter, under conditions that provide for expression of the isolated nucleic acid molecule, to produce a protein comprising an amino acid sequence of SEQ ID NO:2, a conservative variant thereof, a fragment thereof, or an analog or derivative thereof; and b) recovering the protein from the unicellular host, the culture, or both.

In another embodiment, the present invention extends to an isolated nucleic acid molecule which encodes a human PRODH, wherein the isolated nucleic acid molecule comprises a DNA sequence of SEQ ID NO:9, degenerate variants thereof, fragments thereof, or analogs or derivatives thereof.

Furthermore, the present invention extends to an isolated nucleic acid molecule hybridizable under standard hybridization conditions to the isolated nucleic acid molecule comprising a DNA sequence of SEQ ID NO:9, degenerate variants thereof, fragments thereof, or analogs or derivatives thereof.

The present invention also extends to an isolated nucleic acid molecule comprising a DNA sequence of SEQ ID NO:9, degenerate variants thereof, fragments thereof, or analogs or derivatives thereof, or an isolated nucleic acid molecule hybridzable thereto under standard hybridization conditions, wherein the nucleic acid molecule is detectably labeled. Numerous detectable labels have applications in the present invention and are described infra.

Moreover, the present invention extends to an isolated nucleic acid molecule comprising a DNA sequence of SEQ ID NO:9, degenerate variants thereof, fragments thereof, or analogs or derivatives thereof, or an isolated nucleic acid molecule hybridizable under standard hybridization conditions thereto, which encodes human PRODH comprising an amino acid sequence of SEQ ID NO:2, conservative variants thereof, fragments thereof, or analogs or derivatives thereof.

In addition, the present invention extends to cloning vectors for creating copies or "cloning" an isolated nucleic acid molecule of the invention. More specifically, the present invention extends to a cloning vector comprising an isolated nucleic acid molecule comprising a DNA sequence of SEQ ID NO:9, degenerate variants thereof, fragments thereof, or analogs or derivatives thereof, and an origin of replication. In another embodiment, the invention extends to a cloning vector comprising an origin of replication and an isolated nucleic acid molecule hybridizable under standard hybridization conditions to an isolated nucleic acid molecule comprising a DNA sequence of SEQ ID NO:9, degenerate variants thereof, fragments thereof, or analogs or derivatives thereof.

Numerous cloning vectors which are commercially available to the skilled artisan can be used as a cloning vector of the invention. Further, it is readily within the skill of one of ordinary skill in the art to insert an isolated nucleic acid molecule of the present invention or fragment thereof into a readily available cloning vector using recombinant DNA techniques to produce a cloning vector of the invention. What's more numerous cloning vectors having applications herein are readily available to the skilled artisan, such that with the use of routine experimental techniques and the new and useful isolated nucleic acid molecule comprising a DNA sequence of SEQ ID NO:9, one of ordinary skill can readily produce a cloning vector of the invention. Naturally, routine recombinant DNA techniques describe here can apply to the insertion of any isolated nucleic acid molecule of the invention in to a cloning vector.

Also, the present invention extends to an expression vector for expressing an isolated nucleic acid molecule of the invention in order to produce human PRODH, conservative variants thereof, fragments thereof, or analogs or derivatives thereof. In particular, an expression vector of the invention comprises an isolated nucleic acid molecule comprising a DNA sequence of SEQ ID NO:9, degenerate variants thereof, fragments thereof, or analogs or derivatives thereof, operatively associated with a promoter. In another embodiment, an expression vector of the invention comprises an isolated nucleic acid molecule operatively associated with a promoter, wherein the isolated nucleic acid molecule is hybridzable under standard hybridization conditions to an isolated nucleic acid molecule comprising a DNA sequence of SEQ ID NO:9, degenerate variants thereof, fragments thereof, or analogs or derivatives thereof.

Numerous expression vectors can be used to express an isolated nucleic acid molecule comprising a DNA sequence of SEQ ID NO:9, degenerate variants thereof, fragments thereof, or analogs or derivatives thereof, or an isolated nucleic acid molecule hybridizable thereto under standard hybridization conditions. In particular, such expression vectors are generally commercially available to the skilled artisan, and like cloning vectors, comprise polylinker sites. As a result, commercially available expression vectors can be manipulated in a similar fashion in which cloning vectors of the invention are manipulated. Hence a skilled artisan can readily insert an isolated nucleic acid molecule of the invention into an expression vector such that the isolated nucleic acid molecule is operatively associated with a promoter. Examples of expression vectors having applications herein are described infra.

Moreover, the present invention extends to a unicellular host transformed or transfected with an expression vector comprising an isolated nucleic acid molecule operatively associated with a promoter, wherein the isolated nucleic acid molecule encodes a human proline dehydrogenase protein comprising an amino acid sequence of SEQ ID NO:2, conservative variants thereof, fragments thereof, or analogs or derivatives thereof. In one embodiment, the present invention extends to a unicellular host transformed or transfected with an expression vector comprising an isolated nucleic acid molecule operatively associated with a promoter, wherein the isolated nucleic acid molecule comprises a DNA sequence of SEQ ID NO:9, degenerate variants thereof, fragments thereof, or analogs or derivatives thereof. In another embodiment, the invention extends to a unicellular host transformed or transfected with an expression vector comprising an isolated nucleic acid molecule operatively associated with a promoter, wherein the isolated nucleic acid molecule comprises a DNA sequence hybridizable under standard hybridization conditions to an isolated nucleic acid molecule comprising a DNA sequence of SEQ ID NO:9, a degenerate variant thereof, a fragment thereof, or an analog or derivative thereof. Numerous unicellular hosts which are readily available to the skilled artisan have applications in the present invention, and examples are described above.

Naturally, the present invention extends to method for producing a PRODH comprising an amino acid sequence of SEQ ID NO:2, conservative variants thereof, fragments thereof, or analogs or derivatives thereof. In one embodiment, a method for producing human proline dehydrogenase comprises the steps of:

c) culturing a unicellular host of transformed or transfected with an expression vector comprising an isolated nucleic acid molecule which comprises a DNA sequence of SEQ ID NO:9, a degenerate variant thereof, a fragment thereof, or an analog or derivative thereof, operatively associated with a promoter, under conditions that provide for expression of the isolated nucleic acid molecule to produce a protein comprising an amino acid sequence of SEQ ID NO:2, a conservative variant thereof, a fragment thereof, or analog or derivative thereof; and d) recovering the protein from the unicellular host, the culture, or both.

In another embodiment, the method comprises the steps of:

a) culturing a unicellular host of transformed or transfected with an expression vector comprising an isolated nucleic acid molecule hybridizable under standard hybridization conditions to an isolated nucleic acid molecule comprising a DNA sequence of SEQ ID NO:9, a degenerate variant thereof, a fragment thereof, or an analog or derivative thereof, operatively associated with a promoter, under conditions that provide for expression of the isolated nucleic acid molecule, to produce a protein comprising an amino acid sequence of SEQ ID NO:2, a conservative variant thereof, a fragment thereof, or an analog or derivative thereof; and b) recovering the protein from the unicellular host, the culture, or both.

In another embodiment, the present invention extends to an isolated nucleic acid molecule which encodes murine proline dehydrogenase protein (Prodh). In particular, the present invention extends to an isolated nucleic acid molecule comprising a DNA sequence of SEQ ID NO:3, degenerate variants thereof, fragments thereof, or analogs or derivatives thereof. Naturally, the present invention extends to an isolated nucleic acid molecule which is hybridizable under standard hybridization conditions to an isolated nucleic acid molecule comprising a DNA sequence of SEQ ID NO:3, degenerate variants thereof, fragments thereof, or analogs or derivatives thereof. As explained above, isolated nucleic acid molecules of the invention can be detectably labeled. Examples of detectable labels having applications herein are described infra.

In addition, the present invention extends to an isolated nucleic acid molecule which encodes a Prodh protein comprising an amino acid sequence of SEQ ID NO:4, conservative variants thereof, fragments thereof, or analogs or derivatives thereof. A particular example of such an isolated nucleic acid molecule comprises a DNA sequence of SEQ ID NO:3, degenerate variants thereof, fragments thereof, or analogs or derivatives thereof.

Naturally, the present invention extends to an isolated Prodh protein comprising an amino acid sequence of SEQ ID NO:4, conservative variants thereof, fragments thereof, or analogs or derivatives thereof.

Further, the present invention extends to an antibody having a murine proline dehydrogenase protein, a fragment thereof, a conservative variant thereof, or an analog or derivative thereof as an immunogen. In a particular example, the immunogen of an antibody of the invention is a protein comprising an amino acid sequence of SEQ ID NO:4, conservative variants thereof, fragments thereof, or analogs or derivatives thereof. Furthermore, such an antibody can be polyclonal, monoclonal or chimeric, and optionally can be detectably labeled.

The present invention further extends to cloning vectors which can replicate or "clone" an isolated nucleic acid molecule which encodes a murine proline dehydrogenase protein, conservative variants thereof, fragments thereof, or analogs or derivatives thereof. In one embodiment, a cloning vector of the invention comprises an origin of replication and an isolated nucleic acid molecule comprising the DNA sequence of SEQ ID NO:3, degenerate variants thereof, fragments thereof, or analogs or derivatives thereof. Another embodiment of a cloning vector of the invention comprises an isolated nucleic acid molecule and an origin of replication, wherein the isolated nucleic acid molecule is hybridizable under standard hybridization conditions to an isolated nucleic acid molecule comprising a DNA sequence of SEQ ID NO:3, degenerate variants thereof, fragments thereof, or analogs or derivatives thereof. As explained above, numerous commercially available cloning vectors which comprise a polylinker region have ready applications in the present invention. One of ordinary skill in the art can readily insert an isolated nucleic acid molecule of the invention into a commercially available cloning vector using routine recombinant DNA techniques, described infra. Particular examples of cloning vectors having applications herein include, but certainly are not limited to *E. coli*, bacteriophages, plasmids, or pUC plasmid derivatives. Furthermore, bacteriophage vectors having applications herein include lambda derivatives, plasmids further comprise pBR322 derivatives, and pUC plasmid derivatives further comprise pGEX vectors, or pmal-c, pFLAG, to name only a few.

In addition, the present invention extends to expression vectors for producing a murine proline dehydrogenase protein comprising an amino acid sequence of SEQ ID NO:4, conservative variants thereof, fragments thereof, or analogs or derivatives thereof. In particular, the invention extends to an expression vector comprising an isolated nucleic acid molecule comprising a DNA sequence of SEQ ID NO:3, degenerate variants thereof, fragments thereof, or analogs or derivatives thereof, operatively associated with a promoter. In another embodiment, an expression vector of the invention comprises an isolated nucleic acid molecule operatively associated with a promoter, wherein the isolated nucleic acid molecule is hybridizable under standard hybridization conditions to an isolated nucleic acid molecule comprising a DNA sequence of SEQ ID NO:3, degenerate variants thereof, fragments thereof, or analogs or derivatives thereof. Numerous expression vectors that are commercially available have applications herein. Examples of readily available vectors include derivatives of SV40 and known bacterial plasmids, e.g., *E. coli* plasmids col El, pCR1, pBR322, pMal-C2, pET, pGEX (Smith et al., 1988, Gene 67:31–40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. Insertion of an isolated nucleic acid molecule into such an expression vector is readily within the skill of one of ordinary skill in the art using recombinant DNA techniques described herein.

Further, numerous promoters have applications herein. Examples of such promoters include, but certainly are not limited to immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac system the trp system, the TAC system, the TRC system, the major operator and promoter regions of phage lambda, control regions of fd coat protein, 3-phosphoglycerate kinase promoter, acid phosphatase promoter, or promoters of yeast α mating factor, to name only a few.

The present invention further extends to unicellular hosts transformed or transfected with an expression vector of the invention. In particular, the present invention extends to a unicellular host transformed or transfected with an expression vector comprising an isolated nucleic acid molecule comprising a DNA sequence of SEQ ID NO:3, degenerate variants thereof, fragments thereof, or analogs or derivatives thereof, operatively associated with a promoter. In another embodiment, the present invention extends to a unicellular host transformed or transfected with an expression vector comprising an isolated nucleic acid molecule operatively associated with a promoter, wherein the isolated nucleic acid molecule is hybridizable under standard hybridization conditions to an isolated nucleic acid molecule comprising a DNA sequence of SEQ ID NO:3, degenerate variants thereof, fragments thereof, or analogs or derivative thereof. Examples of unicellular hosts having applications herein include but certainly are not limited to *E. coli,* Pseudonomas, Bacillus, Strepomyces, yeast, CHO, R1.1, B-W, L-M, COS1, COS7, BSC1, BSC40, BMT10 or Sf9 cells.

Naturally, the present invention extends to methods of producing a murine proline dehydrogenase protein comprising an amino acid sequence of SEQ ID NO:4, conservative variants thereof, fragments thereof, or analogs or derivatives thereof. In one embodiment, the method comprises the steps of:

a) culturing a unicellular host transformed or transfected with an expression vector comprising an isolated nucleic acid molecule comprising a DNA sequence of SEQ ID NO:3, a degenerate variant thereof, a fragment thereof, or an analog or derivative thereof, operatively associated with a promoter, under conditions that provide for expression of the isolated nucleic acid molecule to produce a protein comprising an amino acid sequence of SEQ ID NO:4, conservative variant thereof, fragment thereof, or analog or derivative thereof; and b) recovering the protein from the unicellular host, the culture, or both.

In another embodiment, the method comprises the steps of:

a) culturing a unicellular host transformed or transfected with an expression vector comprising an isolated nucleic acid molecule operatively associated with a promoter, wherein the isolated nucleic acid molecule is hybridizable under standard hybridization conditions to an isolated nucleic acid molecule comprising a DNA sequence of SEQ ID NO:3, degenerate variants thereof, fragments thereof, or analogs or derivatives thereof under conditions that provide for expression of the isolated nucleic acid molecule to produce a protein comprising an amino acid sequence of SEQ ID NO:4, conservative variant thereof, fragment thereof, or analog or derivative thereof; and b) recovering the protein from the unicellular host, the culture, or both.

The present invention further extends to an isolated variant allele of a human proline dehydrogenase (PRODH) gene, wherein the PRODH gene comprises a DNA sequence of SEQ ID NO:1, and the variant allele comprises a DNA sequence having at least one variation in SEQ ID NO:1, wherein the at least one variation comprises:

a G to A transition in the third position of codon 83;

a C to T transition in the first position of codon 101;

a G to A transition in the second position of codon 101;

a C to T transition in the first position of codon 247;

a C to T transition in the third position of codon 342;

a C to T transition in the third position of codon 421;

an A to G transition in the second position of codon 437;

a T to C transition in the first position of codon 497; or a combination thereof.

Moreover, the present invention extends to an isolated nucleic acid molecule hybridizable under standard hybridization conditions to an isolated variant allele of a human PRODH gene, wherein the isolated variant allele comprises a DNA sequence having at least one variation in SEQ ID NO:1, and the at least one variation comprises:

a G to A transition in the third position of codon 83;

a C to T transition in the first position of codon 101;

a G to A transition in the second position of codon 101;

a C to T transition in the first position of codon 247;

a C to T transition in the third position of codon 342;

a C to T transition in the third position of codon 421;

an A to G transition in the second position of codon 437;

a T to C transition in the first position of codon 497; or a combination thereof.

In addition, the present invention extends to a detectably labeled isolated variant allele of a PRODH gene, wherein the PRODH gene comprises a DNA sequence of SEQ ID NO:1, and the variant allele comprises a DNA sequence having at least one variation in SEQ ID NO:1, wherein the at least one variation comprises:

a G to A transition in the third position of codon 83;

a C to T transition in the first position of codon 101;

a G to A transition in the second position of codon 101;

a C to T transition in the first position of codon 247;

a C to T transition in the third position of codon 342;

a C to T transition in the third position of codon 421;

an A to G transition in the second position of codon 437;

a T to C transition in the first position of codon 497; or a combination thereof.

Numerous detectable labels have applications in the present invention. For example the detectable label can be a radioactive element, such as the isotopes $^3$H, $^{14}$C, $^{32}$P, 35S, $^{36}$Cl, $^{51}$Cr, $^{57}$Co, $^{58}$Co, $^{59}$Fe, $^{90}$Y, $^{125}$I, $^{131}$I, and $^{186}$Re, to name only a few. Chemicals which fluoresce, or enzymes such as alkaline phosphatase or horseradish peroxidase, can also be used as detectable labels.

Moreover, the present invention extends to a detectably labeled isolated nucleic acid molecule hybridizable under standard hybridization conditions to an isolated variant allele of a PRODH gene, wherein the PRODH gene comprises a DNA sequence of SEQ ID NO:1, and the variant allele comprises a DNA sequence having at least one variation in SEQ ID NO:1, wherein the at least one variation comprises:

a G to A transition in the third position of codon 83;

a C to T transition in the first position of codon 101;

a G to A transition in the second position of codon 101;

a C to T transition in the first position of codon 247;

a C to T transition in the third position of codon 342;

a C to T transition in the third position of codon 421;

an A to G transition in the second position of codon 437;

a T to C transition in the first position of codon 497; or a combination thereof.

Detectable labels set forth throughout the specification have applications in such an isolated nucleic acid molecule.

In addition, the present invention extends to an isolated variant allele of a PRODH gene which encodes a variant human proline PRODH comprising at least one variation in the amino acid sequence of PRODH, wherein PRODH comprises an amino acid sequence of SEQ ID NO:2, and is encoded by a human proline dehydrogenase gene comprising a DNA sequence of SEQ ID NO:1. A variant PRODH protein of the present invention comprises an amino acid sequence having at least one variation in SEQ ID NO:2, wherein the at least one variation comprises:

Arg101Trp;

Arg101Glu;

Glu437Arg; or a combination thereof.

In particular, a variant allele of a human PRODH gene comprising a DNA sequence comprising a C to T transition in the first position of codon 101 of SEQ ID NO:1, encodes a variant human PRODH protein comprising an amino acid sequence comprising an Arg101Trp variation in SEQ ID NO:2. Furthermore, a variant allele of a human PRODH gene comprising a DNA sequence having a G to A transition in the second position of codon 101 of SEQ ID NO:1 encodes a variant human PRODH protein comprising an amino acid sequence having an Arg101Glu variation in SEQ ID NO:2. Hence naturally, a variant allele of a human PRODH gene comprising a DNA sequence having an A to G transition in the second position of codon 437 of SEQ ID NO:1 encodes a variant human PRODH protein comprising an amino acid sequence having a Glu437Arg variation in SEQ ID NO:2. As explained above, the present invention also extends to a variant allele of a human PRODH gene comprising a combination of variations set forth herein, which encode a variant human PRODH protein comprising an amino acid sequence having a combination of amino acid residue variations in SEQ ID NO:2 as described above.

Naturally, the present invention extends to an isolated variant human PRODH protein comprising an amino acid sequence having at least one variation in SEQ ID NO:2, wherein the at least one variation comprises:

Arg101Trp;

Arg101Glu;

Glu437Arg; or a combination thereof.

Furthermore, the present invention extends to an antibody having a variant proline dehydrogenase protein of the present invention as an immunogen. Such an antibody can be a polyclonal antibody, a monoclonal antibody, or a chimeric antibody. Moreover, an antibody of the present invention can be detectably labeled. Examples of detectable labels which have applications in this embodiment comprises a radioactive element, a chemical which fluoresces, or an enzyme, to name only a few.

In addition, the present invention extends to cloning vectors that can be used to clone copies of a variant allele of a PRODH gene of the present invention. An example of such a cloning vector comprises an origin of replication and an isolated variant allele of a human PRODH gene, wherein the PRODH gene comprises a DNA sequence of SEQ ID NO:1, and an isolated variant allele of the PRODH gene comprises a DNA sequence having at least one variation in SEQ ID NO:1 wherein the at least one variation comprises:

a G to A transition in the third position of codon 83;

a C to T transition in the first position of codon 101;

a G to A transition in the second position of codon 101;

a C to T transition in the first position of codon 247;

a C to T transition in the third position of codon 342;

a C to T transition in the third position of codon 421;

an A to G transition in the second position of codon 437;

a T to C transition in the first position of codon 497; or a combination thereof.

Moreover, the present invention extends to a cloning vector comprising an origin of replication and an isolated nucleic acid molecule hybridizable under standard hybridization conditions to an isolated variant allele of a PRODH gene, wherein the PRODH gene comprises a DNA sequence of SEQ ID NO:1, and the isolated variant allele of the PRODH gene comprises a DNA sequence having at least one variation in SEQ ID NO:1 wherein the at least one variation comprises:

a G to A transition in the third position of codon 83;

a C to T transition in the first position of codon 101;

a G to A transition in the second position of codon 101;

a C to T transition in the first position of codon 247;

a C to T transition in the third position of codon 342;

a C to T transition in the third position of codon 421;

an A to G transition in the second position of codon 437;

a T to C transition in the first position of codon 497; or a combination thereof.

Numerous cloning vectors have applications in the present invention and are readily available to a skilled artisan. Furthermore, it is well within the knowledge of one of ordinary skill in the art to insert an isolated PRODH variant allele of the present invention into a commercially available cloning vector using recombinant DNA techniques described infra. Examples of a cloning vector having applications in the present invention include E. coli, bacteriophages, such as lambda derivatives, plasmids, such as pBR322 derivatives, and pUC plasmid derivatives, such as pGEX vectors, or pmal-c, pFLAG, to name only a few.

The present invention further extends to a unicellular host transformed or transfected with a cloning vector which comprises an isolated variant allele of the human PRODH gene as described above. Examples of hosts which are readily available to the skilled artisan and can be transformed or transfected with a cloning vector of the present invention include, but are not limited to E. coli, Pseudonomas, Bacillus, Strepomyces, yeast, CHO, R1.1, B-W, L-M, COS1, COS7, BSC1, BSC40, BMT10 or Sf9 cells.

The present invention further extends to a method of cloning or producing "copies" of an isolated variant allele of a human PRODH gene of the invention, which comprises inserting a cloning vector into a unicellular host, and then inducing the host to self replicate. During the self replication of the host, the origin of replication of the cloning vector causes the replication of the cloning vector. After the unicellular host has self replicated numerous times, the cloning vectors can be isolated from the cloned host, and the isolated nucleic acid molecule can be isolated via restriction digestion from the cloning vectors.

Naturally, the present invention extends to expression vectors comprising an isolated variant allele of a PRODH gene operatively associated with a promoter, wherein the PRODH gene comprises a DNA sequence of SEQ ID NO:1, and an isolated variant allele of the present invention comprises a DNA sequence having at least one variation in SEQ ID NO:1 wherein the at least one variation comprises:

a G to A transition in the third position of codon 83;

a C to T transition in the first position of codon 101;

a G to A transition in the second position of codon 101;

a C to T transition in the first position of codon 247;

a C to T transition in the third position of codon 342;

a C to T transition in the third position of codon 421;

an A to G transition in the second position of codon 437;

a T to C transition in the first position of codon 497; or a combination thereof.

Furthermore, the present invention extends to an expression vector comprising an isolated nucleic acid molecule operatively associated with a promoter, wherein the isolated nucleic acid molecule is hybridizable under standard hybridization conditions to an isolated variant allele of a PRODH gene, wherein the PRODH gene comprises a DNA sequence of SEQ ID NO:1, and an isolated variant allele of the present invention comprises a DNA sequence having at least one variation in SEQ ID NO:1 wherein the at least one variation comprises:

a G to A transition in the third position of codon 83;

a C to T transition in the first position of codon 101;

a G to A transition in the second position of codon 101;

a C to T transition in the first position of codon 247;

a C to T transition in the third position of codon 342;

a C to T transition in the third position of codon 421;

an A to G transition in the second position of codon 437;

a T to C transition in the first position of codon 497; or a combination thereof.

Numerous promoters which are readily available to a skilled artisan, have applications in any expression vector of the invention. For example, immediate early promoters of hCMV, early promoters of SV40, early promoters of adenovirus, early promoters of vaccinia, early promoters of polyoma, late promoters of SV40, late promoters of adenovirus, late promoters of vaccinia, late promoters of polyoma, the lac system, the trp system, the TAC system, the TRC system, the major operator and promoter regions of phage lambda, control regions of fd coat protein, 3-phosphoglycerate kinase promoter, acid phosphatase promoter, or promoters of yeast a mating factor, to name only a few, have applications herein. Furthermore, it is well within the knowledge of one of ordinary skill in the art to insert an isolated variant allele of the invention, or an isolated nucleic acid molecule hybridizable under standard hybridization conditions to an isolated variant allele of the invention into a commercially available expression vector, using recombinant DNA techniques described infra.

In addition, the present invention extends to a unicellular host transformed or transfected with an expression vector of the present invention. Examples of hosts which can be transformed or transfected with an expression vector of the present invention, and have applications in the present invention, include, but are not limited to, E. coli, Pseudonomas, Bacillus, Strepomyces, yeast, CHO, R1.1, B-W, L-M, COS1, COS7, BSC1, BSC40, BMT10 or Sf9 cells.

Naturally, the present invention extends to a method for producing a variant human PRODH protein comprising an amino acid having at least one variation in SEQ ID NO:2, wherein the at least one variation comprises Arg101Trp;

Arg101Glu;

Glu437Arg; or a combination thereof.

An example of such a method comprises the steps of culturing a unicellular host transformed or transfected with an expression vector comprising an isolated variant allele of a PRODH gene operatively associated with a promoter, wherein the isolated variant allele of the PRODH gene comprises a DNA sequence having at least one variation in SEQ ID NO:1, and the at least one variation comprises:

a G to A transition in the third position of codon 83;

a C to T transition in the first position of codon 101;

a G to A transition in the second position of codon 101;

a C to T transition in the first position of codon 247;

a C to T transition in the third position of codon 342;

a C to T transition in the third position of codon 421;

an A to G transition in the second position of codon 437;

a T to C transition in the first position of codon 497; or a combination thereof,
under conditions that provide for expression of the variant allele. The variant PRODH protein produced from such expression is then recovered from the unicellular host, the culture, or both.

Yet another method of the present invention for producing a variant PRODH protein involves culturing a unicellular host transformed or transfected with an expression vector comprising an isolated nucleic acid molecule operatively associated with a promoter, wherein the isolated nucleic acid molecule is hybridizable under standard hybridization conditions to an isolated variant allele of a PRODH gene comprising a DNA sequence having at least one variation in SEQ ID NO:1, wherein the at least one variation comprises:

a G to A transition in the third position of codon 83;
a C to T transition in the first position of codon 101;
a G to A transition in the second position of codon 101;
a C to T transition in the first position of codon 247;
a C to T transition in the third position of codon 342;
a C to T transition in the third position of codon 421;
an A to G transition in the second position of codon 437;
a T to C transition in the first position of codon 497; or
a combination thereof, under conditions that provide for expression of the isolated nucleic acid molecule. The variant human PRODH protein produced from such induced expression is then recovered from the unicellular host, the culture, or both.

Furthermore, the present invention extends to a method for detecting a susceptibility to, or the presence of schizophrenia or a disease or disorder related thereto, such as obsessive compulsive disorder (OCD), bipolar disorder (BP) or major depressive disorder in a subject, wherein the method comprises measurement of the levels of activity of an enzyme in a bodily sample which is involved in proline catabolism. A comparison of the measurement of the levels of activity of the enzyme in the bodily sample is then made with the levels of activity of the enzyme in a standard. A modulated level of enzyme activity in the sample relative to the level of activity in the standard is indicative of a susceptibility to, or the presence of, schizophrenia or a disease or disorder related thereto, such as obsessive compulsive disorder (OCD), bipolar disorder (BP) or major depressive disorder, in the subject. In a particular embodiment, the enzyme involved in proline catabolism is proline dehydrogenase (PRODH), and a reduced level of activity of PRODH in a bodily sample from the subject compared to the level of PRODH activity in the standard is indicative of increased susceptibility to, or the presence of schizophrenia or a disease or disorder related thereto in the subject relative to the susceptibility of the standard. Methods of assaying activity of proline dehydrogenase in a bodily sample are readily available to the skilled artisan.

The present invention further extends to a method for determining a susceptibility to, or the presence of schizophrenia or a disease or disorder related thereto in a subject, such as obsessive compulsive disorder (OCD), bipolar disorder (BP) or major depressive disorder (MDD), wherein the method comprises the steps of:

a) removing a bodily sample from the subject, wherein the sample comprises a PRODH gene; and
b) determining whether the PRODH gene of the bodily sample comprises a DNA sequence having a variation in SEQ ID NO:1 comprising a T to C transition in the first position of codon 497. The presence of the variant allele the PRODH gene in a bodily sample of the subject indicates the subject has an increased susceptibility to schizophrenia or a disease or disorder related thereto, such as obsessive compulsive disorder (OCD), bipolar disorder (BP) or major depressive disorder (MDD) relative to the susceptibility of a standard, wherein the bodily sample of the standard comprises a PRODH gene comprising a DNA sequence of SEQ ID NO:1.

Furthermore, the present invention extends to an assay for screening drugs and other agents for ability to treat schizophrenia or a disease or disorder related thereto. Such an assay of the present invention comprises the steps of culturing an observable cellular test colony which produces PRODH and which has been inoculated with the drug or agent to be assayed, harvesting a cellular extract from the cellular test colony, and determining the level of activity of PRODH in the test colony. An increase or decrease in the level of activity of PRODH in this test colony compared to a control test colony not inoculated with the drug, or compared to the level of activity of PRODH in the cellular test colony prior to inoculation with the drug or agent, is indicative of the ability of the drug or agent to modulate the production, stability, degradation or activity of PRODH, which in turn is indicative of the drug or agent's ability to treat schizophrenia or a disease or disorder related thereto, such as obsessive compulsive disorder (OCD), bipolar disorder (BP) or major depressive disorder. An increase in the level of activity of PRODH in the test colony after inoculation with the drug or agent compared to the level of activity in the control colony, or in the cellular test colony prior to inoculation with the drug or agent, indicates the drug has the ability to be used to treat schizophrenia or a disorder related thereto.

In another embodiment, the present invention extends to an assay system which may be prepared in the form of a test kit for the quantitative analysis of the extent of the presence and/or activity of PRODH, or to identify drugs or other agents that may potentiate or increase such activity. Broadly, a system or test kit of the present invention may comprise a labeled component prepared by one of the radioactive and/or enzymatic techniques discussed herein, coupling the label to PRODH, its agonists and/or antagonists, and one or more additional immunochemical reagents, at least one of which is a free or immobilized ligand, capable either of binding with the labeled component, its binding partner, one of the components to be determined, or their binding partner(s). The system or test kit may also comprise a polymerase chain reaction based (PCR) assay which can be used to quantify the PRODH levels of a sample.

Hence, the present invention extends to a test kit to facilitate diagnosis and treatment of schizophrenia or a disease or disorder related thereto, such as obsessive compulsive disorder (OCD), bipolar disorder (BP) or major depressive disorder, comprising:

(a) a predetermined amount of a detectably labeled specific binding partner of a PRODH protein;
(b) other reagents; and
(c) directions for use of said kit.

Examples of the labeled immunochemically reactive component of such a test kit can be selected from the group consisting of polyclonal antibodies to PRODH, monoclonal antibodies to PRODH, chimeric antibodies to PRODH, fragments of such antibodies, and mixtures of such antibodies.

Furthermore, the present invention extends to a test kit to facilitate diagnosis and treatment of schizophrenia or a disease or disorder related thereto in a subject, wherein the test kit comprises:

(a) PCR oligonucleotide primers suitable to detecting a variant allele of the PRODH gene in a sample;

(b) other reagents; and (c) directions for use of the kit.

The present invention further extends to a test kit to facilitate diagnosis and treatment of schizophrenia or a disease or disorder related thereto in a eukaryotic cellular sample, wherein the test kit comprises:

(a) PCR oligonucleotide primers suitable for detection of an isolated variant allele of a PRODH gene, wherein the PRODH gene comprises a DNA sequence of SEQ ID NO:1, and the isolated variant comprises a DNA sequence comprising a T to C transition in the first position of codon 497 of SEQ ID NO:1;

(b) other reagents; and (c) directions for use of the kit.

In another embodiment, the present invention extends to treating schizophrenia or a disease or disease or disorder related thereto in a subject, such as obsessive compulsive disorder (OCD), bipolar disorder (BP) or major depressive disorder. An example of such a method comprises administering to the subject a therapeutically effective amount of a composition comprising PRODH, wherein PRODH comprises an amino acid sequence of SEQ ID NO:2, conservative variants thereof, fragments thereof, or analogs or derivatives thereof. Optionally, the composition of the invention can be administered alone or in combination with additional therapeutic agents to treat the subject.

In addition, the present invention extends to a method for determining the schizophrenic-related pharmacological activity of an agent, wherein the method comprises the steps of:

administering the agent to a mammal;

determining the level of activity of PRODH in the mammal; and comparing the level of activity of PRODH in the mammal to the level of activity of PRODH in a control mammal to which the agent was not administered. An increase in the level of activity of PRODH in the mammal relative to activity of PRODH in the control mammal indicates the agent has a schizophrenic-related pharmacological activity, and potential as a therapeutic agent for treating schizophrenia or a disease or disorder related thereto, such as obsessive compulsive disorder (OCD), bipolar disorder (BP) or major depressive disorder.

In yet another aspect, the present invention extends to a method for determining the schizophrenic-related pharmacological activity of an agent, wherein the method comprises the steps of:

determining a basal level of activity of PRODH in the mammal;

administering the agent to the mammal;

determining the level of activity of PRODH in the mammal after administration of the agent; and comparing the level of activity of PRODH after administration of the agent to the basal level of activity.

An increase in the level of activity of PRODH in the mammal relative to the basal level in the mammal indicates the compound has a schizophrenic-related pharmacological activity, and may have potential as a therapeutic agent for treating schizophrenia or a disease or disorder related thereto, such as obsessive compulsive disorder (OCD), bipolar disorder (BP) or major depressive disorder.

What's more, the present invention extends to an isolated variant allele of the Prodh gene which encodes a mutated murine Prodh protein. In particular, the present invention extends to an isolated variant allele of the Prodh gene, wherein the isolated variant allele comprises a DNA sequence of FIG. 10 (SEQ ID NO:7), degenerate variants thereof, fragments thereof, or analogs or derivatives thereof.

The present invention also extends to an isolated nucleic acid molecule hybridzable under standard hybridization conditions to the isolated variant allele of the murine Prodh gene comprising a DNA sequence of SEQ ID NO:7, degenerate variants thereof, fragments thereof, or analogs or derivatives thereof.

In addition, the present invention extends to an isolated variant allele of the Prodh gene which comprises a DNA sequence of SEQ ID NO:7, degenerate variants thereof, fragments thereof, or analogs or derivatives thereof, detectably labeled. Naturally, the present invention extends to an isolated nucleic acid molecule detectably labeled, wherein the isolated nucleic acid molecule is hybridizable under standard hybridization conditions to an isolated variant allele of the Prodh gene, wherein the isolated variant allele comprises a DNA sequence of SEQ ID NO:7, degenerate variants thereof, fragments thereof, or analogs or derivatives thereof.

Moreover, the present invention extends to an isolated nucleic acid molecule encoding an isolated mutant murine Prodh protein comprising an amino acid sequence of FIG. 11 (SEQ ID NO:8), conservative variants thereof, fragments thereof, or analogs or derivatives thereof.

Naturally, the present invention extends to an isolated Prodh comprising an amino acid sequence of SEQ ID NO:8, conservative variants thereof, fragments thereof, or analogs or derivatives thereof.

Also, the present invention extends to an antibody having an isolated mutant Prodh of the invention, conservative variants thereof, fragments thereof, or analogs or derivatives thereof as an immunogen. Such an antibody can be polyclonal, monoclonal, or chimeric. Further, such an antibody can be detectably labeled. As explained above, numerous examples of detectable labels having applications in an antibody of the invention are described infra.

In addition, the present invention extends to cloning vectors for creating copies or "cloning" an isolated variant allele of a Prodh gene of the invention, degenerate variants thereof, fragments thereof, or analogs or derivatives thereof. In particular, the present invention extends to a cloning vector comprising an isolated variant allele of a Prodh gene, wherein the isolated variant allele comprises a DNA sequence of SEQ ID NO:7, degenerate variants thereof, fragments thereof, or analogs or derivatives thereof, and an origin of replication. In another embodiment, the invention extends to a cloning vector comprising an origin of replication and an isolated nucleic acid molecule hybridizable under standard hybridization conditions to an isolated variant allele of a Prodh gene, wherein the isolated variant allele comprises a DNA sequence of SEQ ID NO:7, degenerate variants thereof, fragments thereof, or analogs or derivatives thereof.

Numerous cloning vectors which are commercially available to the skilled artisan, and can be used as a cloning vector for an isolated variant allele of a Prodh gene. Examples of such cloning vectors, and routine recombinant DNA techniques to produce such a vector are described infra.

Naturally, the present invention extends to an expression vector for expressing an isolated variant allele of a murine Prodh gene, degenerate variants thereof, fragments thereof, or analogs or derivatives thereof, along with an isolated nucleic acid molecule hybridizable thereto under standard hybridization conditions, to produce a mutated murine Prodh protein, conservative variants thereof, fragments thereof, or analogs or derivatives thereof. In particular, an expression vector of the invention comprises an isolated variant allele of the murine Prodh gene, wherein the isolated variant allele comprises a DNA sequence of SEQ ID NO:7, degenerate variants thereof, fragments thereof, or analogs or derivatives thereof, operatively associated with a promoter. In another embodiment, an expression vector of the invention comprises an isolated nucleic acid molecule operatively associated with a promoter, wherein the isolated nucleic acid molecule is hybridzable under standard hybridization conditions to an isolated variant allele of the Prodh gene, wherein the isolated variant allele comprises a DNA sequence of SEQ ID NO:7, degenerate variants thereof, fragments thereof, or analogs or derivatives thereof.

Numerous expression vectors can be used to express the isolated variant allele of the Prodh gene, degenerate variants thereof, fragments thereof, or analogs or derivatives thereof, or an isolated nucleic acid molecule hybridizable to the isolated variant allele under standard hybridization conditions. In particular, such expression vectors are generally commercially available to the skilled artisan, and like cloning vectors, comprise polylinker sites. As a result, commercially available expression vectors can be manipulated in a similar fashion in which cloning vectors of the invention are manipulated. Hence a skilled artisan can readily insert the isolated variant allele of the Prodh gene, degenerate variants thereof, fragments thereof, or analogs or derivatives thereof, or an isolated nucleic acid molecule hybridizable thereto under standard hybridization conditions into an expression vector such that the isolated variant allele or an isolated nucleic acid molecule hybridizable thereto under standard hybridization conditions is operatively associated with a promoter. Examples of expression vectors having applications herein are described infra.

Moreover, the present invention extends to a unicellular host transformed or transfected with an expression vector comprising an isolated variant allele of the Prodh gene, operatively associated with a promoter, wherein the isolated variant allele encodes a mutant murine proline dehydrogenase protein comprising an amino acid sequence of SEQ ID NO:8, conservative variants thereof, fragments thereof, or analogs or derivatives thereof. In one embodiment, the present invention extends to a unicellular host transformed or transfected with an expression vector comprising an isolated variant allele of the Prodh gene, operatively associated with a promoter, wherein the isolated variant allele comprises a DNA sequence of SEQ ID NO:7, degenerate variants thereof, fragments thereof, or analogs or derivatives thereof. In another embodiment, the invention extends to a unicellular host transformed or transfected with an expression vector comprising an isolated nucleic acid molecule operatively associated with a promoter, wherein the isolated nucleic acid molecule is hybridizable under standard hybridization conditions to an isolated variant allele of the Prodh gene, wherein the isolated variant allele comprises a DNA sequence of SEQ ID NO:7, a degenerate variant thereof, a fragment thereof, or an analog or derivative thereof. Numerous unicellular hosts which are readily available to the skilled artisan have applications in the present invention.

Naturally, the present invention extends to method for producing a mutant murine proline dehydrogenase protein comprising an amino acid sequence of SEQ ID NO:8, conservative variants thereof, fragments thereof, or analogs or derivatives thereof. In one embodiment, a method for producing a mutant murine proline dehydrogenase comprises the steps of:

a) culturing a unicellular host of transformed or transfected with an expression vector comprising an isolated variant allele of the prodh gene, wherein the isolated variant allele comprises a DNA sequence of SEQ ID NO:7, a degenerate variant thereof, a fragment thereof, or an analog or derivative thereof, operatively associated with a promoter, under conditions that provide for expression of the isolated variant allele to produce a mutant murine proline dehydrogenase protein comprising an amino acid sequence of SEQ ID NO:8, a conservative variant thereof, a fragment thereof, or analog or derivative thereof; and b) recovering the protein from the unicellular host, the culture, or both.

In another embodiment, the method comprises the steps of:

a) culturing a unicellular host of transformed or transfected with an expression vector comprising an isolated nucleic acid molecule hybridizable under standard hybridization conditions to an isolated variant allele of the Prodh gene, wherein the isolated variant allele comprises a DNA sequence of SEQ ID NO:7, a degenerate variant thereof, a fragment thereof, or an analog or derivative thereof, operatively associated with a promoter, under conditions that provide for expression of the isolated nucleic acid molecule, to produce a protein comprising an amino acid sequence of SEQ ID NO:8, a conservative variant thereof, a fragment thereof, or an analog or derivative thereof; and b) recovering the protein from the unicellular host, the culture, or both.

Furthermore, the present invention extends to a method for identifying a drug or agent for treating schizophrenia or a disease or disorder related thereto. An example of such a method comprises the steps of:

performing an first pre-pulse inhibition test (PPI) test on a mouse having within its genome two copies of an isolated variant allele of a Prodh gene comprising a DNA sequence of SEQ ID NO:7, wherein both copies are capable of expressing a mutant Prodh comprising an amino acid sequence of SEQ ID NO:8, to obtain a first percentage of inhibition of startle response;

administering the potential drug or agent to the mouse;

performing a second PPI test on the mouse to obtain a second percentage of inhibition of startle response; and comparing the first percentage to the inhibition of startle response with the second percentage of startle response, wherein an increase in percentage of inhibition in the second percentage of inhibition relative to the first percentage of inhibition is indicative of the ability of the drug or agent to treat schizophrenia or a disease or disorder related thereto. Thus, if the percentage of inhibition of startle response in the mouse having within its two active copies of an isolated variant allele of a Prodh gene comp mouse after administration of the drug or agent is greater than the percentage of inhibition of startle response in the Pro/Re mouse prior to inhibition, then the drug or agent has the ability to treat schizophrenia or a disease or disorder related thereto, such as obsessive compulsive disorder (OCD), bipolar disorder (BP) or major depressive disorder.

Also, the present invention extends to a method for identifying a drug or agent for treating schizophrenia or a disease or disorder related thereto. An example of such a method comprises the steps of:

performing an first pre-pulse inhibition test (PPI) test on an F3 generation mouse from a cross Pro/Re X C57B1/6J wild-type, wherein the F3 generation mouse has two copies within its genome of an isolated variant allele of a Prodh gene comprising a DNA sequence of SEQ ID NO:7 which are capable of expressing a mutant Prodh comprising an amino acid sequence of SEQ ID NO:8, to obtain a first percentage of inhibition of startle response;

administering the potential drug or agent to the F3 generation mouse from a cross of Pro/Re X C57B1/6J wild-type;

performing a second PPI test on the F3 generation mouse from a cross of Pro/Re X C57B1/6J wild-type to obtain a second percentage of inhibition of startle response; and comparing the first percentage to the inhibition of startle response with the second percentage of startle response, wherein an increase in percentage of inhibition in the second percentage of inhibition relative to the first percentage of inhibition is indicative of the ability of the drug or agent to treat schizophrenia or a disease or disorder related thereto.

What's more, the present invention extends to a method for identifying a drug or agent for use in treating schizophrenia or a disease or disorder related thereto, comprising the steps of:

a) administering the drug or agent to an F3 generation mouse from a cross of Pro/Re X C57B1/6J wild-type, wherein the F3 generation mouse has two copies within its genome of an isolated variant allele of a Prodh gene comprising a DNA sequence of SEQ ID NO:7 which are capable of expressing a mutant Prodh comprising an amino acid sequence of SEQ ID NO:8;

b) performing a PPI test on the F3 generation mouse from a cross of Pro/Re X C57B1/6J wild-type to obtain a percentage of inhibition of the startle response in the F3 generation mouse from a cross of Pro/Re X C57B1/6J wild-type which was administered the drug or agent; and c) comparing the percentage of inhibition of the startle response in the F3 generation mouse from a cross of Pro/Re X C57B1/6J wild-type with the percentage of inhibition of the startle response in an unmedicated F3 generation mouse from a cross of Pro/Re X C57B1/6J wild-type, wherein the F3 generation mouse has two copies within its genome of an isolated variant allele of a Prodh gene comprising a DNA sequence of SEQ ID NO:7 which are capable of expressing a mutant Prodh comprising an amino acid sequence of SEQ ID NO:8.

An increase in percentage of inhibition in the percentage of inhibition in the medicated mouse relative to the percentage of inhibition in the unmedicated mouse is indicative of the ability of the drug or agent to treat schizophrenia or a disease or disorder related thereto.

Furthermore, the present invention extends to a method for identifying a drug or agent for use in treating schizophrenia or a disease or disorder related thereto, comprising the steps of:

a) administering the drug or agent to a mouse having within its genome two copies of an isolated variant allele of a Prodh gene comprising a DNA sequence of SEQ ID NO:7, wherein both copies are capable of expressing a mutant Prodh comprising an amino acid sequence of SEQ ID NO:8;

b) performing a PPI test on the mouse to obtain a percentage of inhibition of the startle response in the mouse; and c) comparing the percentage of inhibition of the startle response in the mouse with the percentage of inhibition of the startle response in an unmedicated mouse having within its genome two copies of an isolated variant allele of a Prodh gene comprising a DNA sequence of SEQ ID NO:7, wherein both copies are capable of expressing a mutant Prodh comprising an amino acid sequence of SEQ ID NO:8.

An increase in percentage of inhibition in the percentage of inhibition in the medicated mouse relative to the percentage of inhibition in the unmedicated mouse is indicative of the ability of the drug or agent to treat schizophrenia or a disease or disorder related thereto.

In addition, the present invention extends to a method for identifying a drug or agent for use in treating schizophrenia or a disease or disorder related thereto, comprising the steps of:

a) administering the drug or agent to a mouse having within its genome two copies of an isolated variant allele of a Prodh gene comprising a DNA sequence of SEQ ID NO:7, wherein both copies are capable of expressing a mutant Prodh comprising an amino acid sequence of SEQ ID NO:8;

b) performing a PPI test on the mouse to obtain a percentage of inhibition of the startle response in the mouse; and c) comparing the percentage of inhibition of the startle response in the mouse with the percentage of inhibition of the startle response in an unmedicated mouse having within its genome two copies of an isolated Prodh gene comprising a DNA sequence of SEQ ID NO:3, wherein both copies are capable of expressing a Prodh comprising an amino acid sequence of SEQ ID NO:4.

If the percentage of inhibition of the startle response in the medicated mouse is statistically equivalent to the percentage of inhibition in the mouse capable of expressing Prodh comprising a DNA sequence of SEQ ID NO:4, then the drug or agent has the ability to treat schizophrenia or a disease or disorder related thereto.

In another embodiment, the present invention extends to an a method for identifying a drug or agent for use in treating schizophrenia or a disease or disorder related thereto, comprising the steps of:

a) administering the drug or agent to an F3 generation mouse from a cross of Pro/Re X C57B1/6J wild-type, wherein the F3 generation mouse has two copies within its genome of an isolated variant allele of a Prodh gene comprising a DNA sequence of SEQ ID NO:7 which are capable of expressing a mutant Prodh comprising an amino acid sequence of SEQ ID NO:8;

b) performing a PPI test on the F3 generation mouse from a cross of Pro/Re X C57B1/6J wild-type administered the drug or agent to obtain a percentage of inhibition of the startle response in the mouse; and c) comparing the percentage of inhibition of the startle response in F3 generation mouse from a cross of Pro/Re X C57B1/6J wild-type administered the drug with the percentage of inhibition of the startle response in an F3 generation mouse from a cross of Pro/Re X C57B1/6J wild-type, wherein the F3 generation mouse has two copies within its genome of an isolated Prodh gene comprising a DNA sequence of SEQ ID NO:3 which are capable of expressing a Prodh comprising an amino acid sequence of SEQ ID NO:4.

If the percentage of inhibition of the startle response in the medicated mouse is statistically equivalent to the percentage of inhibition in the mouse capable of expressing Prodh comprising a DNA sequence of SEQ ID NO:4, then the drug or agent has the ability to treat schizophrenia or a disease or disorder related thereto.

The PPI test is described infra.

Accordingly it is an object of the invention to provide the DNA sequences of murine and human proline dehydrogenase genes, and the amino acid sequences of murine and human proline dehydrogenase.

It is another object of the present invention to provide heretofore unknown variant alleles of the human PRODH gene, which can be used to map the locus of the human PRODH gene.

It is another object of the invention to provide a heretofore unknown variant allele of the human PODH gene which is a marker for a susceptibility to, or the presence of schizophrenia or a disease or disorder related thereto in a subject, such as obsessive compulsive disorder (OCD), bipolar disorder (BP) or major depressive disorder in a subject.

It is yet another object of the present invention to provide isolated nucleic acid molecules, optionally detectably labeled, which are hybridizable under standard hybridization conditions to variant alleles of the PRODH gene disclosed herein.

It is yet another object of the present invention to provide variant PRODH proteins, produced from the expression of a variant alleles of the human PRODH gene, or isolated nucleic acid molecules hybridizable to such variant alleles under standard hybridization conditions.

It is yet another object of the present invention to provide antibodies, optionally detectably labeled, having a variant PRODH protein of the present invention as an immunogen, wherein such antibodies may be polyclonal, monoclonal or chimeric.

It is yet another object of the present invention to provide commercial test kits for attending medical professionals to determine the presence of a variant allele of the PRODH gene in a bodily sample taken from a subject. The results of such testing can then be used to determine the subject's susceptibility to suffer from schizophrenia or a disease or disorder related thereto, such as obsessive compulsive disorder (OCD), bipolar disorder (BP) or major depressive disorder, or to diagnose such a disease or disorder.

It is yet another object of the present invention to provide a method and associated assay system for screening subjects in order to determine their susceptibility to schizophrenia or a disease or disorder related thereto, and to likewise select an appropriate course of therapy therefor.

It is yet another object of the present invention to provide compositions such as drugs, agents and the like, potentially effective in either potentiating the effects of PRODH, or increasing levels of PRODH in mammalian, especially human patients.

It is still yet another object of the present invention to provide a method for the treatment of mammals to modulate the amount or activity of PRODH or subunits thereof in the mammal, so as to alter the adverse consequences of diminished levels of PRODH, which can result in schizophrenia or a disease or disorder related thereto, such as obsessive compulsive disorder (OCD), bipolar disorder (BP) or major depressive disorder.

It is a still yet another object of the present invention to provide pharmaceutical compositions for use in therapeutic methods which comprise or are based upon the PRODH, its subunits, their binding partner(s), as well as molecules whose activity or production depends on PRODH; or upon molecules or agents or drugs that control the production, stability and degradation, or that mimic the activities of the PRODH.

It is yet still another object of the present invention to provide methods of determining a susceptibility for, or presence of, schizophrenia, or a disease or disorder related thereto, by determining the levels of an enzyme involved in proline catabolism, wherein such an enzyme comprises PRODH.

It is yet still another object of the present invention to provide numerous methods for the selection of a drug or therapeutic agent to treat potentially schizophrenia, or a disease or disorder related thereto, such as obsessive compulsive disorder (OCD), bipolar disorder (BP) or major depressive disorder.

It is yet still another object of the invention to provide the DNA sequence of the wild-type murine Prodh gene, and an isolated variant of the allele of the wild-type murine Prodh gene.

It is yet still another object of the invention to provide the amino acid sequence of wild-type murine Prodh protein, as well as a mutant murine Prodh protein.

It is yet still another object of the invention to provide mammalian assays for determining whether a drug or agent has the ability to treat schizophrenia or a disease or disorder related thereto. Such assays involve Pro/Re mice described in the Example, and the PPI test, described below.

These and other aspects of the present invention will be better appreciated by reference to the following drawings and Detailed Description.

BRIEF DESCRIPTION OF THE DRAWINGS

FIG. 6 shows the human PRODH cDNA sequence (SEQ ID NO:1). Underlined nucleotides 1–3 make up the first codon of the sequence, and underlined nucleotides 1549–1551 make up the termination codon.

FIG. 7 shows the amino acid sequence of human proline dehydrogenase (SEQ ID NO:2).

FIG. 8 shows the murine Prodh cDNA sequence (SEQ ID NO:3).

FIG. 9 shows the amino acid sequence of murine proline dehydrogenase (SEQ ID NO:4).

FIG. 10 shows the DNA sequence of a variant allele of the murine Prodh gene (SEQ ID NO:7).

FIG. 11 shows the amino acid sequence of mutant murine Prodh protein (SEQ ID NO:8).

FIG. 12 shows the DNA sequence of an isolated nucleic acid molecule of the invention which encodes human proline dehydrogenase (SEQ ID NO:9). Underlined nucleotides 447–449 make up the first codon, and underlined nucleotides 1995–1997 make up the termination codon.

DETAILED DESCRIPTION OF THE INVENTION

Figure 1B:
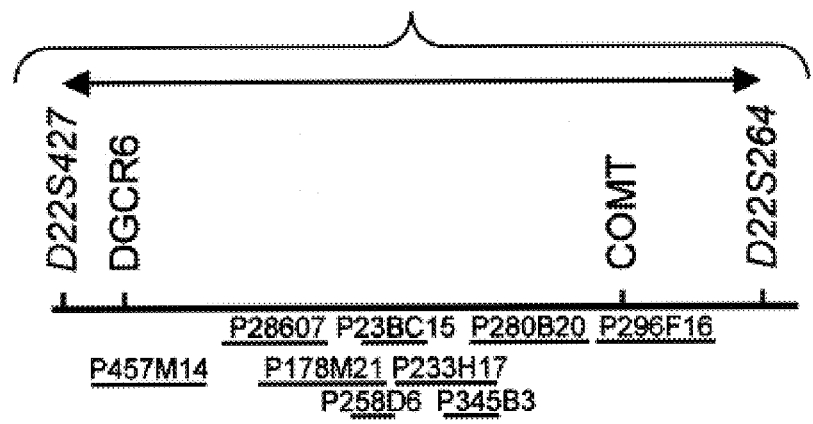
FIG. 1: (A) Multiple alignment of the predicted protein sequences of *H. sapiens, M. musculus, D. melanogaster* and *S. cerevisiae* proline dehydrogenase. Shaded areas highlight identities. Also, an asterisk (*) indicates a mutation in murine Prodh. (B) Localization of the human proline dehydrogenase gene to chromosome 22q11: Southern blot hybridization analysis of an array of nine PACs mapped and ordered within the 22q11 microdeletion [Carlson et al., 1997]. A human PRODH cDNA fragment was used as a hybridization probe. Only PAC-P457M14 (*) provided a positive signal. The positions of the COMT and DGCR6 genes, previously mapped in this region [M. H. Grossman, B. S. Emanuel, M. L. Budarf, *Genomics* 12, 822 (1992); S. Demczuk, G. Thomas, A. Aurias, *Hum. Mol. Genet.* 5, 633 (1996)] are indicated as reference points. Markers D22S427 and D22S264, that flank the smallest 22q11 deletion associated with schizophrenia as presented in [Karayiorgou et al., 1995], are also indicated. (C) High resolution Northern blot analysis of the brain expression pattern of human PRODH (human brain mRNA filter was purchased from Clontech (Palo Alto, Calif.)); hybridization to a human β-actin probe was used to confirm equal loading of undegraded mRNA in each lane.
Figure 1B:
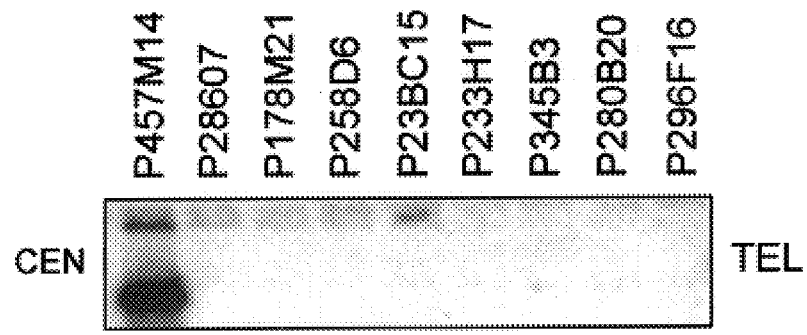

As explained above, the present invention is based upon the discovery of the DNA sequences of human PRODH and murine Prodh, a heretofore unknown variant of murine Prodh which encodes a mutant Prodh protein, and heretofore unknown variant alleles of the PRODH gene, that encode heretofore unknown variant human proline dehydrogenase (PRODH) proteins.

In addition, the present invention is based upon Applicants' discovery that unexpectedly, a correlation exists between the presence of schizophrenic symptoms in a subject, and the presence of a variant allele of the PRODH gene in the subject's genome. Hence, a variant allele of human PRODH can serve as a genetic marker to determine a susceptibility to, or presence of schizophrenia or a disease or disorder related thereto, such as obsessive compulsive disorder (OCD), bipolar disorder (BP) or major depressive disorder (MDD) in a subject.

Furthermore, the present invention extends to diagnostic methods to determine a subject's increased or decreased susceptibility to schizophrenia or a disease or disorder related thereto. With the results of such methods, targeted prevention methods, early therapeutic intervention, and improved chronic treatment for schizophrenia or a disease or disorder related thereto are set forth herein and encompassed by the present invention. In addition, attending medical professionals armed with the results of such diagnostic methods can determine an appropriate regimen to treat the subject.

What's more, the present invention extends to assays to determine the ability of a drug or agent can be used to treat schizophrenia or a disease or disorder related thereto.

Numerous terms and phrases are used throughout the instant Application and are defined below:

As used herein "PRODH" refers to a wild type human proline dehydrogenase gene, and "PRODH" refers to a wild-type human proline dehydrogenase protein. An example of the PRODH gene comprises a DNA sequence of SEQ ID NO:1. Another example comprises the DNA sequence of SEQ ID NO:9.

As used herein, the phrase "isolated variant allele of a human proline dehydrogenase (PRODH) gene" refers to an assembly of nucleotides that includes cDNA and genomic DNA nucleic acids, which is a mutational state of the wild-type PRODH gene.

As used herein, an "isolated human variant proline dehydrogenase" or a "variant PRODH" refer to a protein which is a mutational state of the wild type proline PRODH.

As used herein, "Prodh" refers to a wild-type murine proline dehydrogenase gene, and "Prodh" refers to a wild-type murine proline dehydrogenase protein.

As used herein, the phrase "isolated variant allele of murine Prodh gene" refers to an assembly of nucleotides that includes cDNA and genomic DNA nucleic acids, which is a mutational state of the wild-type Prodh gene. A particular example of an isolated variant allele of the murine Prodh gene comprises a DNA sequence of FIG. 10 (SEQ ID NO:7).

As used herein, the phrase "mutant Prodh protein" or "variant Prodh" refers to a protein encoded by an isolated variant allele of murine Prodh gene, which has an amino acid sequence that is different from the amino acid sequence of wild-type murine Prodh protein. A particular example of wild-type murine Prodh protein comprises an amino acid sequence of FIG. 9 (SEQ ID NO:4), while a mutant murine Prodh protein comprises an amino acid sequence of FIG. 11 (SEQ ID NO:8). A comparison of these two sequences shows that the mutant murine Prodh has an amino acid sequence different from that of Prodh.

As used herein, the term "transition" refers to a mutational event in which one purine is replaced by another, or one pyrimidine is replaced by another.

As used herein, the term "codon" refers to a triplet of bases in a DNA or RNA molecule that specifies or encodes the information for a single amino acid.

As used herein, the phrase "F3 generation mouse from a cross of Pro/Re X C57B1/6J wild-type, wherein the F3 generation mouse has two copies within its genome of an isolated variant allele of a Prodh gene comprising a DNA sequence of SEQ ID NO:7 which are capable of expressing a mutant Prodh comprising an amino acid sequence of SEQ ID NO:8" refers to the third generation mouse of a line of mice formed from a cross between the Pro/Re strain of mice and the wild-type C57BL/6J wild-type strain, wherein the mouse is homozygous for the variant allele of Prodh comprising the DNA sequence of SEQ ID NO:7, and expresses the variant Prodh comprising a DNA sequence of SEQ ID NO:8.

As used herein, the phrase "F3 generation mouse from a cross of Pro/Re X C57B1/6J wild-type, wherein the F3 generation mouse has two copies within its genome of an isolated Prodh gene comprising a DNA sequence of SEQ ID NO:3 which are capable of expressing a Prodh comprising an amino acid sequence of SEQ ID NO:4" refers to the third generation mouse of a line of mice formed from a cross between the Pro/Re strain of mice and the wild-type C57BL/6J wild-type strain, wherein the mouse is homozygous for the Prodh gene comprising the DNA sequence of SEQ ID NO:3, and expresses Prodh comprising a DNA sequence of SEQ ID NO:4.

As used herein, the terms "schizophrenia", "obsessive compulsive disorder", "bipolar disorder", and "major depressive disorder" refer to psychiatric diseases or disorders that are readily understood by the skilled artisan and are set forth in American Psychiatric Associate (1994): *Diagnostic and Statistical Manual of Mental Disorders*, 4$^{th}$ Edition. Washington, D.C.

As used herein, the term "susceptibility" to schizophrenia or a disease or disorder related thereto refers to a subject's potential of being affected with such a disease or disorder.

As used herein, the terms "standard" and "control" refer to a bodily sample, cell extract, etc. established for use as a rule or basis of comparison in measuring levels of activity of PRODH, results of PPI, etc.

As used herein, the term "combination" referring to variations in the wild-type sequence, either amino acid residues or nucleotides, indicates that two or more of the discovered variations in the particular DNA sequence of amino acid sequence can be present in variant allele of the wild-type nucleic acid molecule or protein.

An initial aspect of the invention extends to an isolated nucleic acid molecule comprising a DNA sequence of SEQ ID NO:1, degenerate variants thereof, fragments thereof, or analogs or derivatives thereof.

Another aspect of the invention extends to an isolated nucleic acid molecule comprising a DNA sequence of SEQ ID NO:3, degenerate variants thereof, fragments thereof, or analogs or derivatives thereof.

Another aspect of the present invention extends an isolated variant allele of the PRODH gene, wherein the PRODH gene comprises a DNA sequence of SEQ ID NO:1 or SEQ ID NO:9, and an isolated variant allele of the PRODH comprises a DNA sequence having at least one variation in SEQ ID NO:1 or SEQ ID NO:9, wherein the at least one variation comprises:

a G to A transition in the third position of codon 83;
a C to T transition in the first position of codon 101;
a G to A transition in the second position of codon 101;
a C to T transition in the first position of codon 247;
a C to T transition in the third position of codon 342;
a C to T transition in the third position of codon 421;
an A to G transition in the second position of codon 437;
a T to C transition in the first position of codon 497; or
a combination thereof.

Furthermore, the present invention is based on discovery that surprisingly and unexpectedly, a particular variant allele of the PRODH gene is present in a statistically significantly higher frequency in subjects suffering from a psychiatric disease or disorder. Further explanation of this aspect of the invention is set forth infra.

Consequently, an initial aspect of the present invention contemplates isolation of PRODH, Prodh, and heretofore unknown variant alleles of the human PRODH gene. As used herein, the term "gene" refers to an assembly of nucleotides that encode a polypeptide, and includes cDNA and genomic DNA nucleic acids.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

"Heterologous" DNA refers to DNA not naturally located in the cell, or in a chromosomal site of the cell. Preferably, the heterologous DNA includes a gene foreign to the cell.

As used herein, the term "wild-type" refers to the most commonly observed phenotype or genotype, designated as the norm.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded form comprising coding and complementary strands. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule, e.g. either the coding strand or the strand complementary to the coding strand, can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 50°, canbe used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., a $T_m$ of 55° C., 40% formamide, with 5× or 6×SSC. High stringency hybridization conditions correspond to the highest $T_m$, e.g., a $T_m$ of 60–65° C., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; particularly at least about 15 nucleotides; more particularly at least about 20 nucleotides; even more particularly at least about 30 nucleotides, and yet more particularly at least about 40 nucleotides, and most particularly about 50 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" or "promoter" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A coding sequence is "operatively associated with" a transcriptional and translational control sequences, such as a promoter for example, when RNA polymerase transcribes the coding sequence into mRNA, which in turn is translated into a protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

The term "oligonucleotide" as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–50 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

A "clone" is a population of cells derived from a single cell or common ancestor by mitosis. A "cell line" is a clone of a primary cell that is capable of stable growth in vitro for many generations.

As used herein, the phrase "an isolated nucleic acid molecule of the invention" refers to any of the following:

a) an isolated nucleic acid molecule comprising a DNA sequence of SEQ ID NO:1, degenerate variants thereof, fragments thereof, or analogs or derivatives thereof;

b) an isolated nucleic acid hybridizable under standard hybridization conditions to an isolated nucleic acid molecule comprising a DNA sequence of SEQ ID NO:1, degenerate variants thereof, fragments thereof, or analogs or derivatives thereof;

c) an isolated nucleic acid molecule comprising a DNA sequence of SEQ ID NO:3, degenerate variants thereof, fragments thereof, or analogs or derivatives thereof;

d) an isolated nucleic acid molecule hybridizable under standard hybridization conditions to an isolated nucleic acid molecule comprising a DNA sequence of SEQ ID NO:3, degenerate variants thereof, fragments thereof, or analogs or derivatives thereof;

e) an isolated variant allele of a PRODH gene, wherein the isolated variant allele comprises a DNA sequence having at least one variation in SEQ ID NO:1, wherein the at least one variation comprises:
  a G to A transition in the third position of codon 83;
  a C to T transition in the first position of codon 101;
  a G to A transition in the second position of codon 101;
  a C to T transition in the first position of codon 247;
  a C to T transition in the third position of codon 342;
  a C to T transition in the third position of codon 421;
  an A to G transition in the second position of codon 437;
  a T to C transition in the first position of codon 497; or
  a combination thereof along with degenerate variants thereof, fragments thereof, or analogs or derivatives thereof;

f) an isolated nucleic acid molecule hybridizable under standard hybridization conditions to an isolated variant allele of the PRODH gene, degenerate variants thereof, fragments thereof, or analogs or derivatives thereof;

g) an isolated variant of a murine Prodh gene comprising a DNA sequence of SEQ ID NO:7, degenerate variants thereof, fragments thereof, or analogs or derivatives thereof;

h) an isolated nucleic acid molecule hybridizable under standard hybridization conditions to an isolated nucleic acid molecule comprising the DNA sequence of SEQ ID NO:7, degenerate variants thereof fragments thereof, or analogs or derivatives thereof;

i) an isolated nucleic acid molecule comprising a DNA sequence of SEQ ID NO:9, degenerate variants thereof, fragments thereof, or analogs or derivatives thereof; and j) an isolated nucleic acid molecule hybridizable under standard hybridization conditions to an isolated nucleic acid molecule comprising a DNA sequence of SEQ ID NO:9, degenerate variants thereof, fragments thereof, or analogs or derivatives thereof.

As used herein, an "isolated protein of the invention" refers to any of the following:

a) an isolated protein comprising an amino acid sequence of SEQ ID NO:2, conservative variants thereof, fragments thereof, or analogs or derivatives thereof;

b) an isolated protein comprising an amino sequence of SEQ ID NO:4, conservative variants thereof, fragments thereof, or analogs or derivatives thereof; and c) an isolated protein comprising an amino acid sequence having at least one variation in SEQ ID NO:2, wherein the at least one variation comprises:

Arg101Trp;

Arg101Glu;

Glu437Arg; or a combination thereof;

d) an isolated mutant variant proline dehydrogenase (Prodh) comprising an amino acid sequence of SEQ ID NO:8, conservative variants thereof, fragments thereof, or analogs or derivatives thereof.

Degenerate Variants of an Isolated Nucleic Acid Molecule of the Invention, and Conservative Variants of an Isolated Protein of the Invention Due to the degenerate nature of codons in the genetic code, an isolated protein of the invention can be encoded by nucleic acid molecules other than an isolated nucleic acid molecule of the invention. "Degenerate nature" refers to the use of different three-letter codons to specify a particular amino acid pursuant to the genetic code. It is well known in the art that the following codons can be used interchangeably to code for each specific amino acid:

Phenylalanine (Phe or F)
UUU or UUC
Leucine (Leu or L)
UUA or UUG or CUU or CUC or CUA or CUG
Isoleucine (Ile or I)
AUU or AUC or AUA
Methionine (Met or M)
AUG
Valine (Val or V)
GUU or GUC of GUA or GUG
Serine (Ser or S)
UCU or UCC or UCA or UCG or AGU or AGC
Proline (Pro or P)
CCU or CCC or CCA or CCG
Threonine (Thr or T)
ACU or ACC or ACA or ACG
Alanine (Ala or A)
GCU or GCG or GCA or GCG
Tyrosine (Tyr or Y)
UAU or UAC
Histidine (His or H)
CAU or CAC
Glutamine (Gin or Q)
CAA or CAG
Asparagine (Asn or N)
AAU or AAC
Lysine (Lys or K)
AAA or AAG
Aspartic Acid (Asp or D)
GAU or GAC
Glutamic Acid (Glu or E)
GAA or GAG
Cysteine (Cys or C)
UGU or UGC
Arginine (Arg or R)
CGU or CGC or CGA or CGG or AGA or AGG
Glycine (Gly or G)
GGU or GGC or GGA or GGG
Tryptophan (Trp or W)
UGG
Termination codon
UAA (ochre) or UAG (amber) or UGA (opal)

It should be understood that the codons specified above are for RNA sequences. The corresponding codons for DNA have a T substituted for U.

Likewise, conservative isolated variants of an PRODH protein of the present invention include, but are not limited to, those containing, as a primary amino acid sequence, substitutions of amino acid residues in the amino acid sequences of SEQ ID NO:2, as well as in a variant PRODH protein of the invention having an amino acid sequence as described above, a murine Prodh comprising an amino acid sequence of SEQ ID NO:4, and a mutant murine Prodh comprising an amino acid sequence of SEQ ID NO:8, wherein the substituted amino acids are functionally equivalent to the amino acid residues for which they substitute. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid residue belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure. As a result of such substitutions, "conservative variants" of an amino acid sequence of the invention are formed.

Fragments of Isolated Nucleic Acid Molecules and Isolated Proteins of the Invention Further, as used herein, a "fragment" of an isolated nucleic acid molecule of the invention is defined as an isolated nucleic acid molecule comprising at least 10 contiguous nucleotides, particularly at least 20 contiguous nucleotides, more particularly at least 30 contiguous nucleotides, and even more particularly at least 40 contiguous nucleotides of an isolated nucleic acid molecule of the invention, in the same 5'-3' order the contiguous nucleotides appear in the isolated nucleic acid molecule of the invention. Fragments of an isolated nucleic acid molecule of the invention can readily be prepared by digesting an isolated nucleic acid molecule of the invention with a restriction endonuclease. Alternatively, one may use DNAse in the presence of manganese to fragment the DNA, or the DNA can be physically sheared, as for example, by sonication. The DNA fragments of an isolated nucleic acid molecule of the invention can then be separated according to size by standard techniques, including but not limited to, agarose and polyacrylamide gel electrophoresis and column chromatography. Once fragments of the isolated nucleic acid molecule have themselves been separated, they can be readily inserted the fragments into expression vectors. As a result, the peptides and polypeptides, which are themselves fragments of an isolated protein of the invention can readily be produced by one of ordinary skill in the art.

Likewise, a "fragment" of protein of the invention comprises at least 10 contiguous amino acid residues, particularly at least 15 contiguous amino acid residues, even more particularly at least 20 contiguous amino acid residues, and most particularly at least 25 contiguous amino acid residues of a protein of the invention, in the N terminus to C terminus order in which the contiguous residues occur in the protein of the invention. One of ordinary skill in the art can readily prepare such fragments using recombinant DNA techniques with fragments of isolated nucleic acid molecules of the invention, by digesting a protein of the invention with a protease, chemically cleaving a protein of the invention with chemical reagents such as CNBr, or synthesizing the fragment using routine solid support methods as taught by Merrifield.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program using default parameters.

The term "corresponding to" is used herein to refer to similar or homologous sequences, whether the exact position is identical or different from the molecule to which the similarity or homology is measured. Thus, the term "corresponding to" refers to the sequence similarity, and not the numbering of the amino acid residues or nucleotide bases.

A variant allele of the human PRODH gene, whether genomic DNA or cDNA, can be isolated from any source, particularly from a human cDNA or genomic library. Likewise, a variant allele of Prodh, whether genomic or cDNA can be isolated from any source, particularly from a murine cDNA or genomic library. Methods for obtaining a variant allele of a PRODH gene or a Prodh gene are well known in the art, as described above (see, e.g., Sambrook et al., 1989, supra).

The DNA may be obtained by standard procedures known in the art from cloned DNA (e.g., a DNA "library"), and preferably is obtained from a cDNA library prepared from tissues with high level expression of a PRODH protein, an isolated variant thereof, or Prodh or an isolated variant thereof, by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, an isolated nucleic acid molecule of the invention can be molecularly cloned into a suitable vector for propagation.

Once the DNA fragments are generated, identification of a specific DNA fragment comprising an isolated nucleic acid molecule of the invention may be accomplished in a number of ways. For example, if an amount of a portion of an isolated nucleic acid molecule is available and can be purified and labeled, the generated DNA fragments may be screened by nucleic acid hybridization to a labeled probe (Benton and Davis, 1977, Science 196:180; Grunstein and Hogness, 1975, Proc. Natl. Acad. Sci. U.S.A. 72:3961). For example, a set of oligonucleotides corresponding to the partial amino acid sequence information obtained SEQ ID NO:2 or a variant human PRODH protein, SEQ ID NO:4, or SEQ ID NO:8 of the present invention can be prepared and used as probes for an isolated nucleic acid molecule of the invention, as was done in a specific example, infra, or as primers for cDNA or mRNA (e.g., in combination with a poly-T primer for RT-PCR). Preferably, a fragment is selected that is highly unique to an isolated nucleic acid molecule of the invention. Those DNA fragments with substantial homology to the probe will hybridize. As noted above, the greater the degree of homology, the more stringent hybridization conditions can be used.

Further selection can be carried out on the basis of the properties the protein produced from expression of an isolated nucleic acid molecule of the invention. For example, an isolated variant allele of a PRODH gene of the present invention can be isolated if it encodes a variant PRODH protein having an isoelectric, electrophoretic, amino acid composition, or partial amino acid sequence different from PRODH produced from the expression of the PRODH gene (SEQ ID NO:1) herein. Thus, the presence of a variant allele of a PRODH gene of the present invention may be detected by assays based on the physical, chemical, or immunological properties of its expressed product. For example, cDNA clones, or DNA clones which hybrid-select the proper mRNAs, can be selected which produce a protein that, e.g., has different electrophoretic migration, isoelectric focusing or non-equilibrium pH gel electrophoresis behavior, proteolytic digestion maps, or antigenic properties as are known for a PRODH protein comprising an amino acid sequence of SEQ ID NO:2. Such selection can also be made between Prodh and an isolated variant of Prodh.

An isolated variant allele of a PRODH gene of the present invention, for example, can also be identified by mRNA selection, i.e., by nucleic acid hybridization followed by in vitro translation. In this procedure, nucleotide fragments are used to isolate complementary mRNAs by hybridization. Such DNA fragments may represent available, purified DNA of an isolated variant allele of a human PRODH gene of the present invention, or may be synthetic oligonucleotides designed from the partial amino acid sequence information.

Immunoprecipitation analysis or functional assays of the in vitro translation products of the products of the isolated mRNAs identifies the mRNA and, therefore, the complementary DNA fragments, that contain the desired sequences. Naturally, these techniques can also be used to identify isolated variant of Prodh.

Furthermore, a detectably labeled isolated nucleic acid molecule of the present invention can be prepared by one of ordinary skill in the art. Once detectably labeled, an isolated nucleic acid molecule of the invention degenerate variants thereof, fragments thereof, or analogs or derivatives thereof, can then be used as a probe to identify homologous DNA fragments from among other genomic DNA fragments. Suitable labels include enzymes, radioactive isotopes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one of labels which can be used according to the present invention. A direct label has been defined as an entity, which in its natural state, is readily visible, either to the naked eye, or with the aid of an optical filter and/or applied stimulation, e.g. U.V. light to promote fluorescence. Examples of colored labels, which can be used according to the present invention include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, and urease. These and others have been discussed in detail by Eva Engvall in Enzyme Immunoassay ELISA and EMIT in *Methods in Enzymology*, 70. 419–439, 1980 and in U.S. Pat. No. 4,857,453.

Other labels for use in the invention include magnetic beads or magnetic resonance imaging labels.

Clonging Vectors

As explained above, the present invention extends to various cloning vectors. In particular, the present invention extends to a cloning vector comprising an isolated nucleic acid molecule of the invention and an origin of replication.

A large number of vector-host systems known in the art may be used to clone an isolated nucleic acid molecule of the invention. Possible vectors include, but are not limited to, plasmids or modified viruses. The vector system used however must be compatible with the host cell. Examples of vectors that are commercially available and have applications herein include, but are not limited to, *E. coli,* bacteriophages such as lambda derivatives, or plasmids such as pBR322 derivatives or pUC plasmid derivatives, e.g., pGEX vectors, pmal-c, pFLAG, etc. Furthermore, insertion of an isolated nucleic acid molecule of the invention as described above into a cloning vector can be readily accomplished by one of ordinary skill in the art. For example, insertion can be accomplished by ligating an isolated nucleic acid molecule of the invention into a cloning vector which has complementary cohesive termini. However, if the complementary restriction sites used to fragment the isolated nucleic acid molecule of the invention, to form a cassette are not present in the cloning vector, the ends of the cassette may be enzymatically modified using procedures well known to one of ordinary skill in the art. Once modified, the cassette can be readily ligated into a commercially available cloning vector. Alternatively, any site desired may be produced by ligating nucleotide sequences (linkers) onto the DNA termini of the cassette; these ligated linkers may comprise specific chemically synthesized oligonucleotides encoding restriction endonuclease recognition sequences.

Once an isolated nucleic acid molecule of the invention is inserted into a vector, the vector can then be introduced into host cells via transformation, transfection, infection, electroporation, etc., so that many copies of the isolated nucleic acid molecule of the invention can be generated. Preferably, the cloned isolated variant allele or isolated nucleic acid molecule hybridizable thereto under standard hybridization conditions is contained on a shuttle vector plasmid, which provides for expansion in a cloning cell, e.g., *E. coli,* and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2 $\mu$plasmid.

In an alternative method, an isolated nucleic acid molecule of the invention may be identified and isolated after insertion into a suitable cloning vector in a "shot gun" approach. Enrichment for an isolated variant allele, for example, by size fractionation, can be done before insertion into the cloning vector.

Expression Vectors

An isolated nucleic acid molecule of the inventioin can be inserted into an appropriate expression vector, i.e., a vector which contains the necessary elements for the transcription and translation of the inserted protein-coding sequence such that the protein-coding sequence is operatively associated with a promoter. A DNA sequence is "operatively associated" to an expression control sequence, such as a promoter, when the expression control sequence controls and regulates the transcription and translation of that DNA sequence. The term "operatively associated" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If an isolated nucleic acid molecule of the invention does not contain an appropriate start signal, such a start signal can be readily inserted into the expression vector in front of (5' of) protein encoding nucleic acid molecule inserted into the expression vector using methods readily understood and available to one of ordinary skill in the art.

Both cDNA and genomic sequences can be cloned and expressed under control of such regulatory sequences. An expression vector also preferably includes a replication origin.

The necessary transcriptional and translational signals can be provided on a recombinant expression vector, or they may be supplied by an isolated nucleic acid molecule of the invention inserted into an expression vector.

Potential host-vector systems which are commercially available and have ready applications herein include, but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

An isolated nucleic acid molecule of the invention may be expressed chromosomally, after integration of the coding sequence by recombination. In this regard, any of a number of amplification systems may be used to achieve high levels of stable gene expression (See Sambrook et al., 1989, supra).

A unicellular host transformed or transfected with an expression vector of the invention can be cultured in an appropriate cell culture medium that provides for expression of an isolated nucleic acid molecule of the invention inserted into an expression vector and operatively associated with a promoter.

Any of the methods previously described for the insertion of DNA fragments into a cloning vector may be used to construct expression vectors of the present invention. These methods may include in vitro recombinant DNA and synthetic techniques and in vivo recombination (genetic recombination).

Expression of an isolated nucleic acid molecule of the invention to produce a protein of the invention may be controlled by any promoter/enhancer element known in the art. However, these regulatory elements must be functional in the host selected for expression. Promoters which may be used to control expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Moreover, an expression vector can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, an isolated nucleic acid molecule of the invention can be amplified by PCR to provide for detection of the amplified product. In the second approach, the presence of a foreign gene inserted in an expression vector of the present invention can be detected by nucleic acid hybridization using probes comprising sequences that are homologous to an inserted marker gene. In the third approach, the recombinant vector/host system can be identified and selected based upon the presence or absence of certain "selection marker" gene functions (e.g., P-galactosidase activity, thymidine kinase activity, resistance to antibiotics, transformation phenotype, occlusion body formation in baculovirus, etc.) caused by the insertion of foreign genes in the vector. In yet another example, if, an isolated nucleic acid molecule of the invention is inserted within the "selection marker" gene sequence of the vector, recombinants containing the insert can be identified by the absence of the inserted gene function. In the fourth approach, recombinant expression vectors can be identified by assaying for the activity, biochemical, or immunological characteristics of the gene product expressed by the recombinant expression vector, provided that the expressed protein assumes a functionally active conformation.

Naturally, the present invention extends to a method of producing an isolated protein of the invention. An example of such a method comprises the steps of culturing a unicellular host transformed or transfected with an expression vector of the invention under conditions that provide for expression of the isolated nucleic acid molecule of the invention inserted into the expression vector, to produce a protein of the invention. The protein produced depends upon which isolated nucleic acid molecule of the invention was inserted into the expression vector. The isolated protein produced can then be readily recovered from the unicellular host, the culture, or both.

A wide variety of unicellular host/expression vector combinations commercially available to the skilled artisan may be employed in producing an isolated protein of the invention.

Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMal-C2, pET, pGEX (Smith et al., 1988, Gene 67:31–40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED PstI, SalI, SbaI, SmaI, and EcoRI cloning site, with the vector expressing both the cloned gene and DHFR; see Kaufman, *Current Protocols in Molecular Biology*, 16.12 (1991).

Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible metallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SnaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention include the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Furthermore, once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Examples of unicellular hosts contemplated by the present invention, which are well know to those of ordinary skill in the art, include but are not limited to, *E. coli* Pseudonomas, Bacillus, Strepomyces, yeast, CHO, R1.1, B-W, L-M, COS1, COS7, BSC1, BSC40, BMT10, or HeLa cells, all of which are readily available to the skilled artisan. In addition, a host cell strain may be chosen which modulates the expression of an isolated nucleic acid molecule of the invention modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, a translocation signal sequence of the product produced from expression of an isolated nucleic acid molecule of the invention in bacteria may not be properly spliced. Expression in yeast can produce a glycosylated product. Expression in eukaryotic cells can increase the likelihood of "native" glycosylation and folding. Moreover, expression in mammalian cells can provide a tool for reconstituting, or constituting activity of murine proline dehydrogenase, human PRODH, or a variant human PRODH protein of the invention. Furthermore, different vector/host expression systems may affect processing reactions, such as proteolytic cleavages, to a different extent.

Vectors are introduced into the desired unicellular hosts by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Antibodies to an Isolated Protein of the Invention

According to the invention, an isolated protein of the invention may be used as an immunogen to generate antibodies. Such antibodies include but are not limited to polyclonal, monoclonal, chimeric, single chain, Fab fragments, and an Fab expression library. Furthermore, antibodies of the invention may be cross reactive, e.g., they may recognize more than one isolated protein of the invention.

Various procedures known in the art may be used for the production of polyclonal antibodies of the invention. For the production of antibody, various host animals can be immunized by injection with an immunogen described above. Examples of such animals include, but are not limited to rabbits, mice, rats, sheep, goats, etc. In one embodiment, an isolated protein of the invention can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies of the invention, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing technology set forth in PCT/US90/02545. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse which encode an antibody molecule specific for a protein of the invention together with genes from a human antibody molecule of appropriate biological activity can be used, and are within the scope of this invention. Such human or humanized chimeric antibodies are preferred for use in determining the presence of an isolated protein of the invention in a sample.

According to the invention, techniques described for the production of single chain antibodies [U.S. Pat. Nos. 5,476,786 and 5,132,405 to Huston; U.S. Pat. No. 4,946,778] can be adapted to produce particular isolated variant human PRODH protein-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for an isolated protein of the invention.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an isolated protein of the invention, one may assay generated hybridomas for a product which binds to a fragment of a variant PRODH protein containing such epitope.

The foregoing antibodies can be used in methods known in the art relating to the localization and activity of an isolated variant human PRODH protein, conservative variants thereof, or fragments thereof e.g., for Western blotting, imaging a variant human PRODH protein in situ, measuring levels thereof in appropriate physiological samples, etc. using any of the detection techniques mentioned above or known in the art.

Commercial Kits

In a further embodiment, the present invention extends to commercial test kits suitable for use by a medical professional to determine the presence or absence of predetermined PRODH activity, or predetermined PRODH capability in target patient populations.

In accordance with the testing techniques discussed above, one class of such kits comprise at least the labeled PRODH or its binding partner, for instance an antibody specific thereto, and directions, of course, depending upon the method selected, e.g., "competitive," "sandwich," "DASP" and the like. The kits may also contain peripheral reagents such as buffers, stabilizers, etc. In a particular embodiment, the labeled PRODH comprises an amino acid sequence of SEQ ID NO:2.

Another class of such kits may also include PCR reagents, such as oligonucleotide primers, enzymes, gel matrixes, buffers, etc.

Accordingly, a test kit may be prepared for the diagnosis or detection of a susceptibility to schizophrenia, or a disease or disorder related thereto, to measure levels of PRODH activity in a bodily sample from a subject, wherein the kit comprises:

(a) a predetermined amount of at least one labeled immunochemically reactive component obtained by the direct or indirect attachment of the present PRODH factor or a specific binding partner thereto, to a detectable label;

(b) other reagents; and (c) directions, including comparison levels of PRODH, for use of the kit.

An alternate kit for measuring the levels of PRODH activity may comprise PCR reagents, such as oligonucleotide primers, enzymes, gel matrices, buffers, directions, including comparison levels of PRODH, for use of the kit. A still further alternate can utilize reagents for measuring the levels of PRODH activity and directions, including comparison levels of PRODH for use of the kit.

In a further variation, a test kit may be prepared and used for the purposes stated above, which operates according to a predetermined protocol (e.g. "competitive," "sandwich," "double antibody," etc.), and comprises:

(a) a labeled component which has been obtained by coupling PRODH comprising an amino acid sequence of SEQ ID NO:2, a conservative variant thereof, or fragment thereof to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between PRODH and a specific binding partner thereto.

Other kits of the present invention utilize the discovery that, unexpectedly, the presence of a particular variant allele of the PRODH gene in the genome of a subject is indicative of an increased susceptibility to schizophrenia or a disease or disorder related thereto, or a diagnosis of schizophrenia in the subject. Hence, the present invention extends to a test kit to facilitate diagnosis and treatment of schizophrenia or a disease or disorder related thereto in a eukaryotic cellular sample, wherein the test kit comprises:

a) PCR oligonucleotide primers suitable for detection of an isolated variant allele of a PRODH gene, wherein the PRODH gene comprises a DNA sequence of SEQ ID NO:1, and the variant allele comprises a DNA sequence having a variation in SEQ ID NO:1 comprising a transition of A to G in the second position of codon 437 of SEQ ID NO:1;

(b) other reagents such as enzymes, gel matrices, buffers, etc.; and (c) directions for use of the kit.

Assays for Screening the Ability Drugs and Therapeutic Agents to Treat Schizophrenia or a Disease or Disorder Related Thereto In accordance with the above, an assay system for screening potential drugs effective to modulate levels of human PRODH in a subject may be prepared. The PRODH may be introduced into a test system, such as a cell culture, and the prospective drug may also be introduced into the cell culture. The cell culture is then examined to observe any changes in the PRODH activity of the cells, due either to the addition of the prospective drug alone, or due to the effect of added quantities of the known PRODH.

Moreover, the present invention extends to an assay system for screening drugs and other agents for their ability to treat schizophrenia or a disease or disorder related thereto. Such an assay of the present invention comprises the steps of culturing an observable cellular test colony inoculated with the drug or agent to be assayed, harvesting a cellular extract from the cellular test colony, and examining the extract for the presence of PRODH. An increase or decrease in the level of activity of PRODH in the test colony compared to the level of activity of PRODH in a control colony indicates the ability of the drug to modulate the production, stability, degradation or activity of PRODH, which is indicative of the ability of the drug or agent to treat schizophrenia or a disease or disorder related thereto, such as obsessive compulsive disorder (OCD), bipolar disorder (BP) or major depressive disorder. An increase in the level of activity of PRODH in the test colony compared to level of activity in a control colony indicates the drug or agent is a potential therapeutic agent for the treatment of schizophrenia or a disease or disorder related thereto.

In another embodiment, the present invention extends to an assay system for screening drugs, agents or compounds, to determine their schizophrenic-related pharmacological activity. An example of such a method comprises the steps of:

administering the compound to a mammal;

determining the level of activity of PRODH in the mammal; and comparing the level of activity of PRODH to the level of activity of PRODH in a control animal to which the compound was not administered. An increase in the level of activity of PRODH in the mammal relative to the level of PRODH activity in the standard is indicative that the drug, agent or compound may have schizophrenic-related pharmacological activity, and ability as a therapeutic agent for treating schizophrenia or a disease or disorder related thereto, such as obsessive compulsive disorder (OCD), bipolar disorder (BP) or major depressive disorder.

Another example of an assay system for screening drugs, agents or compounds for schizophrenic related pharmacological activity comprises the steps of:

determining a basal level of activity of PRODH in a mammal;

administering the compound to the mammal;

determining the level of activity of PRODH in the mammal after administration of the compound. An increase in the level of activity of PRODH in the mammal relative to the basal level of activity indicates the compound has a schizophrenic-related pharmacological activity, and may have potential as a therapeutic agent for treating schizophrenia or a disease or disorder related thereto, such as obsessive compulsive disorder (OCD), bipolar disorder (BP), or major depressive disorder (MDD).

Methods of assaying levels of activity of PRODH are readily known to one of ordinary skill in the art, and are disclosed in Blake, R. & Russel, E., Hyperprolinemia and prolinuria in a new inbred strain of mice PRO/Re. *Science* 176, 809–811 (1972); Blake, R. L., *Animal Model for Hyperprolinaemia: Deficiency of Mouse Proline Oxidase Activity Biochem. J.* 129, 987–989 (1979) both of which are hereby incorporated by reference in their entireties.

Treating Schizophrenia or a Disease or Disorder Related Thereto

In another embodiment, the present invention extends to a method of treating schizophrenia or a disease or disorder related thereto, such as obsessive compulsive disorder (OCD), bipolar disorder (BP), or major depressive disorder (MDD) in a subject, or a symptom of such a disease or disorder. An example of such a method comprises administering to the subject a therapeutically effective amount of isolated PRODH comprising an amino acid sequence of SEQ ID NO:2, a conservative variant thereof, fragment thereof, or analog or derivative thereof.

Generally, the PRODH protein of the present invention may be derivatized by the attachment of one or more chemical moieties to the protein moiety. The chemically modified derivatives may be further formulated for intraarterial, intraperitoneal, intramuscular subcutaneous, intravenous, oral, nasal, pulmonary, topical or other routes of administration. Chemical modification of biologically active component or components may provide additional advantages under certain circumstances, such as increasing the stability and circulation time of the component or components and decreasing immunogenicity. See U.S. Pat. No. 4,179,337, Davis et al., issued Dec. 18, 1979. For a review, see Abuchowski et al., in *Enzymes as Drugs* (J. S. Holcerberg and J. Roberts, eds. pp. 367–383 (1981)). A review article describing protein modification and fusion proteins is Francis, 1992, *Focus on Growth Factors* 3:4–10, Mediscript: Mountview Court, Friern Bamet Lane, London N20, OLD, UK.

Chemical Moieties For Derivatization. The chemical moieties suitable for derivatization may be selected from among water soluble polymers. The polymer selected should be water soluble so that the component to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations. For the present component or components, these may be ascertained using the assays provided herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co- polymers, polyoxyethylated polyols and polyvinyl alcohol. Polyethylene glycol propionaldenhyde may have advantages in manufacturing due to its stability in water.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of polyethylene glycols). The proportion of polymer molecules to component or components molecules will vary, as will their concentrations in the reaction mixture. In general, the optimum ratio (in terms of efficiency of reaction in that there is no excess unreacted component or components and polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the component or components with consideration of effects on functional or antigenic domains of the protein. There are a number of attachment methods available to those skilled in the art, e.g., EP 0 401 384 herein incorporated by reference (coupling PEG to G-CSF), see also Malik et al., 1992, Exp. Hematol. 20:1028–1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group include lysine residues and the—terminal amino acid residues; those having a free carboxyl group include aspartic acid residues glutamic acid residues and the C-terminal amino acid residue. Sulfhydryl groups may also be used as a reactive group for attaching the polyethylene glycol molecule(s). Preferred for therapeutic purposes is attachment at an amino group, such as attachment at the N-terminus or lysine group.

One may specifically desire N-terminally chemically modified protein. Using polyethylene glycol as an illustration of the present compositions, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective N-terminal chemically modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively N-terminally pegylate the protein by performing the reaction at pH which allows one to take advantage of the $pK_a$ differences between the e-amino groups of the lysine residues and that of the a-amino group of the N-terminal residue of the protein. By such selective derivatization attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above, and should have a single reactive aldehyde for coupling to the protein. Polyethylene glycol proprionaldehyde, containing a single reactive aldehyde, may be used.

Pharmaceutical Compositions

In yet another aspect of the present invention, provided are pharmaceutical compositions comprising a protein comprising an amino acid sequence of SEQ ID NO:2, conservative variants thereof, fragments thereof, or analogs or derivatives thereof, and a pharmaceutically acceptable carrier thereof Such pharmaceutical compositions may be for administration for injection, or for oral, pulmonary, nasal or other forms of administration. In general, comprehended by the invention are pharmaceutical compositions comprising effective amounts of a low molecular weight component or components, or derivative products, of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435–1712 which are herein incorporated by reference. The compositions may be prepared in liquid form, or may be in dried powder, such as lyophilized form.

Oral Delivery

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the component or components (or chemically modified forms thereof) and inert ingredients which allow for protection against the stomach environment, and release of the biologically active material in the intestine.

Also specifically contemplated are oral dosage fonns of the above derivatized PRODH, conservative variant thereof, or fragment thereof. The PRODH, conservative variant thereof, or fragment thereof may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs,* Hocenberg and Roberts, eds., Wiley-Interscience, New York, N.Y., pp. 367–383; Newmark, et al., 1982, J. Appl. Biochem. 4:185–189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The herapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the protein (or derivative) are for instance the fatty acids oleic acid, linoleic acid and linolenic acid.

Controlled release oral formulation may be desirable. The drug could be incorporated into an inert matrix which permits release by either diffusion or leaching mechanisms, e.g., gums. Slowly degenerating matrices may also be incorporated into the formulation. Some enteric coatings also have a delayed release effect.

Another form of a controlled release of this therapeutic is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating may be carried out in a pan-coater or in a fluidized bed or by compression coating.

Pulmonary Delivery. Also contemplated herein is pulmonary delivery of the present protein (or derivatives thereof). The protein (or derivative) is delivered to the lungs of a mammal while inhaling and traverses across the lung epithelial lining to the blood stream. Other reports of this include Adjei et al., 1990, Pharmaceutical Research, 7:565–569; Adjei et al., 1990, International Journal of Pharmaceutics, 63:135–144 (leuprolide acetate); Braquet et al., 1989, Journal of Cardiovascular Pharmacology, 13(suppl. 5):143–146 (endothelin-1); Hubbard et al., 1989, Annals of Internal Medicine, Vol. III, pp. 206–212 (al-antitrypsin); Smith et al., 1989, J. Clin. Invest. 84:1145–1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482–3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U. S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of protein (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified protein may also be prepared in different formulations depending on the type of chemical modification or the type of device employed.

Formulations suitable for use with a nebulizer, either jet or ultrasonic, will typically comprise protein (or derivative)

dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the protein (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing protein (or derivative) and may also include a bulking agent, such as lactose, sorbitol, sucrose, or mannitol in amounts which facilitate dispersal of the powder from the device, e.g., 50 to 90% by weight of the formulation. The protein (or derivative) should most advantageously be prepared in particulate form with an average particle size of less than 10 mm (or microns), most preferably 0.5 to 5 mm, for most effective delivery to the distal lung.

Nasal Delivery. Nasal delivery of the protein (or derivative) is also contemplated. Nasal delivery allows the passage of the protein to the blood stream directly after administering the therapeutic product to the nose, without the necessity for deposition of the product in the lung. Formulations for nasal delivery include those with dextran or cyclodextran.

Methods of Treatment, Methods of Preparing a Medicament

In another embodiment, the present invention extends to a method of treating schizophrenia or a disease or disorder related thereto, comprising administering to a mammal a therapeutically effective amount of a material selected from the group consisting of a PRODH comprising an amino acid sequence of SEQ ID NO:2, a conservative variant thereof, a fragment thereof, or an analog or derivative thereof. The phrase "therapeutically effective amount" is used herein to mean an amount sufficient to treat, and preferably decrease by at least about 30 percent, more preferably by at least 50 percent, most preferably by at least 90 percent, a symptom or symptoms associated with schizophrenia or a disease or disorder related thereto in a subject. In a particular embodiment, the PRODH, conservative variants thereof, fragments thereof, or analogs or derivatives thereof are delivered parenterally as described above.

In yet another aspect of the present invention, methods of treatment and manufacture of a medicament are provided. Conditions alleviated or modulated by the administration of the present derivatives are those indicated above.

Dosages. For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing.

Methods of Assaying Drugs or Agents using Mice and the PPI Test

Disclosed infra is a new mouse strain useful in assaying drugs or agents for the ability to treat schizophrenia, and the teachings to produce such a mouse. Furthermore, the PPI test which is used to examine the mice is discussed in detail below.

Hence, the present extends to a method of identifying drugs or agents useful in treating schizophrenia or a disease or disorder related thereto comprising the steps of:
  a) performing an first pre-pulse inhibition test (PPI) test on a mouse having within its genome two copies of an isolated variant allele of a Prodh gene comprising a DNA sequence of SEQ ID NO:7, wherein both copies are capable of expressing a mutant Prodh comprising an amino acid sequence of SEQ ID NO:8, to obtain a first percentage of inhibition of startle response;
  b) administering the potential drug or agent to the mouse;
  c) performing a second PPI test on the mouse to obtain a second percentage of inhibition of startle response; and
  d) comparing the first percentage to the inhibition of startle response with the second percentage of startle response, wherein an increase in percentage of inhibition in the second percentage of inhibition relative to the first percentage of inhibition is indicative of the ability of the drug or agent to treat schizophrenia or a disease or disorder related thereto. Thus, if the percentage of inhibition of startle response in the mouse having within its two active copies of an isolated variant allele of a Prodh gene comp mouse after administration of the drug or agent is greater than the percentage of inhibition of startle response in the Pro/Re mouse prior to inhibition, then the drug or agent has the ability to treat schizophrenia or a disease or disorder related thereto, such as obsessive compulsive disorder (OCD), bipolar disorder (BP) or major depressive disorder.

Also, the present invention extends to a method for identifying a drug or agent for treating schizophrenia or a disease or disorder related thereto. An example of such a method comprises the steps of:
  performing an first pre-pulse inhibition test (PPI) test on an F3 generation mouse from a cross Pro/Re X C57B1/6J wild-type, wherein the F3 generation mouse has two copies within its genome of an isolated variant allele of a Prodh gene comprising a DNA sequence of SEQ ID NO:7 which are capable of expressing a mutant Prodh comprising an amino acid sequence of SEQ ID NO:8, to obtain a first percentage of inhibition of startle response;
  administering the potential drug or agent to the F3 generation mouse from a cross of Pro/Re X C57B1/6J wild-type;
  performing a second PPI test on the F3 generation mouse from a cross of Pro/Re X C57B1/6J wild-type to obtain a second percentage of inhibition of startle response; and comparing the first percentage to the inhibition of startle response with the second percentage of startle response, wherein an increase in percentage of inhibition in the second percentage of inhibition relative to the first percentage of inhibition is indicative of the ability of the drug or agent to treat schizophrenia or a disease or disorder related thereto.

What's more, the present invention extends to a method for identifying a drug or agent for use in treating schizophrenia or a disease or disorder related thereto, comprising the steps of:

administering the drug or agent to an F3 generation mouse from a cross of Pro/Re X C57B1/6J wild-type, wherein the F3 generation mouse has two copies within its genome of an isolated variant allele of a Prodh gene comprising a DNA sequence of SEQ ID NO:7 which are capable of expressing a mutant Prodh comprising an amino acid sequence of SEQ ID NO:8;

performing a PPI test on the F3 generation mouse from a cross of Pro/Re X C57B1/6J wild-type to obtain a percentage of inhibition of the startle response in the F3 generation mouse from a cross of Pro/Re X C57B1/6J wild-type which was administered the drug or agent; and comparing the percentage of inhibition of the startle response in the F3 generation mouse from a cross of Pro/Re X C57B1/6J wild-type with the percentage of inhibition of the startle response in an unmedicated F3 generation mouse from a cross of Pro/Re X C57B1/6J wild-type, wherein the F3 generation mouse has two copies within its genome of an isolated variant allele of a Prodh gene comprising a DNA sequence of SEQ ID NO:7 which are capable of expressing a mutant Prodh comprising an amino acid sequence of SEQ ID NO:8.

An increase in percentage of inhibition in the percentage of inhibition in the medicated mouse relative to the percentage of inhibition in the unmedicated mouse is indicative of the ability of the drug or agent to treat schizophrenia or a disease or disorder related thereto.

Furthermore, the present invention extends to a method for identifying a drug or agent for use in treating schizophrenia or a disease or disorder related thereto, comprising the steps of:

administering the drug or agent to a mouse having within its genome two copies of an isolated variant allele of a Prodh gene comprising a DNA sequence of SEQ ID NO:7, wherein both copies are capable of expressing a mutant Prodh comprising an amino acid sequence of SEQ ID NO:8;

performing a PPI test on the mouse to obtain a percentage of inhibition of the startle response in the mouse; and comparing the percentage of inhibition of the startle response in the mouse with the percentage of inhibition of the startle response in an unmedicated mouse having within its genome two copies of an isolated variant allele of a Prodh gene comprising a DNA sequence of SEQ ID NO:7, wherein both copies are capable of expressing a mutant Prodh comprising an amino acid sequence of SEQ ID NO:8.

An increase in percentage of inhibition in the percentage of inhibition in the medicated mouse relative to the percentage of inhibition in the unmedicated mouse is indicative of the ability of the drug or agent to treat schizophrenia or a disease or disorder related thereto.

In addition, the present invention extends to a method for identifying a drug or agent for use in treating schizophrenia or a disease or disorder related thereto, comprising the steps of:

administering the drug or agent to a mouse having within its genome two copies of an isolated variant allele of a Prodh gene comprising a DNA sequence of SEQ ID NO:7, wherein both copies are capable of expressing a mutant Prodh comprising an amino acid sequence of SEQ ID NO:8;

performing a PPI test on the mouse to obtain a percentage of inhibition of the startle response in the mouse; and comparing the percentage of inhibition of the startle response in the mouse with the percentage of inhibition of the startle response in an unmedicated mouse having within its genome two copies of an isolated Prodh gene comprising a DNA sequence of SEQ ID NO:3, wherein both copies are capable of expressing a Prodh comprising an amino acid sequence of SEQ ID NO:4.

If the percentage of inhibition of the startle response in the medicated mouse is statistically equivalent to the percentage of inhibition in the mouse capable of expressing Prodh comprising a DNA sequence of SEQ ID NO:4, then the drug or agent has the ability to treat schizophrenia or a disease or disorder related thereto.

In another embodiment, the present invention extends to an a method for identifying a drug or agent for use in treating schizophrenia or a disease or disorder related thereto, comprising the steps of:

administering the drug or agent to an F3 generation mouse from a cross of Pro/Re X C57B1/6J wild-type, wherein the F3 generation mouse has two copies within its genome of an isolated variant allele of a Prodh gene comprising a DNA sequence of SEQ ID NO:7 which are capable of expressing a mutant Prodh comprising an amino acid sequence of SEQ ID NO:8;

performing a PPI test on the F3 generation mouse from a cross of Pro/Re X C57B1/6J wild-type administered the drug or agent to obtain a percentage of inhibition of the startle response in the mouse; and comparing the percentage of inhibition of the startle response in F3 generation mouse from a cross of Pro/Re X C57B1/6J wild-type administered the drug with the percentage of inhibition of the startle response in an F3 generation mouse from a cross of Pro/Re X C57B1/6J wild-type, wherein the F3 generation mouse has two copies within its genome of an isolated Prodh gene comprising a DNA sequence of SEQ ID NO:3 which are capable of expressing a Prodh comprising an amino acid sequence of SEQ ID NO:4.

If the percentage of inhibition of the startle response in the medicated mouse is statistically equivalent to the percentage of inhibition in the mouse capable of expressing Prodh comprising a DNA sequence of SEQ ID NO:4, then the drug or agent has the ability to treat schizophrenia or a disease or disorder related thereto.

The PPI test involves the evaluation of sensimotor gating. In particular, this test permits the evaluation of sensormotor gating from the degree of inhibition of an acoustic startle response by a prepulse preceding by 100 msec an abrupt startling stimulus (pre-pulse inhibition). PPI was recorded using a combination of two startle levels (100 and 115 dB) and two prepulse levels (82 and 90 dB) and is expressed as:

100−[(response to startle stimulus following pre-pulse/response to startle stimulus alone)×100].

Testing was conducted in an SR lab system (San Diego Instruments) Each of two accoustically insulated startle chambers contained a transparent acrylic cylinder (4 cm in diameter) mounted on a frame to which a motion sensor was attached for the detection and transduction of movement, and a sound generation system for the delivery of background white noise and acoustic stimuli. Immediately after placement in the chamber, the animal was given a 5 min. Acclimation period during which background noise (67 dB) was continually present, and then received 6 sets of the following 7 trial types counterbalanced to control for order: Trial 1: 40 ms, 100 dB noise burst alone; trial 2: 40 ms, 115 dB noise burst alone; trial 3-6: 100 dB or 115 dB startle stimuli preceded 100 ms by a 20 ms, 82 dB or 90 dB noise burst (prepulse); trial 7: no-stimulus/background noise alone (67 dB). Intertrial interval was variable (10–20 sec with an average of 15 sec). At the beginning of the block of 42 trials, the animal received the following 3 trials: 1 no-stimulus/background noise along (67 dB) trial, 1 startle stimulus alone trial for both 100 dB and 115 dB. At the end of the block of 42 trials the animal received the same 3 trials again in reverse order. The background noise level was 67 dB during the entire testing session. Data was analyzed using ANOVA with repeated measures.

The present invention may be better understood by reference to the following non-limiting Example, which is provided as exemplary of the invention. The following Example is presented in order to more fully illustrate the preferred embodiments of the invention. It should in no way be construed, however, as limiting the broad scope of the invention.

EXAMPLE

Evidence for an association between schizophrenia susceptibility and hemizygous deletions in chromosome 22q11 has previously been determined [Karayiorgou et at., *Proc. Natl. Acad. Sci. U.S.A.* 92, 7612 (1995)]. More specifically, three hemizygous cryptic deletions at 22q11 in a sample of 300 unrelated schizophrenic patients have previously been reported and characterized. [M. Karayiorgou et al., *Proc. Natl. Acad. Sci. U.S.A.* 92, 7612 (1995); M. Karayiorgou et al., *Amer. J. Med. Genet.* 74, 677 (1997)] The frequency of this microdeletion in the general population is estimated to be ~0.02% (although the latter is most likely an underestimate) and no deletions were found in a sample of 200 healthy controls. [M. Karayiorgou et al., *Proc. Natl. Acad. Sci. U.S.A.* 92, 7612 (1995); M. Karayiorgou et al., *Amer. J. Med. Genet.* 74, 677 (1997)] The identified locus (~1.5 Mb in size) is located in the proximal part of a region at chromosome 22q11, and has been implicated independently in schizophrenia susceptibility through linkage studies. [Karayiorgou, M. and Gogos, J., *Neuron* 19, 967 (1997)] This locus overlaps with a critical region involved in the etiology of Velocardio-facial (VCFS)/DiGeorge (DGS) syndromes [Driscoll et al., *J. Med. Genet.*30, 813 (1993)] It has been shown that ~29% VCFS children with 22q11 deletions develop schizophrenia or schizoaffective disorder in adolescence and adulthood [Pulver, A. E., et al., *J. Nerv. Ment. Dis.* 182, 476 (1994)] an estimate confirmed by a more recent independent study. 22q11 deletions have been identified among schizophrenia patients of diverse ethnic origins (Chinese, Israeli, British, Danish) and one study implicated the 22q11 region in early-onset schizophrenia Yan et al.,*Am. J. Med. Genet.* 81, 41 (1998)]. In addition, the increased rates of comorbid obsessive compulsive disorder (OCD) or symptoms (OCS) among schizophrenic patients with the 22q11 microdeletion locus [Karayiorgou M., Gogos, J. A., et al., Genotype and Phenotype Analysis of the 22q11 Schizophrenia Susceptibility Locus. Cold Spring Harbor Symposia on Quantitative biology, Vol. LXI, pp. 835–843, Cold Spring Harbor Press, Cold Spring Harbor, N.Y. (1996); Karayiorgou, M. et al.,*Proc. Natl. Acad. Sci.* 94, 4572–4575 (1997)] and similarly increased rates of anxiety, OCS and OCD in children and adults with the 22q11 microdeletion in the absence of schizophrenia indicates that the 22q11 genomic region may harbor one or more genes predisposing to schizophrenia or a disease or disorder related thereto.

Furthermore, an association in a recessive manner between a low activity allele of the Catechol-O-methyltransferase (COMT) gene, located at the proximal part of the 22q11 deleted region, and a susceptibility to OCD, particularly in males, has been reported. [Karayiorgou et al. 1997, supra.] The observation that ~20% of schizophrenia patients report obsessions and compulsions, features that are found in only 1–2% of the general population [Eisen, J. L & Rasmussen, S. A., *Obsessive Compulsive Disorder with Psychotic Features. J. Clin. Psychiatry* 54:373–379 (1993); Berman, I. Kalinowski, A., Berman, S. M., Lengua, J., and Green, A. I., *Obsessive and Compulsive Disorders in Chronic Schizophrenia. Compr. Psychiatry* 36:6–10 (1995)] indicates that schizophrenia and OCD may share some pathophysiological and genetic components. For example, one common central processing mechanism that seems to be affected in patients with schizophrenia and OCD is sensorimotor gating. Patients with schizophrenia and OCD demonstrate poor sensorimotor gating of the startle response as measured by impaired prepulse inhibition of an acoustic response and this may lead to sensory overload, distractibility and cognitive fragmentation.

Reported herein is the isolation and characterization of the human homolog (FIG. 1A) of the *D. melanogaster* sigA proline dehydrogenase gene (PRODH), which is responsible for the behavioral phenotype of the *D. melanogaster* sluggish-A mutant [Hayward, D. C., et al., *Proc. Natl. Acad. Sci. USA* 90, 2979 (1993)]. The gene was localized at the most centromeric part of the 22q11 deletions and was shown to be expressed in several tissues, including brain. Mapping of PRODH indicates this gene may contribute to the psychiatric phenotype associated with the 22q11 deletions, because proline has long been suspected to serve as a modulator of a synaptic transmission in the mammalian brain and in addition, proline dehydrogenase is involved in the biosynthesis and release of the neurotransmitter glutamate.

Elevated levels of proline have been reported in a DiGeorge/VCFS patient [Jacken, J., Goemans, N. Frynes, J.-P, Francois, I., de Zegher, F., *J. Inherit. Metab. Dis.* 19, 275 (1996)], wherein DiGeorge/VCFS is a contiguous gene microdeletion syndrome involving chromosome 22q11. The de novo origin of the deletion and the fact that both the parents and the sister of the affected proband had normal proline levels, suggested that deletion of a gene located within the 22q11 region is responsible for the observed hyperprolinaemia. Proline dehydrogenase is the first enzyme of proline catabolism that converts proline to Δ1-pyrroline-5-carboxylate [Wang, S. S. and Brandriss, M. C., *Mol. Cell Biol.* 6, 2638 (1986); Wang, S. S. and Brandriss, M. C., *Mol. Cell Biol.* 7, 4431 (1987)] and dysfunction of this enzyme is expected to result in abnormal proline metabolism. The Drosophila melanogaster sluggish-A gene (slgA) was previously shown to encode a proline dehydrogenase; activity of this enzyme is abnormally low in the slgA mutant that presents behavior abnormalities, and is restored to wild-type levels in transgenic flies carrying the wildtype slgA gene [Hayward, D. C., et al., *Proc. Natl. Acad. Sci. USA* 90, 2979 (1993)]. Database searches using the sequence of the *D. melanogaster* slgA gene identified several human Expressed Sequence Tag (EST) cDNA clones, encoding a protein sequence with a strong match to the *D. melanogaster* sigA coding region. In particular, an insert from EST ym93b08.r1 from a human brain library (GenBank R88591) was used to screen a human cerebellar as well as a kidney cDNA library using a BLAST search provided by the National Institutes of Health at http://www.ncbi.nlm.nih.gov/cgi-bin/BLAST on the World Wide Web. A score having an E value of $4e^{-06}$ is considered a "strong match". A cDNA fragment was used as a hybridization probe against a panel of monochromatic hybrids as well as an array of nine phage artificial chromosomes (PACs) previously mapped and ordered within the 22q11 region [Carlson, C. et al., *Am. J. Hum. Genet.*61, 620 (1997)]. Only chromosome 22 (not shown) and PAC-P457M14 provided a positive signal (FIG. 1B). This PAC is included in the smallest 22q11 deletion identified to date in patients with schizophrenia [M. Karayiorgou et al., *Proc. Natl. Acad. Sci. U.S.A.* 92, 7612 (1995); M. Karayiorgou et al., *Amer. J. Med. Genet.* 74, 677 (1997)] suggesting that the human homologue of sigA maps within the deleted region. Mapping was confirmed by PCR analysis on a previously described [M. Karayiorgou et al., *Proc. Natl. Acad. Sci. U.S.A.* 92, 7612 (1995); M. Karayiorgou et al., *Amer. J. Med. Genet.* 74, 677 (1997)] somatic cell hybrid line carrying a copy of the deleted chromosome 22 (not shown). Library screening, Northern blotting and hybridization, reverse transcription PCR and 5' Rapid Amplification of cDNA ends (5' RACE) were performed according to standard protocols [J. Sambrook, E. F. Fritsch, T. Maniatis, *Molecular Cloning: A Laboratory Manual* (Cold Spring Harbor Laboratory Press, Cold Spring Harbor, N.Y., 2nd edition, 1989)]. The sequence of both human and mouse clones was obtained by primer walking from both strands. Sequence alignment and estimations of sequence similarity were performed using the program DNASTAR. 22q11 PAC clones were provided by P. dejong, Roswell Polytechnical College and Institute, Buffalo, N.Y. Monochromatic hybrids were purchased from BIOS Laboratories (New Haven, Conn.).

Figure 1C:
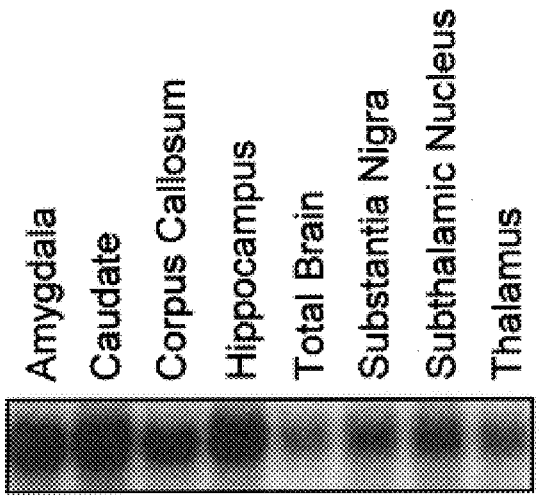

FIG. 1A shows an alignment of the predicted human PRODH with the *D. melanogaster* SLGA and yeast PUT1 proline dehydrogenase proteins, as well as with sequence from the mouse homologue (see below). The human and *D. melanogaster* proteins show 40.4% overall similarity as defined in the "DNASTAR LASERGENE" software program (DNASTAR, Inc. 1228 South Park Street, Madison, Wis. 53715), although the region of highest similarity among all homologues is localized toward the C-terminus where the human and *D. melanogaster* proteins are 60.4% similar. Northern blot analysis and autoradiography revealed a 2.4–2.5 kb band in several human tissues (such as heart, lung, liver, skeletal muscle, kidney, pancreas), including brain (not shown) and higher resolution analysis of the brain expression pattern revealed widespread distribution of the mRNA in several regions (FIG. 1C).

To determine whether the PRODH gene contributes to psychiatric phenotypes associated with the 22q11 deletions, two complementary studies were performed and reported herein. The first study involves isolation of the mouse Prodh gene, and identification of a mutation of this gene in the Pro/Re hypeprolinemic mouse strain. Furthermore, analysis of the startle response attenuation by prepulse inhibition (PPI) in these mice was used as a measure of sensorimotor gating, a central processing mechanism that is affected in patients with schizophrenia and OCD. The second study involved identification of PRODH gene variants that can be used to examine their inheritance in nuclear families with schizophrenia and obsessive compulsive disorder. These studies are described in more detail below.

Figure 2A:
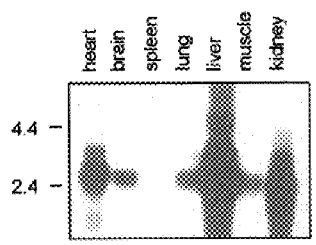
FIG. 2: (A) Northern blot analysis of expression of the mouse Prodh gene. The size of the markers in kilobases are indicated to the left of the blot. (B) Mutational analysis of the mouse Prodh gene from the Pro/Re strain: segment of antisense genomic sequence including the G→T (C→A) substitution (arrow) identified 135 base pairs upstream of the native termination codon, introducing a premature translational termination. (C) Analysis of plasma proline and glutamate levels in homozygous and wild type F3 generation mice from a cross between the original Pro/Re and C57/B6 wild type strain. The presence of the identified mutation correlates with increased levels of proline in F3 mice ($p<0.0001$). Y-axis values represent mmoles/L (±SEM). (D) Basal levels of glutamate, GABA and aspartate in the brains of Prodh-deficient mice and littermate controls. Neurotransmitter levels were analyzed one week after the termination of the behavioral analysis. Panels show basal levels of glutamate, GABA and aspartate in the frontal cortex, hypothalamus, amygdala, and hippocampus of homozygous and wild type animals of both sexes. Y-axis values are mean (±S.E.M). GAG/GAG wild type mice (gray bar); TAG/TAG homozygous mice (solid bar). Data was analyzed by two-way ANOVA (*p<0.05, ****p<0.0001).
Figure 2B:
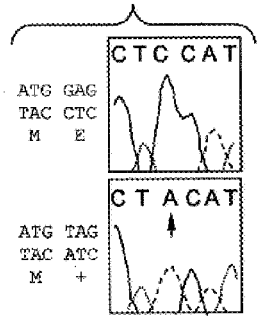
Figure 2C:
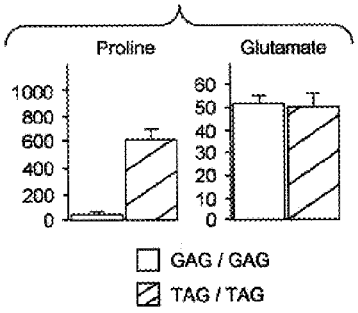

In the first study reported herein, human PRODH cDNA was used as a probe to isolate and sequence mouse Prodh cDNA from a cerebellar cDNA library. The mouse and human proteins show 86% similarity (FIG. 1A). Northern blot analysis and autoradiography revealed a 2.4–2.5 kb band in several mouse tissues (such as heart, lung, liver, skeletal muscle, kidney, pancreas) including brain (FIG. 2A). The PRO/Re mouse [R. L. Blake and E. S. Russell, *Science* 176, 809 (1972)], wherein the PRO/Re strain is a highly inbred strain developed by over 25 generation sibling inbreeding starting from an original cross between 129/ReJ and C57BL/6J strains, carries a presumably homozygous defect in proline dehydrogenase activity. In order to understand the contribution of the PRODH gene in the 22q11 associated psychiatric phenotype, the mouse Prodh gene from the PRO/Re mice was isolated, and a G to T substitution was identified 135 nucleotides 5' of the native termination codon has been identified that results in a premature translational termination (FIG. 1A, FIG. 2B). This substitution eliminates an MnlI site, and this information was used for genotyping the F3 generation from a cross between the original Pro/Re and C57/B6 wild type strain (F2 heterozygotes were intercrossed and offspring were genotyped by PCR]. Analysis of plasma amino acid levels demonstrated that presence of the identified mutation correlates with increased levels of proline in F3 mice, and, thus most likely accounts for the hyperprolinemia in the Pro/Re Strain. Specifically, F3 homozygous for the mutation present an average seven fold increase of the blood proline levels. In contrast, comparisons of glutamate levels did not reveal any significant changes (FIG. 2C).

Adult Prodh-deficient homozygous mice (TAG/TAG) were normal in appearance and development and had normal viability. However, 2–3 month old male Prodh-deficient homozygous mice weighed ~10% less than wild type littermates (GAG/GAG) [$F(1,33)=12.625$, $p=0.0012$)].

Figure 2D:
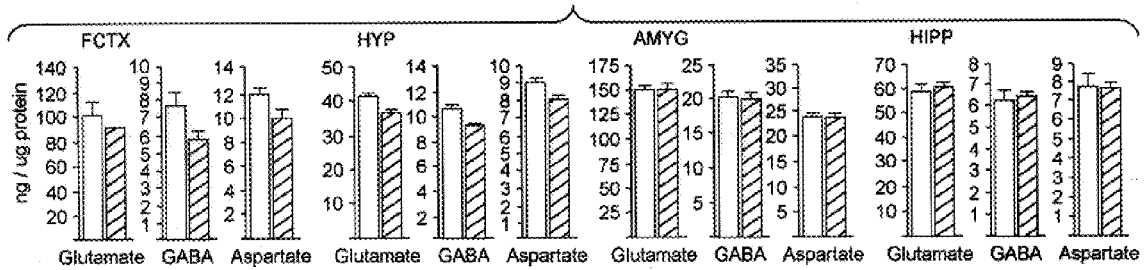

Brain morphology appeared identical in homozygous mice and their wild type littermates by gross evaluation. Upon histological examination of sections, cell groups in the forebrain and diencephalon appeared to be well formed with no obvious neuroanatomical alterations. Abnormal proline metabolism may alter biosynthesis and release of glutamate and γ-aminobutyric acid (GABA) [Johnson, J. L. and Roberts, E., *Brain Res.* 323, 247 (1984); Yoneda, Y. and Roberts, E., *Brain Res.* 239, 479 1982); Yoneda, Y., Roberts, E., and Dietz, G. W., *J. Neurochem.* 38, 1686 (1982)]. Because L-glutamate is the principal neuromuscular transmitter in *D. melanogaster*, it has been hypothesized that a deficiency in proline dehydrogenase may alter L-glutamate metabolism in specific nerve cell populations in *D. melanogaster*, thus being responsible for the sluggish phenotype reported by Hayward et al., (1986). GABA is thought to be the major inhibitory neurotransmitter of various inhibitory interneurons. Glutamate, in addition to being a major excitatory amino acid transmitter, may also serve as a precursor of GABA and aspartate, another excitatory transmitter [Johnson, et al (1984). Therefore, basal levels of glutamate, GABA and aspartate were compared in extracts from frontal cortex, hypothalamus, amygdala, and hippocampus of homozygous mutant and wild type animals (FIG. 2D) [Luine, V. N., Grattan, D. R., and Selmanoff, M., *Brain Res.* 747, 165 (1997); Grattan, D. and Selmanoff, M., *J. Neurochem.* 60, 2254 (1993)]. The frontal cortex section taken was between approximately +3.08 and +1.70 mm (according to the atlas of K. B. J. Franklin and G. Paxinos, *The Mouse Brain in Stereotaxic Coordinates,* Academic Press, New York, 1997) and two dorsomedial punches were taken. It contained the medial and ventral orbital cortex and the pre- and infra-limbic cortex. One punch of the dorsal hippocampus was taken between approximately −2.0 and −3.0 mm. The hypothalamus was sampled with bilateral punches between approximately 0.34 and 2.18 mm and consisted of the dorso and ventromedial nuclei, anterior hypothalamic nucleus, and arcuate nucleus. Aminoacids glutamate, aspartate, glycine, serine and γ-aminobutyric acid (GABA)—in the brain samples were measured using HPLC with electrochemical detection following precolumn derivatization of the sample with 0-phthalaldehyde and beta-mercaptoethanol. Briefly, punched tissues were expelled into sodium acetate buffer, pH 5.0, containing approximately 25 ng of homoserine as an internal standard (150 μl for cortex and 200 μl for hippocampus). The samples were centrifuged and 15 μl of supernatant, following automated precolumn derivatization, was injected using a refrigerated, Waters 717 Autosampler onto a Brownlee Velosep RP-18 3 micron column. Amino acids were detected with an ESA model 5200 Coulochem II detector with a model 5011 analytical cell with electrodes set at +0.1 mV to oxidize and remove derivatization contaminants and at +0.45 mV to oxidize and detect derivatized amino acids. Details of the mobile phase and derivatization reagent can be found in Grattan and Selmanoff, 1993. Picograms of amino acids were calculated with the Waters Millenium computer system by comparing the ratio of the peak heights of the transmitters and the internal standard in sample chromatograms with ratio of peak heights in chromatograms from external amino acid standards. Proteins were determined in the sample pellets and concentrations of amino acids are expressed as ng/μg of protein. Measurements were made in a single cohort of mice consisting of male and female homozygous (n=15) and wild type (n=11).

An 8% decrease in the levels of glutamate was observed in the frontal cortex of the Prodh-deficient mice but this did not reach statistical significance (90.7±5.6 versus 98.8±10.1, p=0.58). However, a significant ~25% decrease of GABA levels (5.7±0.3 versus 7.7±0.6, p=0.03) and a ~18% decrease of the aspartate levels (9.5±0.5 versus 11.5±0.4, p=0.01) was observed in the same brain region. Similarly, significant decreases in the levels of glutamate (~13%, 36.9±1.0 verses 42.3±1.4, p=0.0062), GABA (~10%, 9.3±0.1 verses 10.4±0.4, p=0.01) and aspartate (~10%, 8.0±0.2 verses 8.9±0.3, p=0.03) were observed in the hypothalamus of homozygous mutants. By contrast, no significant differences were observed among animals of either genotype in the levels of these three neurotransmitters in the amygdala and hippocampus. In addition, no significant differences were observed in the levels of glycine (another inhibitory neurotransmitter), in all brain regions examined.

Figure 3A:
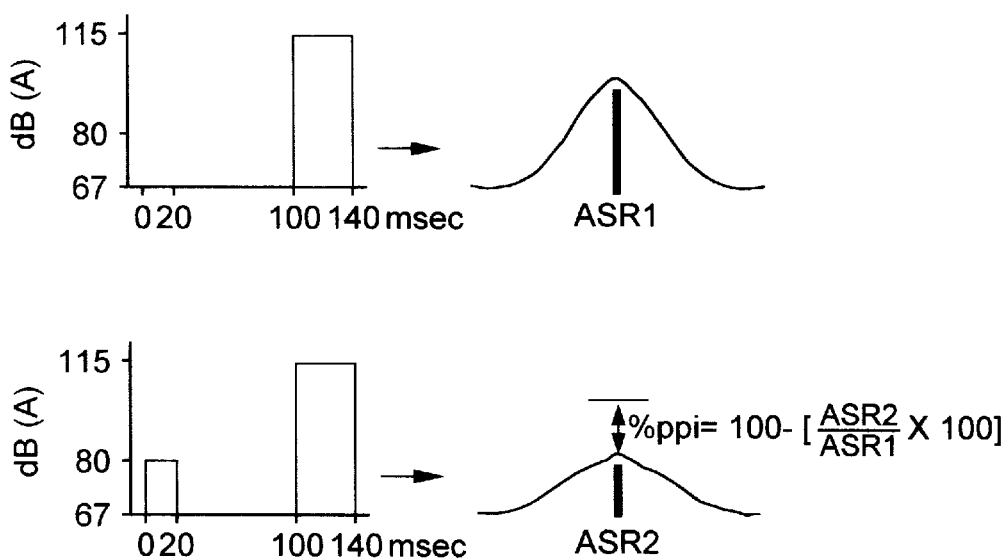
FIG. 3: Sensorimotor gating in Prodh-deficient mice: (A) Schematic outline of the experiment. (B) Prepulse inhibition of an acoustic startle response; prepulse inhibition was examined for a combination of two startle dB levels (110 dB and 15 dB) and two prepulse dB levels (82 dB and 90 dB); higher Y-axis values (mean±SEM) represent greater percent inhibition. ANOVA with repeated measures revealed a significant attenuation in the overall level of PPI in the homozygous mutant mice compared to wild type littermates [F(1, 66)=6.14, p=0.015]. (C) Amplitude of startle response at two different startling stimuli; Y-axis values (mean±SEM) represent weight-corrected peak amplitude startle (Vmax). No significant differences were observed between genotypes at either 100 dB (p=0.0799) or 115 dB (p=0.125). (D) Habituation of the startle response to repeated presentations of an 115 dB burst. Weight-corrected startle magnitude values (Vmax) were averaged, expressed as a percentage of the first block and analyzed using ANOVA with repeated measures. No significant differences were observed between genotypes (p=0.675).

Homozygous mutant mice and wild type littermates, 2–3 months old at the onset of testing were analyzed in behavioral assays of sensory reception/processing, locomotion and anxiety. Forty two homozygous and 26 wild type littermate mice of both sexes, 2–3 months old at the onset of testing were used for the behavioral analysis. Animals were housed in groups of 2–4 and were maintained on a reverse 12:12 h light-dark cycle with lights off at 0700 hrs. All testing occurred between 0900 and 1800 hrs. Prior to all testing, animals were handled and weighed. The behavioral tests were performed in the following order: locomotor activity, light/dark transition, PPI and habituation of the startle response. At the conclusion of all behavioral assays the genotypes of all mice were reconfirmed by PCR analysis. One central processing mechanism that is affected in patients with psychiatric disorders (primarily schizophrenia, and probably OCD) is sensorimotor gating, a neural filtering process that allows attention to be focused on a given stimulus. This impaired attentional filtering is thought to result in sensory overload, distractibility, cognitive fragmentation and possibly psychotic symptoms [D. Braff et al., *Psychophysiology* 15, 339 (1978); C. Grillon, R. Ameli, D. S. Charney, *Biol. Psychiatry* 32, 939 (1992); N. R. Swerdlow, C. H. Benbow, S. Zisook, *Biol. Psychiatry* 33, 298 (1993); W. Perry and D. L. Braff, *Am. J. Psychiatry* 151, 363–367 (1994)]. Sensorimotor gating can be evaluated from the degree of inhibition of an acoustic startle response by a weak prepulse preceding by 30–500 msec an abrupt startling stimulus (FIG. 3A, pre-pulse inhibition, (PPI) [R. Paylor and J. N. Crawley, *Psychopharmacology* 132, 169 (1997); N. R. Swerdlow, D. L. Braff, N. Taaid, M. A. Geyer, *Arch. Gen. Psychiatry* 51, 139 (1994); S.F. Logue, E. H. Owen, D. L. Rasmussen, J. M. Wehner, *Neuroscience* 80, 1075 (1997); A. E. Bullock, B. S. Slobe, V. Vasquez, A. C. Collins, *Behav Neurosci.* 111, 1353 (1997)]. PPI is one of a few neuropsychological measures in which humans and rodents can be evaluated more or less in a similar fashion. In rodents, the neural circuit underlying the startle reflex is thought to involve four to five synapses [M. Davis, D. S. Gendelman, M. D. Tischler, P. M. Gendelman, *J. Neurosci.* 2, 791 (1982)] and a number of centers and neurotransmitters may exert prepulse influences on its function [M. A. Geyer and D. L. Braff, *Schizophr. Bull.* 13, 643 (1987)]. In addition, it has been suggested that GABA-mediated presynaptic control of excitatory neurotransmitter release may be involved in the control of gating of sensory responses [Duter and R. A. Nicoll, *Neuron* 1, 585 (1988)] and GABAergic circuitry may partly mediate the decrease in sensorimotor gating induced by dopamine overactivity [N. R. Swerdlow, D. L. Braff, M. A. Geyer, *Brain Res.* 532, 146 (1990); M. H. Kodsi and N. R. Swerdlow, *Brain Res. Bull.* 43, 219 (1997)] and activation of nicotinic receptors [N. R. Swerdlow, D. L. Braff, M. A. Geyer, *Brain Res.* 532, 146 (1990); M. H. Kodsi and N. R. Swerdlow, *Brain Res. Bull* 43, 219 (1997)].

Another measure of sensorimotor gating is based on electoencephalographic techniques designed to study response to paired auditory stimuli. In this case, suppression of the P50 wave in humans and the N40 wave in rodents by a second stimulus, when two auditory stimuli are presented in sequence, is used as a measure of normal gating [R. Freedman et al., in *Schizophrenia: Origins, processes, treatment, and outcome,* R. L. Cromwell and C. R. Snyder, Eds., (Oxford Univ. Press, New York, 1993), pp. 98–108; K. E. Stevens et al., *Neuropsychophannacology* 15, 152 (1996)]. Patients with schizophrenia as well as some of their non-symptomatic family members show decreased attenuation of the second P50 wave. Recently a genetic linkage has been described between a DNA marker on chromosome 15 and decreased P50 attenuation in some families with schizophrenia [R. Freedman et al., *Proc. Natl. Acad. Sci. U.S.A.* 94, 587 (1997)].

METHODS AND MATERIALS

Library Screening

Library screening, Northern blotting and hybridization, reverse transcription PCR and 5' Rapid Amplification of cDNA ends (5' RACE) were performed according to standard protocols [J. Sambrook, E. F. Fritsch, T. Maniatis, *Molecular Cloning: A Laboratory Manual* (Cold Spring Harbor Laboratory Press, Cold Spring Harbor, N.Y., 2nd edition, 1989)]. The sequence of both human and mouse clones was obtained by primer walking from both strands. Sequence alignment and estimations of sequence similarity were performed using the program DNASTAR. 22q11 PAC clones were provided by P. deJong, Roswell Polytechnical College and Institute, Buffalo, N.Y. Monochromatic hybrids were purchased from BIOS Laboratories (New Haven, Conn.).

Genotyping Mutants and Wild Type Littermates

Pro/Re and C57/B6 mice were purchased from Jackson Laboratories. For PCR genotyping for the identified mutation, the following primers were used:

F: 5'GACCAAATCAGCTTCCCACT (SEQ ID NO:5);
R: 5'CCCTTCATGATGCTGCTGTT (SEQ ID NO:6).

Target sequences were amplified in a 50 μl reaction mixture containing 100 ng of genomic DNA in 50 mM KCl, 10 mM Tris-HCl (pH 8.3), 1.5 mM $MgCl_2$, 0.1% gelatin, 50 mm of each primer, 200 mM of each dNTP (dATP, dCTP, dGTP, dTTP), and 1.5 u Taq polymerase. PCR was performed in a programmable PCR apparatus (MJ Research, Inc.). Amplification was as follows: 80° C.×8 min (1×), 92° C.×1 min/60° C.×40 sec/72° C.×1 min (30×), 72° C.×7 min (1×), 4° C.×5 min. 45 μl of the amplified product was digested with 20–40 u of MnlI in a 60 μl reaction volume, according to the manufacturer's specifications. The digested product was electrophoresed in a 4% 1×TBE NuSieve agarose gel.

Because of the development of a blood-brain barrier towards proline early in development [J. L. Purdy and S. C. Bondy, *Neuroscience* 1, 125 (1976)], plasma levels may not be adequately describing brain levels, although previous analysis of a CD-1×Pro/Re F3 cross revealed an increase in the brain proline levels as well [C. F. Baxter, R. A. Baldwin, J. L. Davis, J. J. Flood, *Pharmac. Biochem. & Behav.* 22, 1053 (1985)]. The normal concentration of proline in human plasma is between 100 and 450 mM. The concentration of proline in cerebrospinal fluid is considerably lower (4.2 mM) [C. R. Scriver and L. E. Rosenberg, *Aminoacid metabolism and its disorders* (Saunders, Philadelphia, 1973)].

The nucleotide sequence obtained from the cerebellar cDNA clones overlapped partly with the sequence of the kidney cDNA clones (data not shown). Additional sequence was obtained using a 5'RACE approach on total human brain mRNA. As part of a *D. melanogaster*/human sequencing project, Campbell and colleagues [H. D. Campbell, G. C. Webb, I. G. Young, *Hum. Genet.* 101, 69 (1997)] also identified a human cDNA with homology to sigA (the gene product was assigned the name PRODH). The reported sequence is identical to the one determined in this study with the exception of a G insertion in the 3' UTR, 1793 base pairs downstream of the initiator methionine. Analysis in a small number of individuals suggests that this variation represents either a sequencing artifact or a very rare polymorphism. In addition, homologues from (intentionally left blank) *C. elegans* [GeneBank Z81060, Sulston et al., *Nature* 356, 37 (1992)] and *Arabidopsis thaliana* [N. Verbruggen, X.-J. Hua, M. May, M. Montagu, *Proc. Natl. Acad. Sci. U.S.A.* 93, 8787 (1996)] have also been reported.

Testing of Prodh-deficient Mice and Wild Type Littermates

Forty two homozygous and 26 wild type littermate mice of both sexes, 2–3 months old at the onset of testing were used for the behavioral analysis. Animals were housed in groups of 2–4 and were maintained on a reverse 12:12 h light-dark cycle with lights off at 0700 hrs. All testing occurred between 0900 and 1800 hrs. Prior to all testing, animals were handled and weighed. The behavioral tests were performed in the following order: locomotor activity, light/dark transition, PPI and habituation of the startle response. At the conclusion of all behavioral assays the genotypes of all mice were reconfirmed by PCR analysis.

Spontaneous locomotor activity was tested in an open field apparatus, a clear acrylic chamber (40.5×40.5×30 cm) equipped with infrared sensors for the automatic recording of horizontal activity (Digiscan Model RXYZCM, Accuscan Instruments, Inc., Columbus, Ohio). Each subject was initially placed in the center of the chamber and total distance traveled over the next 15 min was used as the measure of activity. To minimize the influence of anxiety on activity level, activity was monitored under indirect, very dim light and sound-attenuated conditions.

Following the initial test of locomotor activity, the effect of the mProdh mutation on anxiety-like behaviors (collectively termed anxiety, reactivity or emotionality) was recorded in a dark/light exploratory model in a 2-compartment light/dark box. The apparatus and conditions were similar to those used for the locomotor assay, except that an enclosed black acrylic box (40×20.5×20.5 cm) was inserted into the right half of the chamber with an opening (13×5 cm) allowing for free passage between the two compartments monitored by an infrared beam. The open compartment was now directly illuminated by a 60-watt bulb placed 60 cm above the floor of the compartment. Animals were initially placed in the dark compartment and data collection commenced immediately for 10 min. Previous work assessing the effects of anxiolytic and anxiogenic agents has established the validity of this behavioral procedure in evaluating anxiety-like behaviors in rodents. Variables recorded as a measure of anxiety included latency to emerge from the dark compartment into the more aversive brightly lit compartment, and amount of time spent ambulating in each of the two compartments.

Testing was conducted in a SR-Lab system (San Diego Instruments, San Diego, Calif.). Each of two acoustically insulated startle chambers contained a transparent acrylic cylinder (4 cm in diameter) mounted on a frame to which a motion sensor was attached for the detection and transduction of movement, and a sound generation system for the delivery of background white noise and acoustic stimuli. To ensure comparable sensitivities of these detectors across the two chambers, a vibrating standardization unit (San Diego Instruments, San Diego, Calif.) was used. A CompuAdd 386 microprocessor and SDI interface board and software were used for the delivery of stimuli and response recording (100 1-ms readings beginning at startle stimulus onset). Response amplitude was calculated as the maximum response level occurring during the 100 ms recording. Both chambers were calibrated for equivalent stimulus intensities and response sensitivities with a digital sound level meter (RadioShack), and experimental groups were balanced across chambers. Because animals can in principle habituate to the prepulse [J. C. Gewirtz and M. Davis, *Behav. Neurosci.* 109, 388 (1995)], as well as to the startle stimulus [T. D. Blumenthal, *Psychophysiology* 34, 446 (1997)], the number of trials was kept to the essential minimum. The choice of the two prepulse bursts used in this experiment was based on a pilot experiment. Immediately after placement in the chamber, the animal was given a 5 min acclimation period during which background noise (67 dB) was continually present, and then received 6 sets of the following 7 trial types counterbalanced to control for order: Trial 1: 40 ms, 100 dB noise burst alone; Trial 2: 40 ms, 115 dB noise burst alone; Trial 3–6: 100 dB or 115 dB startle stimuli preceded 100 ms by a 20 ms, 82 dB or 90 dB noise burst (prepulse); Trial 7: no-stimulus/background noise alone (67 dB). Intertrial interval was variable (10–20 sec with an average of 15 sec). At the beginning of the block of 42 trials, the animal received the following 3 trials: 1 no-stimulus/background noise alone (67 dB) trial, 1 startle stimulus alone trial for both 100 dB and 115 dB. At the end of the block of 42 trials the animal received the same 3 trials again in reverse order. The background noise level was 67 dB during the entire testing session. Data were analyzed using ANOVA with repeated measures.

In order to obtain additional information on the perception of the employed prepulse stimuli by wild type and mutant mice, one week after the completion of the PPI experiment, prepulse alone startle responses were evaluated at 82 dB and 90 dB. Mice were exposed to three consecutive 40 ms stimuli: 67 dB white noise (background trial), 82 dB (prepulse 1 trial), and 90 dB (prepulse 2 trial), distributed pseudorandomly and separated by an average of 15 sec intertrial intervals. This sequence was repeated 10 times, that is, each stimulus were presented 30 times. The background noise level was 67 dB during the entire testing session. Whereas a prepulse alone startle response to 82 dB was barely detectable over background for both genotypes, a response to 90 dB could be reliably evaluated [there was a significant difference between response levels to 67 dB and 90 dB for both wild type (p=0.0017) and homozygous mutant animals (p=0.0001)]. The amplitude of the startle response at 90 dB was ~20% of the one observed for the 100 dB startle stimulus and it was indistinguishable between the two genotypes (p=0.6). Induction of a startle response by the 90 dB prepulse stimulus is unlikely to interfere with the interpretation of the observed PPI patterns since previous extensive analysis of different mouse strains demonstrated that no correlation exists between the startle response to 90 dB stimulus and the level of prepulse inhibition obtained with a 90 dB prepulse. Moreover, the same analysis showed that there is no correlation between the strain-specific dB threshold for induction of a startle response and the level for prepulse inhibition with any of the prepulse stimuli.

Habituation of the acoustic startle response was evaluated as follows: 36 homozygous mutant and 20 wild type animals were exposed to startle stimuli of broadband 115 dB for 40 ms with an average of 15 sec (10–20 sec) intertrial interval, in the presence of 67 dB broadband background noise. The session began with 5 min acclimation period, followed by 5 consecutive administrations of the 40 ms broad-band 115 dB burst. This block was repeated 24 times, resulting to 120 consecutive presentations of the 115 dB noise. Weight-corrected startle magnitude values (Vmax) were averaged for each block, expressed as percentage of the first block and analyzed using ANOVA with repeated measures. In addition, slopes of the habituation curves were analyzed by simple linear regression analysis.

Results and Conclusion

Figure 3B:
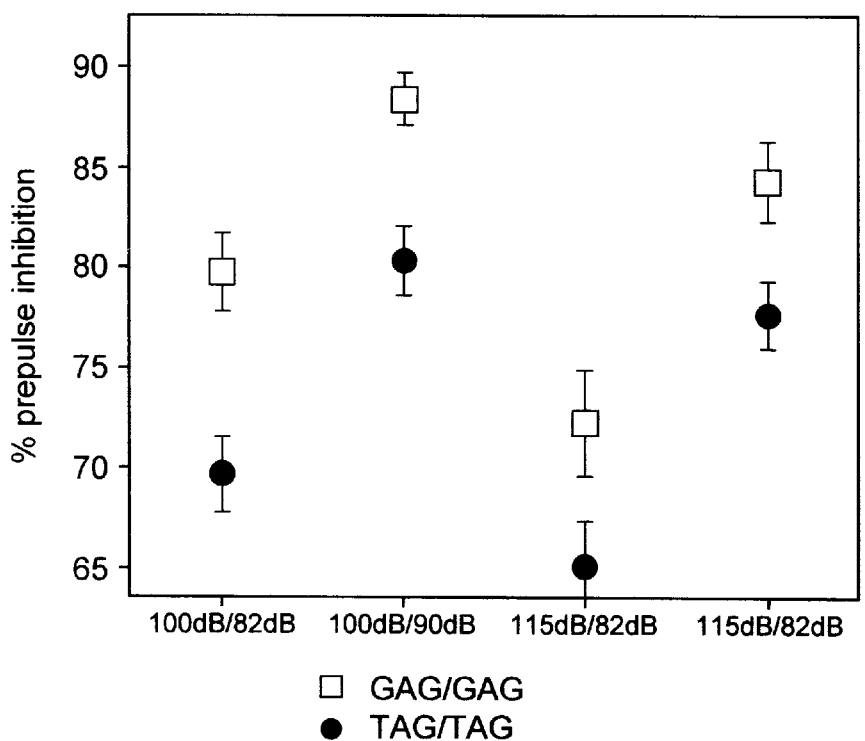
Figure 3C:
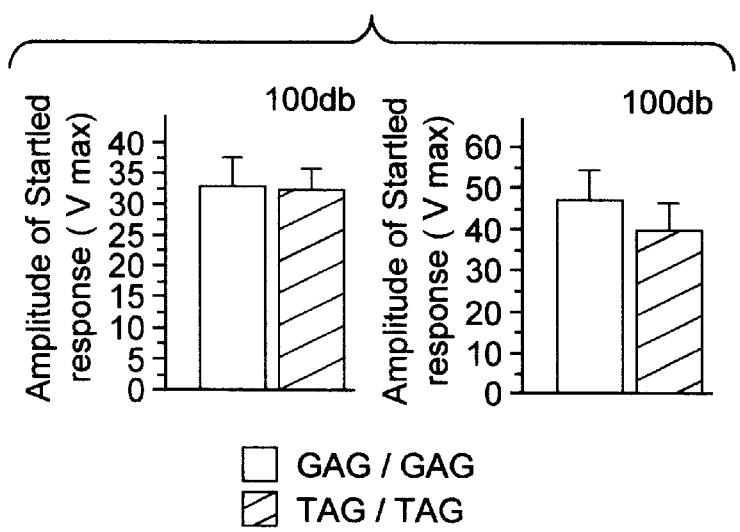
Figure 3D:
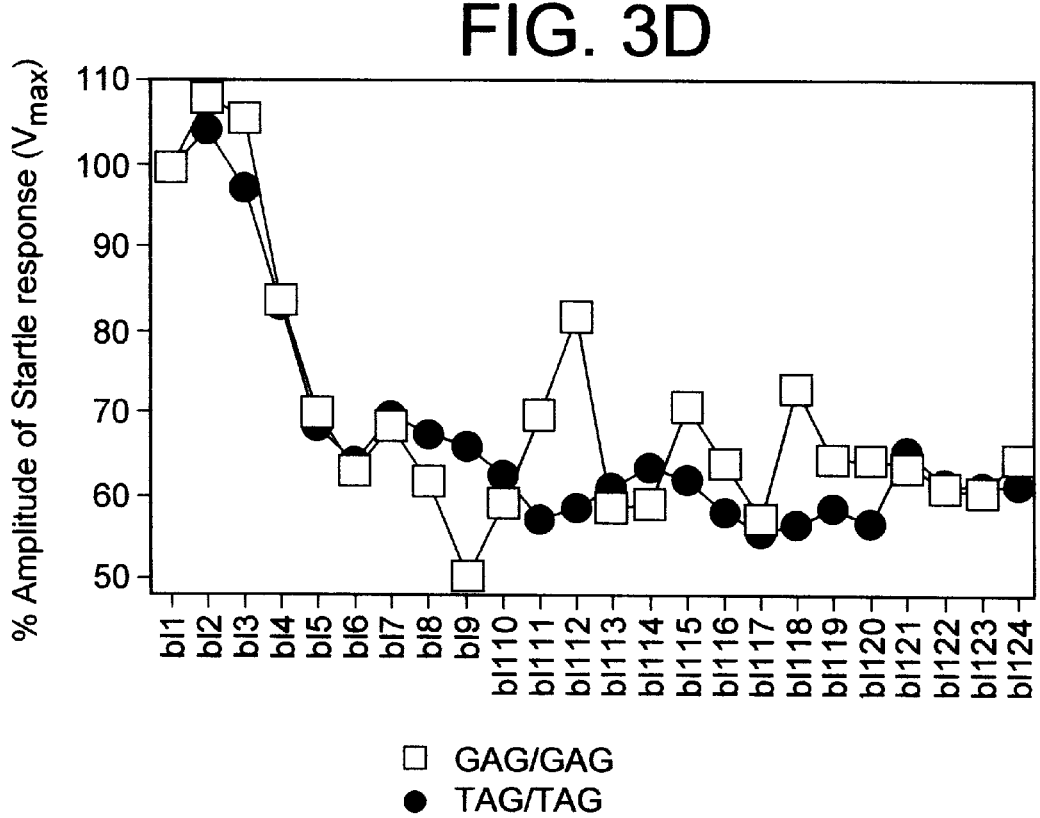
Figure 4A:
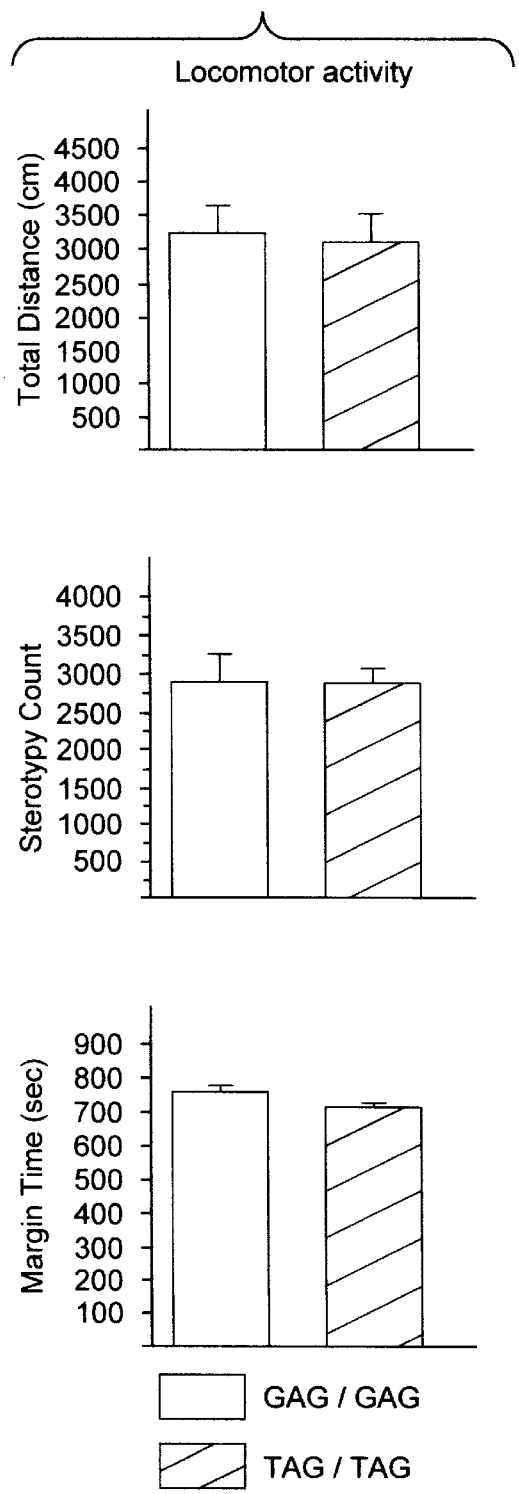
FIG. 4: Locomotion and anxiety-like behaviors (collectively termed anxiety, reactivity or emotionality) of Prodh-deficient mice: (A) Open field locomotion assay: No significant differences between genotypes were observed in total distance traveled (p=0.747), stereotypic behavior (p=0.839), or time spent at the margin of the field (an estimate of anxiety, p=0.078). Data were collected every 5 minutes over a 15 minute period and analyzed with ANOVA with repeated measures. Because animals were not preexposed to the chamber prior to testing, data collected every five minutes were also analyzed separately using two-way ANOVA (not shown) but no genotype or sex effect were observed. (B) Dark-light assay: no significant differences were observed between genotypes in latency to emerge into the lit compartment (p=0.597), or in horizontal activity in either the lit (p=0.194) or the dark compartment (p=0.711).
Figure 4B:
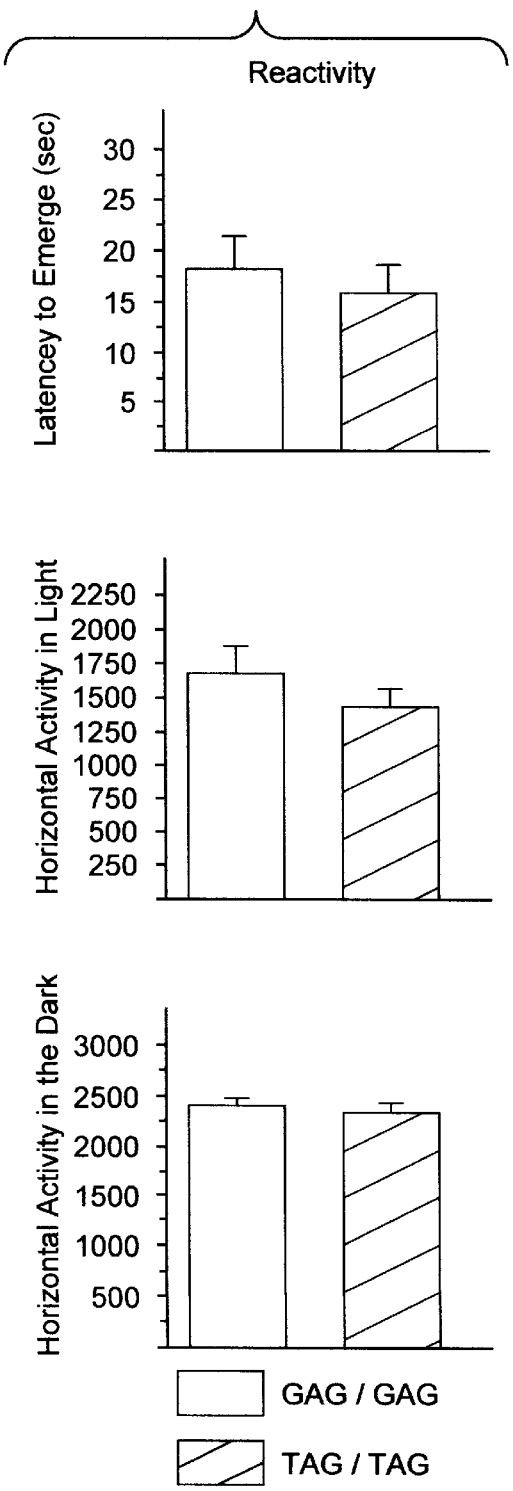

Prodh-deficient mice and wild type littermates were examined for abnormalities in sensorimotor gating. PPI was recorded, using a combination of two startle levels and two prepulse levels and expressed as 100-[(response to startle stimulus following pre-pulse/response to startle stimulus alone)×100] (such that higher percentages represent greater levels of inhibition, FIG. 3A). This experiment demonstrated a significant attenuation in the overall level of PPI in the homozygous mutant mice compared to wild type littermates [F(1,66)=6.14, p=0.015] (FIG. 3B). No sex differences were noted (p=0.866) and the % PPI increased with increasing prepulse levels in both genotypes. Two features of the startle responses were also evaluated: amplitude of the startle response (ASR) and habituation (the decrement in the ASR over repeated presentations of the same stimulus, a measure of plasticity exhibited by startle responses). ASR can be affected by several factors, including the integrity and excitability of the responding neurons in subcortical auditory centers [J. F. Willot, J. Kulig, T. Satterfield, *Hear. Res.* 16, 161 (1984); M. Koch, C. Kling, C. M. Becker, *Neuroreport* 7, 806, 1996]. Analysis by genotype did not reveal significant differences in the weight-corrected startle amplitudes between wild type and Prodh-deficient mice (FIG. 3C). Although a number of studies seem to suggest a dissociation between startle amplitude and PPI [R. Paylor and J. N. Crawley, *Psychopharmacology* 132, 169 (1997); V. P. Bakshi, N. R. Swerdlow, M. A. Geyer, *J. Pharmacol. Exp. Ther.* 271, 787 (1994); C. Johansson, D. M. Jackson, J. Zhang, L. Svensson, *Pharmacol. Biochem. Behav.* 52, 649 (1995)], this result indicates that the observed attenuation of PPI is not associated with an impaired startle response and in addition reveals an anatomical and functional integrity of the responsive neurons in the PRODH-deficient mice. Furthermore, homozygous mutant mice did not demonstrate any impairment in the habituation of the acoustic startle, at least under the conditions tested (FIG. 3D) [C. J. Wilson and P. M. Groves, *J. Comp. & Physiol. Psychiatry* 83, 492 (1973); M. A. Geyer and D. L. Braff, *Psychophysiology* 19, 1 (1982)]. Locomotor activity and anxiety (reactivity) were also assayed. In sharp contrast to the observed sensorimotor gating deficits, no significant differences in the total distance traveled, stereotypic behavior, or time spent in margin versus center (an estimate of anxiety) were observed among animals of either genotype in the open field locomotor assay (FIG. 4A) [W. E. Crusio, H. Schwegler, J. H. van Abeelen, *Behav. Brain Res.* 32, 80 (1989)]. In addition, no significant effect of genotype on latency to emerge into the more aversive brightly lit compartment, or time spent ambulating in either light or dark compartment was observed in the dark-light assay for anxiety (FIG. 4B) [J. Crawley and F. K. Goodwin, *Pharmacol. Biochem. Behav.* 13, 167 (1980); C. Mathis, S. M. Paul, J. N. Crawley, *Behav. Genet.* 24, 171 (1994); C. Mathis, P. E. Neumann, H. Gershenfeld, S. M. Paul, J. N. Crawley, *Behav. Genet.* 25, 557 (1995)].

Elevated proline concentration has been previously associated with behavioral deficits in *D. melanogaster* (defective phototaxis and low locomotor activity with indecisive movement pattern). The marked behavioral abnormalities observed in the sigA mutant flies correlated with a twofold elevation of proline in the brain [D. C. Hayward et al., *Proc. Natl. Acad. Sci. U.S.A.* 90, 2979 (1993)], suggesting that behavioral effects may not necessarily depend on grossly elevated proline levels. In humans, PRODH deficiency is likely to be associated with hyperprolinemia type I, a rare metabolic disorder [J. M. Phang, G. C. Yeh, C. R. Scriver, in *The Metabolic and Molecular Bases of Inherited Disease,* C. R. Scriver, A. L. Beaudet, W. S. Sly, D. Valle, Eds. (McGraw-Hill, New York, 1995), pp. 1125–1146]. Unlike most metabolic phenotypes, hyperprolinemia type I heterozygotes (such as patients with hemizygous 22q11 microdeletions) can demonstrate intermediate level increases of plasma proline [J. Jacken, N. Goemans, J.-P. Fryns, I. Francois, F. de Zegher, *J. Inherit. Metab. Dis.* 19, 275 (1996); Phang, et al., (1995)]. The nature of the effects of abnormally high proline (as in hyperprolinemia type I homozygotes) remain controversial and an exact link between the defect in proline metabolism and a behavioral/neurological phenotype in humans is still lacking. Several of the initially proposed features of hyperprolinemia type I (such as learning deficits) have not been observed reproducibly even among hyperprolinemic siblings of affected probands [F. Mollica and L. Provone, *Acta Paediatr. Scand.* 65, 206 (1976)]. Although under no obligation to explain such results, and certainly not intending to be bound by any hypothesis to explain these results, it is possible that fortuitous clinical findings, allelic heterogeneity and genetic background-dependent penetrance account for the variable observations. The rarity of this disorder and the phenotypic inconsistencies have impeded systematic psychiatric evaluation of these patients, although three cases of patients with psychiatric symptoms (schizophrenia, psychotic symptoms, autism) and increased blood proline levels have been reported [T. L. Perry, J. W. Wright, S. Hansen, *Biol. Psy-* chiatry 18, 89 (1983); M. Efron, *N. Engl. J. Med.* 272, 1243 (1965); T. Rokkones and A. C. Løken, *Acta Paediatr. Scand.* 57, 225 (1968)]. In mice, initial analysis of the original Pro/Re strain, revealed specific learning deficits J. L. Davis, R. M. Pico, J. F. Flood, *Behav. Neur. Biol.* 48,128 (1987)] and studies in chicks have shown that intracerebral administration of proline may result in selective disruption of memory formation [A. Cherkin, M. J. Eckardt, L. K. Gerbrandt, *Science* 193, 242 (1976)].

Identification and Characterization of Variant Alleles of the Human Proline Dehydrogenase Gene In the second study reported herein, common sequence variations in the more conserved C-terminal part of the human cDNA were scanned in ninety-two individuals affected with schizophrenia. Genomic PCR and primarily reverse transcription (RT) PCR using total mRNA isolated from transformed lymphocytes was applied. Eight polymorphisms were identified in this region:

a silent G to A transition at the third position of codon 83, which introduces a PstI site;

a C to T transition at the first position of codon 101 which results in a substitution of arginine for tryptophan;

a G to A transition at the second position of codon 101 which results in a substitution of arginine for glutamine;

a silent C to T transition at the first position of codon 247;

a C to T transition in the third position of codon 342;

a C to T transition in the third position of codon 421;

an A to G transition at the second position of codon 437, which results in a substitution of glycine for arginine; and a silent T to C transition at the first position of codon 497, which introduces a PvuII site.

Experiments using RT-PCR with primers flanking introns, showed that all variations were present in PRODH mRNA. Analysis of these variations in more extended samples revealed that the PvuII polymorphism is relatively frequent in that ~30% of chromosomes in a sample of patients with schizophrenia displayed this variation.

Moreover, statistical data from particular families whose members suffer from schizophrenia have been gathered, and demonstrate a direct link between the PRODH gene polymorphism comprising the silent T to C transition at the first position of codon 497, which introduces a PvuII site, and susceptibility of a subject to schizophrenia. In particular, a transmission disequilibrium test (TDT) [Spielman, R. S. et al. Transmission test for linkage disequilibirium: the insulin gene region and insulin-dependent diabetes mellitus (IDDM). *Am. J. Hum. Genet.* (1993), 53:506–516] was performed on data from families in which members suffered from schizophrenia. This test takes affected individuals with their two parents. All three are typed for a marker, one allele of which is believed to be associated with the disease. The TDT considers the cases where at least one parent is heterozygous at the marker allele (M1) which is suspected of being associated with the disease. One of the two marker alleles of each heterozygous patent is transmitted to each affected offspring and one is not. The test compares the frequency of M1 among the transmitted and nontransmitted alleles. The significance of the association is tested by a simple $\chi^2$ test (Table 1).

TABLE 1

Tests to determine whether marker allele M1 is associated with a disease.

| TDT test | Nontransmitted allele | |
|---|---|---|
| Transmitted allele | M1 | Not M1 |
| M1 | a | b |
| not M1 | c | d |

For either test, $\chi^2$ (1 degree of freedom)=$(b-c)^2/(b+c)$ The TDT: families are selected where affected probands have at least one parent who is heterozygous for M1. The transmitted and nontransnitted parental alleles are compared.

Figure 5:
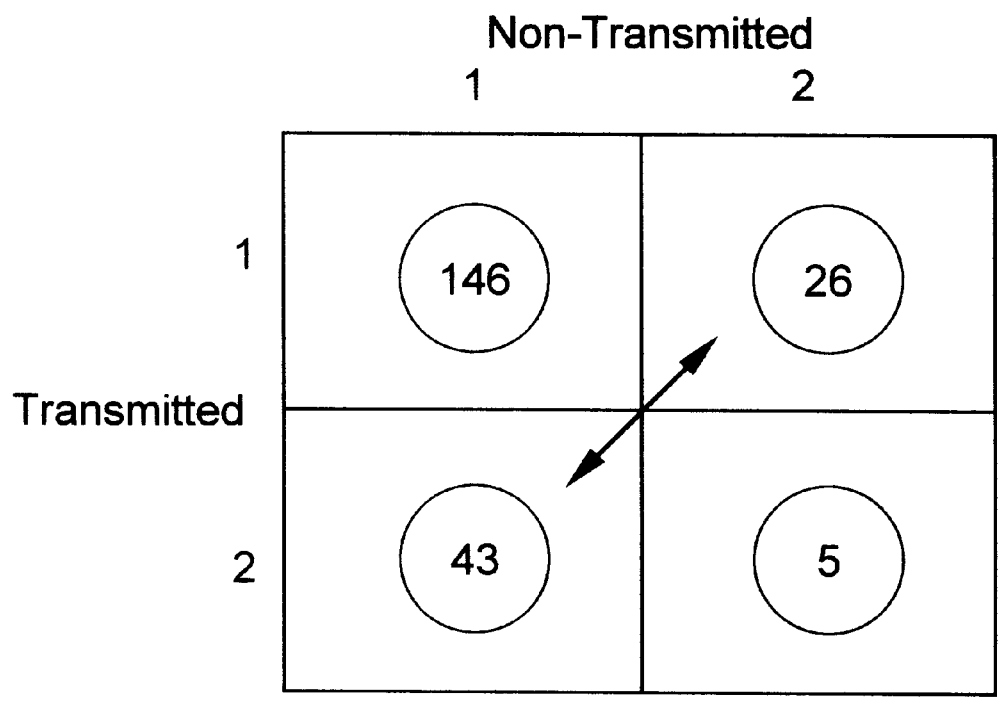
FIG. 5: shows the results of the testing of families with schizophrenia to determine whether the polymorphism of the PRODH gene comprising a variation in SEQ ID NO:1, wherein the variation comprises a silent T to C transition at the first position of codon 497, which introduces a PuvII site is preferentially transmitted in such families. In particular, results of a Transmission Disequilibrium Test (TDT) are disclosed which show the preferential transmission of a variant allele of the PRODH gene comprising a DNA sequence having a variation in SEQ ID NO:1, wherein the variation comprises a silent T to C transition at the first position of codon 497.

The results of the TDT, set forth in FIG. 5, show there is a statistically significant preferential transmission of the PRODH gene polymorphism comprising the silent T to C transition at the first position of codon 497, which introduces a PvuII site, and susceptibility of a subject to schizophrenia, or disease or disorders related thereto, such as obsessive compulsive disorder (OCD), bipolar disorder (BP), or major depressive disorder (MDD).

REFERENCES

L. E. Adler et al., *Schiz. Bulletin* 24, 189 (1998).
S. Akbarian et al., *Cerebral Cortex* 5, 550 (1995).
S. E. Bachus et al., *Society for Neurosci.* 23 (854.1), 2198 (1997).
V. P. Bakshi, N. R. Swerdlow, M. A. Geyer, *J. Pharmacol. Exp. Ther.* 271, 787 (1994).
S. Ball et al., *Biol. Psychiatry* 43, 107 (1998).
C. F. Baxter, R. A. Baldwin, J. L. Davis, J. J. Flood, *Pharmac. Biochem. & Behav.* 22, 1053 (1985).
B. Beatty et al., *Am. J. Hum. Genet.* 59 (Suppl.), A87 (1996).
F. M. Benes, *J. Psychiatr. Res.* 31, 257 (1997).
F. M. Benes, R. Wickramasinghe, S. L. Vincent, Y. Khan, M. Todtenkopf, *Brain Res.* 755, 121 (1997).
R. L. Blake and E. S. Russell, *Science* 176, 809 (1972).
T. D. Blumenthal, *Psychophysiology* 34, 446 (1997). D. Braff et al., *Psychophysiology* 15, 339 (1978).
A. E. Bullock, B. S. Slobe, V. Vasquez, A. C. Collins, *Behav Neurosci.* 111, 1353 (1997).
C. Carlson et al., *Am. J. Hum. Genet.* 61, 620 (1997).
S. Carlson and J. F. Willott, *Hear. Res.* 99, 168 (1996)].
A. Cherkin, M. J. Eckardt, L. K. Gerbrandt, *Science* 193, 242 (1976).
L. Y. Chow et al., *Am. J. Med. Genet.* 74, 677 (1997).S. M. Cohen and J. V. Nadler, *Brain Res.* 769, 333 (1997).
S. M. Cohen and J. V. Nadler, *Brain Res.* 761, 271 (1997).N. Cowan, *Attention and Memory: An Integrated Framework* (Oxford Univ. Press, New York, 1995).
J. Crawley and F. K. Goodwin, *Pharmacol. Biochem. Behav.* 13, 167 (1980).
Cromwell and C. R. Snyder, Eds., (Oxford Univ. Press, New York, 1993), pp. 98–108.
W. E. Crusio, H. Schwegler, J. H. van Abeelen, *Behav. Brain Res.* 32, 80 (1989).
J. L. Davis, R. M. Pico, J. F. Flood, *Behav. Neur. Biol.* 48,128 (1987).
M. Davis, D. S. Gendelman, M. D. Tischler, P. M. Gendelman, *J. Neurosci.* 2, 791 (1982).
D. A. Driscoll et al., *J. Med. Genet.* 30, 813 (1993).
P. Duter and R.A. Nicoll, *Neuron* 1, 585 (1988).
M. Efron, *N. Engl. J. Med.* 272, 1243 (1965).
K. B. J. Franklin and G. Paxinos, *The Mouse Brain in Stereotaxic Coordinates*, Academic Press, New York, 1997.
R. Freedman et al., *Proc. Natl. Acad. Sci. U.S.A.* 94, 587 (1997).

R. Freedman et al., in *Schizophrenia: Origins, processes, treatment, and outcome,* R. L.
R. T. Fremeau Jr. et al., *Mol. Pharmacol.* 49, 1033 (1996).
J. C. Gewirtz and M. Davis, *Behav. Neurosci.* 109, 388 (1995).
M. A. Geyer and D. L. Braff, *Psychophysiology* 19, 1 (1982).
M. A. Geyer and D. L. Braff, *Schizophr. Bull.* 13, 643 (1987).
D. C. Goff and L. Wine, *Schizophr. Res.* 27, 157 (1997).
J. A. Gogos, M. Morgan, V. Luine, M. Santha, S. Ogawa, D. Pfaff, M. Karayiorgou, *Proc. Natl. Acad. Sci. U.S.A.,* 95, 9991–9996 (1998).
P. S. Goldman-Rakic and L. D. Selemon, *Schizophr. Bull.* 23, 437 (1997).
D. Gothelf et al., *Am. J. Med. Genet.* 72, 455 (1997).
D. Grattan and M. Selmanoff, *J. Neurochem.* 60, 2254 (1993).
C. Grillon, R. Ameli, D.S. Charney, *Biol. Psychiatry* 32, 939 (1992).
D. C. Hayward et al., *Proc. Natl. Acad. Sci. U.S.A.* 90, 2979 (1993).
J. Jacken, N. Goemans, J.-P. Fryns, I. Francois, F. de Zegher, *J. Inherit. Metab. Dis.* 19, 275 (1996).
C. Johansson, D. M. Jackson, J. Zhang, L. Svensson, *Pharmacol. Biochem. Behav.* 52, 649 (1995).
J. L. Johnson and E. Roberts, *Brain Res.* 323, 247 (1984).
M. Karayiorgou et al., *Proc. Natl. Acad. Sci. U.S.A.* 92, 7612 (1995).
M. Karayiorgou et al., *Amer. J. Med. Genet.* 74, 677 (1997).
S. F. Kash et al., *Proc. Natl. Acad. Sci. U.S.A.* 94, 14060 (1997).
M. Karayiorgou and J. Gogos, *Neuron* 19, 967 (1997).
M. Koch, C. Kling, C. M. Becker, *Neuroreport* 7, 806, 1996.
M. H. Kodsi and N. R. Swerdlow, *Brain Res. Bull.* 43, 219 (1997).
S. F. Logue, E. H. Owen, D. L. Rasmussen, J. M. Wehner, *Neuroscience* 80, 1075 (1997).
V. N. Luine, D. R. Grattan, M. Selmanoff, *Brain Res.* 747, 165 (1997).
C. Mathis, P. E. Neumann, H. Gershenfeld, S. M. Paul, J. N. Crawley, *Behav. Genet.* 25, 557 (1995).
C. Mathis, S. M. Paul, J. N. Crawley, *Behav. Genet.* 24, 171 (1994).
F. Mollica and L. Provone, *Acta Paediatr. Scand.* 65, 206 (1976).
O. Mors and H. Ewald, *Am. J. Med. Genet.* 74, 677 (1997).
K. C. Murphy and M. J. Owen, *Am. J. Med. Genet.* 74, 660 (1997).
L. Nardos et al., *Cell* 90, 895–905 (1997).
D. F. Papolos, *Am. J. Psychiatry* 153, 1541 (1996).
R. Paylor and J. N. Crawley, *Psychopharmacology* 132, 169 (1997)
O. Paulsen and E. I. Moser, *Trends in Neurosciences* 21, 273 (1998)
T. L. Perry, J. W. Wright, S. Hansen, *Biol. Psychiatry* 18, 89 (1983).
W. Perry and D. L. Braff, *Am. J. Psychiatry* 151, 363–367 (1994)
J. M. Phang, G. C. Yeh, C. R. Scriver, in *The Metabolic and Molecular Bases of Inherited Disease,* C. R. Scriver, A. L. Beaudet, W. S. Sly, D. Valle, Eds. (McGraw-Hill, New York, 1995), pp. 1125–1146.
A. E. Pulver et al., *J. Nerv. Ment. Dis.* 182, 476 (1994).
J. L. Purdy and S. C. Bondy, *Neuroscience* 1, 125 (1976).
N. Risch and K. Merikangas, *Science* 275, 1327 (1997).
T. Rokkones and A. C. Løken, *Acta Paediatr. Scand.* 57, 225 (1968).
J. Salinen, A. Haapalinna, T. Viitamaa, B. K. Kobika, M. Scheinin, *J. Neuroscience* 18, 3035 (1998).
J. Sambrook, E. F. Fritsch, T. Maniatis, *Molecular Cloning: A Laboratory Manual* (Cold Spring Harbor Laboratory Press, Cold Spring Harbor, N.Y., 2nd edition, 1989).
C. R. Scriver and L. E. Rosenberg, *Aminoacid metabolism and its disorders* (Saunders, Philadelphia, 1973).
S. Shafqat et al., *Mol. Pharmacol.* 48, 219 (1995).
Spielman, R. S. et al. Transmission test for linkage disequilibrium: the insulin gene region and insulin-dependent diabetes mellitus (IDDM). *Am. J. Hum. Genet.* (1993), 53:506–516.
K. E. Stevens et al., *Neuropsychopharmacology* 15, 152 (1996). Sulston et al., *Nature* 356, 37 (1992).
N. R. Swerdlow, D. L. Braff, M. A. Geyer, *Brain Res.* 532, 146 (1990).
N. R. Swerdlow, C. H. Benbow, S. Zisook, *Biol. Psychiatry* 33, 298 (1993).
N. R. Swerdlow, D. L. Braff, N. Taaid, M. A. Geyer, *Arch. Gen. Psychiatry* 51, 139 (1994).
C. A. Tumminga, *Crit. Rev. Neurobiol.* 12, 21 (1998).
M. Valez-Faircloth, A. Guadano-Ferraz, V. A. Henzi, R. T. Fremeau Jr., *J. Biol. Chem.* 270, 15755 (1995).
N. Verbruggen, X.-J. Hua, M. May, M. Montagu, *Proc. Natl. Acad. Sci. U.S.A.* 93, 8787 (1996).
S. S. Wang and M. C. Brandriss, *Mol. Cell Biol.* 6, 2638 (1986).
S. S. Wang and M. C. Brandriss, *Mol. Cell Biol.* 7, 4431 (1987).
C. J. Wilson and P. M. Groves, *J. Comp. & Physiol. Psychiatry* 83, 492 (1973).
J. F. Willot, J. Kulig, T. Satterfield, *Hear. Res.* 16, 161 (1984).
T. U. Woo, R. E. Whitehead, D. S. Melchitzky, D. A. Lewis, *Proc. Natl. Acad. Sci. U.S.A.* 95, 5341 (1998).
G. K. Wood et al., *Neuroreport* 9, 461 (1998).W.-L. Yan et al., *Am. J. Med. Genet.* 81, 41 (1998).
Y. Yoneda and E. Roberts, *Brain Res.* 239, 479 (1982).
Y. Yoneda, E. Roberts, G. W. Dietz Jr., *J. Neurochem.* 38, 1686 (1982).

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A method for determining susceptibility in a human subject to schizophrenia wherein the method comprises the steps of:

(a) removing a bodily sample from the subject, wherein the sample comprises a polynucleotide sequence of a PRODH gene;

(b) determining whether the PRODH gene of the bodily sample comprises a DNA sequence comprising a variation in SEQ ID NO:1 consisting of a T to C transition in the first position of codon 497, such that the presence of said variation in said PRODH gene is indicative of said subject's susceptibility to schizophrenia.

* * * * *

SEQUENCE LISTING

<160> NUMBER OF SEQ ID NOS: 9

<210> SEQ ID NO 1
<211> LENGTH: 1551
<212> TYPE: DNA

<213> ORGANISM: Homo sapiens

<400> SEQUENCE: 1

```
atgctggaat tgtgatgag agagtggaaa aaatccagga aacttctagg acagaggcta      60
ttcaacaagc tcatgaagat gaccttctat gggcattttg tagccgggga ggaccaggag    120
tccatccagc ccctgcttcg gcactacagg gccttcggtg tcagcgccat cctggactat    180
ggagtggagg aggacctgag ccccgaggag gcagagcaca aggagatgga gtcctgcacc    240
tcagctgcgg agagggatgg cagtggcacg aataagcggg acaagcaata ccaggcccac    300
cgggccttcg gggaccgcag gaatggtgtc atcagtgccc gcacctactt ctacgccaat    360
gaggccaagt gcgacagcca catggagaca ttcttgcgct gcatcgaagc ctcaggtaga    420
gtcagcgatg acggcttcat agccattaag ctcacagcac tggggagacc ccagtttctg    480
ctgcagttct cagaggtgct ggccaagtgg aggtgcttct tcaccaaat ggctgtggag     540
caagggcagg cgggcctggc tgccatggac accaagctgg aggtggcggt gctgcaggaa    600
agtgtcgcaa agttgggcat cgcatccagg gctgagattg aggactggtt cacggcagag    660
accctgggag tgtctggcac catggacctg ctggactgga gcagcctcat cgacagcagg    720
accaagctgt ccaagcacct ggtagtcccc aacgcacaga caggacagct ggagcccctg    780
ctgtcccggt tcactgagga ggaggagcta cagatgacca ggatgctaca gcggatggat    840
gtcctggcca agaaagccac agagatgggc gtgcggctga tggtggatgc cgagcagacc    900
tacttccagc cggccatcag ccgcctgacg ctggagatga gcggaagtt caatgtggag    960
aagccgctca tcttcaacac ataccagtgc tacctcaagg atgcctatga caatgtgacc   1020
ctggacgtgg agctggctcg ccgtgaggc tggtgttttg gggccaagct ggtgcggggc    1080
gcatacctgg cccaggagcg agcccgtgcg gcagagatcg gctatgagga ccccatcaac   1140
cccacgtacg aggccaccaa cgccatgtac acacaggtgcc tggactacgt gttggaggag   1200
ctgaagcaca cgccaaggc caaggtgatg gtggcctccc acaatgagga cacagtgcgc    1260
ttcgcactgc gcaggatgga ggagctgggc ctgcatcctg ctgaccacca ggtgtacttt   1320
ggacagctgc taggcatgtg tgaccagatc agcttcccgc tgggccaggc cggctacccc   1380
gtgtacaagt acgtgcccta tgccccgtg atggaggtgc tgccctactt gtcccgccgt    1440
gccctggaga acagcagcct catgaagggc acccatcggg agcggcagtt gctgtggctg   1500
gagctcttga ggcggctccg aactggcaac ctcttccatc gccctgccta g            1551
```

<210> SEQ ID NO 2
<211> LENGTH: 516
<212> TYPE: PRT
<213> ORGANISM: Homo sapiens

<400> SEQUENCE: 2

```
Met Leu Glu Phe Val Met Arg Glu Trp Lys Lys Ser Arg Lys Leu Leu
1               5                   10                  15

Gly Gln Arg Leu Phe Asn Lys Leu Met Lys Met Thr Phe Tyr Gly His
            20                  25                  30

Phe Val Ala Gly Glu Asp Gln Glu Ser Ile Gln Pro Leu Leu Arg His
        35                  40                  45

Tyr Arg Ala Phe Gly Val Ser Ala Ile Leu Asp Tyr Gly Val Glu Glu
    50                  55                  60

Asp Leu Ser Pro Glu Glu Ala Glu His Lys Glu Met Glu Ser Cys Thr
65                  70                  75                  80
```

-continued

```
Ser Ala Ala Glu Arg Asp Gly Ser Gly Thr Asn Lys Arg Asp Lys Gln
             85                  90                  95
Tyr Gln Ala His Arg Ala Phe Gly Asp Arg Arg Asn Gly Val Ile Ser
            100                 105                 110
Ala Arg Thr Tyr Phe Tyr Ala Asn Glu Ala Lys Cys Asp Ser His Met
            115                 120                 125
Glu Thr Phe Leu Arg Cys Ile Glu Ala Ser Gly Arg Val Ser Asp Asp
            130                 135                 140
Gly Phe Ile Ala Ile Lys Leu Thr Ala Leu Gly Arg Pro Gln Phe Leu
145                 150                 155                 160
Leu Gln Phe Ser Glu Val Leu Ala Lys Trp Arg Cys Phe Phe His Gln
                165                 170                 175
Met Ala Val Glu Gln Gly Gln Ala Gly Leu Ala Ala Met Asp Thr Lys
                180                 185                 190
Leu Glu Val Ala Val Leu Gln Glu Ser Val Ala Lys Leu Gly Ile Ala
                195                 200                 205
Ser Arg Ala Glu Ile Glu Asp Trp Phe Thr Ala Glu Thr Leu Gly Val
            210                 215                 220
Ser Gly Thr Met Asp Leu Leu Asp Trp Ser Ser Leu Ile Asp Ser Arg
225                 230                 235                 240
Thr Lys Leu Ser Lys His Leu Val Val Pro Asn Ala Gln Thr Gly Gln
                245                 250                 255
Leu Glu Pro Leu Leu Ser Arg Phe Thr Glu Glu Glu Leu Gln Met
                260                 265                 270
Thr Arg Met Leu Gln Arg Met Asp Val Leu Ala Lys Lys Ala Thr Glu
            275                 280                 285
Met Gly Val Arg Leu Met Val Asp Ala Glu Gln Thr Tyr Phe Gln Pro
290                 295                 300
Ala Ile Ser Arg Leu Thr Leu Glu Met Gln Arg Lys Phe Asn Val Glu
305                 310                 315                 320
Lys Pro Leu Ile Phe Asn Thr Tyr Gln Cys Tyr Leu Lys Asp Ala Tyr
                325                 330                 335
Asp Asn Val Thr Leu Asp Val Glu Leu Ala Arg Arg Glu Gly Trp Cys
            340                 345                 350
Phe Gly Ala Lys Leu Val Arg Gly Ala Tyr Leu Ala Gln Glu Arg Ala
            355                 360                 365
Arg Ala Ala Glu Ile Gly Tyr Glu Asp Pro Ile Asn Pro Thr Tyr Glu
370                 375                 380
Ala Thr Asn Ala Met Tyr His Arg Cys Leu Asp Tyr Val Leu Glu Glu
385                 390                 395                 400
Leu Lys His Asn Ala Lys Ala Lys Val Met Val Ala Ser His Asn Glu
                405                 410                 415
Asp Thr Val Arg Phe Ala Leu Arg Arg Met Glu Glu Leu Gly Leu His
            420                 425                 430
Pro Ala Asp His Gln Val Tyr Phe Gly Gln Leu Leu Gly Met Cys Asp
            435                 440                 445
Gln Ile Ser Phe Pro Leu Gly Gln Ala Gly Tyr Pro Val Tyr Lys Tyr
            450                 455                 460
Val Pro Tyr Gly Pro Val Met Glu Val Leu Pro Tyr Leu Ser Arg Arg
465                 470                 475                 480
Ala Leu Glu Asn Ser Ser Leu Met Lys Gly Thr His Arg Glu Arg Gln
                485                 490                 495
Leu Leu Trp Leu Glu Leu Leu Arg Arg Leu Arg Thr Gly Asn Leu Phe
```

-continued

```
                    500             505             510
His Arg Pro Ala
        515

<210> SEQ ID NO 3
<211> LENGTH: 1494
<212> TYPE: DNA
<213> ORGANISM: Mus musculus

<400> SEQUENCE: 3
atgttcgaga gattgatgaa gatgaccttc tatggccatt ttgtggctgg cgaagaccag      60
gagtctatca ggcctctgat ccggcacaac aaagcctttg gtgttggctt tatcctggac    120
tatggagtgg aggaagatct gagccctgag gaggcggagc gcaaagagat ggagtcatgc    180
acttctgaag cagagagaga tggcagtgga gcaaataaga gggagaagca gtatcaggtg    240 cacccccgcct ttggagaccg cagagatggt gtcatcagtg cccgcaccta cttctatgcc    300
aatgaagcca gtgtgacaa ctacatggag aacttactgc agtgcatcaa ggcctcaggt    360
ggagccagtg atggtggttt ctcagccatt aagctcactg cactggggag accacagttt    420
ctgctgcagt tctcagacgt gctgaccagg tggagacggt tcttccatca aatggctgca    480
gagcagggac aggctgggcg tgctgctgta gacacaaagc tggaggtggc ggtgctccag    540
gacagcatcg caaagatggg catcgcatcc agggctgaga ttgaagggtg gttcacgcca    600
gagacgctgg gagtgtctgg caccgtggac ttgctggact ggaacagcct cattgacagc    660
aggacccggc tctccaggca cttggtggtc cccaatgtgc agactggcca gctggagccc    720
ctgctgtcac ggttcactga ggaggaagag cagcagatga aaaggatgct gcagaggatg    780
gatgtactgg ccaagaaagc aaaagaagca ggtgtgcgcc tgatgattga tgctgagcag    840
agctacttcc aaccagccat cagccgcctg accctggaga tgcagcgcag gttcaatgtg    900
gataagccgt tcatcttcaa cacattccag tgctacctca aggatgccta tgacaatgtg    960
accttggata tggaactggc tcgccgtgag ggctggtgtt ccggggccaa gctggtacgt   1020
cgtgcataca tggcccaaga gcgtgtcagg gcagcagaga tcggttatga agaccccatc   1080
aaccctacat atgaagccac caatgctatg taccacaggt gccttaacta tgttctggag   1140
gagctgaagc acagcaccaa ggcagaagtg atggtggctt cccacaacga ggacaccgtg   1200
cacttcackt tgtgcaggat gaaggagata ggcctgcatc ctgctgatgg tcaggtgtgc   1260
ttcggacagc tgctggggat gtgtgaccaa atcagcttcc cactaggcca ggcaggcttt   1320
cctgtgtaca gtatgtgcc ctatggcccct gtgatggagg tactcccttta cctgtcccgc   1380 cgtgccctgg agaacagcag catcatgaag ggtgctcagc gagagaggca gctgctatgg   1440
caggagctcc gcaggcggct gcgcactggc agcctcttcc accatccggc ctag         1494

<210> SEQ ID NO 4
<211> LENGTH: 497
<212> TYPE: PRT
<213> ORGANISM: Mus musculus

<400> SEQUENCE: 4

Met Phe Glu Arg Leu Met Lys Met Thr Phe Tyr Gly His Phe Val Ala
  1               5                  10                  15

Gly Glu Asp Gln Glu Ser Ile Arg Pro Leu Ile Arg His Asn Lys Ala
                 20                  25                  30

Phe Gly Val Gly Phe Ile Leu Asp Tyr Gly Val Glu Glu Asp Leu Ser
             35                  40                  45
```

-continued

```
Pro Glu Glu Ala Glu Arg Lys Glu Met Glu Ser Cys Thr Ser Glu Ala
     50                  55                  60

Glu Arg Asp Gly Ser Gly Ala Asn Lys Arg Glu Lys Gln Tyr Gln Val
 65                  70                  75                  80

His Pro Ala Phe Gly Asp Arg Arg Asp Gly Val Ile Ser Ala Arg Thr
                 85                  90                  95

Tyr Phe Tyr Ala Asn Glu Ala Lys Cys Asp Asn Tyr Met Glu Asn Leu
                100                 105                 110

Leu Gln Cys Ile Lys Ala Ser Gly Gly Ala Ser Asp Gly Gly Phe Ser
            115                 120                 125

Ala Ile Lys Leu Thr Ala Leu Gly Arg Pro Gln Phe Leu Leu Gln Phe
        130                 135                 140

Ser Asp Val Leu Thr Arg Trp Arg Arg Phe Phe His Gln Met Ala Ala
145                 150                 155                 160

Glu Gln Gly Gln Ala Gly Arg Ala Ala Val Asp Thr Lys Leu Glu Val
                165                 170                 175

Ala Val Leu Gln Asp Ser Ile Ala Lys Met Gly Ile Ala Ser Arg Ala
            180                 185                 190

Glu Ile Glu Gly Trp Phe Thr Pro Glu Thr Leu Gly Val Ser Gly Thr
        195                 200                 205

Val Asp Leu Leu Asp Trp Asn Ser Leu Ile Asp Ser Arg Thr Arg Leu
210                 215                 220

Ser Arg His Leu Val Val Pro Asn Val Gln Thr Gly Gln Leu Glu Pro
225                 230                 235                 240

Leu Leu Ser Arg Phe Thr Glu Glu Glu Gln Gln Met Lys Arg Met
                245                 250                 255

Leu Gln Arg Met Asp Val Leu Ala Lys Lys Ala Lys Glu Ala Gly Val
            260                 265                 270

Arg Leu Met Ile Asp Ala Glu Gln Ser Tyr Phe Gln Pro Ala Ile Ser
        275                 280                 285

Arg Leu Thr Leu Glu Met Gln Arg Arg Phe Asn Val Asp Lys Pro Phe
        290                 295                 300

Ile Phe Asn Thr Phe Gln Cys Tyr Leu Lys Asp Ala Tyr Asp Asn Val
305                 310                 315                 320

Thr Leu Asp Met Glu Leu Ala Arg Arg Glu Gly Trp Cys Ser Gly Ala
                325                 330                 335

Lys Leu Val Arg Arg Ala Tyr Met Ala Gln Glu Arg Val Arg Ala Ala
            340                 345                 350

Glu Ile Gly Tyr Glu Asp Pro Ile Asn Pro Thr Tyr Glu Ala Thr Asn
        355                 360                 365

Ala Met Tyr His Arg Cys Leu Asn Tyr Val Leu Glu Glu Leu Lys His
        370                 375                 380

Ser Thr Lys Ala Glu Val Met Val Ala Ser His Asn Glu Asp Thr Val
385                 390                 395                 400

His Phe Thr Leu Cys Arg Met Lys Glu Ile Gly Leu His Pro Ala Asp
                405                 410                 415

Gly Gln Val Cys Phe Gly Gln Leu Leu Gly Met Cys Asp Gln Ile Ser
            420                 425                 430

Phe Pro Leu Gly Gln Ala Gly Phe Pro Val Tyr Lys Tyr Val Pro Tyr
        435                 440                 445

Gly Pro Val Met Glu Val Leu Pro Tyr Leu Ser Arg Arg Ala Leu Glu
    450                 455                 460
```

Asn Ser Ser Ile Met Lys Gly Ala Gln Arg Glu Arg Gln Leu Leu Trp
465                 470                 475                 480

Gln Glu Leu Arg Arg Arg Leu Arg Thr Gly Ser Leu Phe His His Pro
                485                 490                 495

Ala

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:PRIMER

<400> SEQUENCE: 5
gaccaaatca gcttcccact                                                20

<210> SEQ ID NO 6
<211> LENGTH: 20
<212> TYPE: DNA
<213> ORGANISM: PRIMER (ARTIFICIAL)

<400> SEQUENCE: 6
cccttcatga tgctgctgtt                                                20

<210> SEQ ID NO 7
<211> LENGTH: 2240
<212> TYPE: DNA
<213> ORGANISM: Mus musculus

<400> SEQUENCE: 7
agcgcgtctt cttgctgcgg tcggtggcac cacgcgtcgc tgccctctca accaaaccgc      60
aagcccagga acagcctccc gcgagccctg aggctcttcg gggatgtggg gcggccaagg    120
ctgtgcggcc gcctgtgcca gccgtggact tcaccaacac gcaggaggcg tatcgcagcc    180
ggcggagttg ggagttggtg cgcaacctgc tagtgctgcg gctgtgtgcg tcgccggtgc    240
tgctagcgca ccacgagcag ttgttccaag ttgccaggaa gcttctgggg caaaggatgt    300
tcgagagatt gatgaagatg accttctatg ccattttgt ggctggcgaa gaccaggagt    360
ctatcaggcc tctgatccgg cacaacaaag cctttggtgt tggctttatc ctggactatg    420
gagtggagga agatctgagc cctgaggagg cggagcgcaa agagatggag tcatgcactt    480
ctgaagcaga gagagatggc agtggagcaa ataagaggga gaagcagtat caggtgcacc    540
ccgcctttgg agaccgcaga gatggtgtca tcagtgcccg cacctacttc tatgccaatg    600
aagccaagtg tgacaactac atggagaact actgcagtg catcaaggcc tcaggtggag    660
ccagtgatgg tggtttctca gccattaagc tcactgcact ggggagacca cagtttctgc    720
tgcagttctc agacgtgctg accaggtgga cggttctt ccatcaaatg gctgcagagc    780
agggacaggc tgggcgtgct gctgtagaca caaagctgga ggtggcggtg ctccaggaca    840
gcatcgcaaa gatgggcatc gcatccaggg ctgagattga agggtggttc acgccagaga    900
cgctgggagt gtctggcacc gtggacttgc tggactggaa cagcctcatt gacagcagga    960
cccggctctc caggcacttg gtggtcccca atgtgcagac tggccagctg gagcccctgc   1020
tgtcacggtt cactgaggag gaagagcagc agatgaaaag gatgctgcag aggatggatg   1080
tactggccaa gaaagcaaaa gaagcaggtg tgcgcctgat gattgatgct gagcagagct   1140
acttccaacc agccatcagc cgcctgaccc tggagatgca gcgcaggttc aatgtggata   1200
agccgttcat cttcaacaca ttccagtgct acctcaagga tgcctatgac aatgtgacct   1260

-continued

```
tggatatgga actggctcgc cgtgagggct ggtgttccgg ggccaagctg gtacgtcgtg    1320
catacatggc ccaagagcgt gtcagggcag cagagatcgg ttatgaagac cccatcaacc    1380
ctacatatga agccaccaat gctatgtacc acaggtgcct taactatgtt ctggaggagc    1440
tgaagcacag caccaaggca gaagtgatgg tggcttccca caacgaggac accgtgcact    1500
tcackttgtg caggatgaag gagataggcc tgcatcctgc tgatggtcag gtgtgcttcg    1560
gacagctgct ggggatgtgt gaccaaatca gcttcccact aggccaggca ggctttcctg    1620
tgtacaagta tgtgccctat ggccctgtga tgtaggtact cccttacctg tcccgccgtg    1680
ccctggagaa cagcagcatc atgaagggtg ctcagcgaga gaggcagctg ctatggcagg    1740
agctccgcag gcggctgcgc actggcagcc tcttccacca tccggcctag tcaccgcagg    1800
agccttgccc acccgctcgt actccactca accccttacc tctgggcttt caggcggggc    1860
acagcttggg attgggctgg ggttccttaa cccaacctgc ccagacacag ttcacctttt    1920
tatgcccaag gctttttatg cccaaggcgg gatttcatca gtggacagtt cctgaggaac    1980
agtgcccaag atggtcgtct ggtcacagag gctgccttct gggacttcct gtaccccaag    2040
gaacagacac tcaggagtgg ggtcagttag agcccctggg agctgcccca ctaatttgag    2100
taagcactga ccacttctgc aggttacaga gccctagtcc aggattaacc ttctgccagg    2160
gtctaaccca ttttccctgc actgggcaga ggacagacta ggaagcctgt ttagtcaata    2220
aatcatcctg taacagagtc                                                 2240
```

<210> SEQ ID NO 8
<211> LENGTH: 452
<212> TYPE: PRT
<213> ORGANISM: Mus musculus

<400> SEQUENCE: 8

```
Met Phe Glu Arg Leu Met Lys Met Thr Phe Tyr Gly His Phe Val Ala
  1               5                  10                  15

Gly Glu Asp Gln Glu Ser Ile Arg Pro Leu Ile Arg His Asn Lys Ala
             20                  25                  30

Phe Gly Val Gly Phe Ile Leu Asp Tyr Gly Val Glu Glu Asp Leu Ser
         35                  40                  45

Pro Glu Glu Ala Glu Arg Lys Glu Met Glu Ser Cys Thr Ser Glu Ala
     50                  55                  60

Glu Arg Asp Gly Ser Gly Ala Asn Lys Arg Glu Lys Gln Tyr Gln Val
 65                  70                  75                  80

His Pro Ala Phe Gly Asp Arg Arg Asp Gly Val Ile Ser Ala Arg Thr
                 85                  90                  95

Tyr Phe Tyr Ala Asn Glu Ala Lys Cys Asp Asn Tyr Met Glu Asn Leu
            100                 105                 110

Leu Gln Cys Ile Lys Ala Ser Gly Ala Ser Asp Gly Gly Phe Ser
        115                 120                 125

Ala Ile Lys Leu Thr Ala Leu Gly Arg Pro Gln Phe Leu Leu Gln Phe
    130                 135                 140

Ser Asp Val Leu Thr Arg Trp Arg Arg Phe Phe His Gln Met Ala Ala
145                 150                 155                 160

Glu Gln Gly Gln Ala Gly Arg Ala Ala Val Asp Thr Lys Leu Glu Val
                165                 170                 175

Ala Val Leu Gln Asp Ser Ile Ala Lys Met Gly Ile Ala Ser Arg Ala
            180                 185                 190
```

```
Glu Ile Glu Gly Trp Phe Thr Pro Glu Thr Leu Gly Val Ser Gly Thr
            195                 200                 205

Val Asp Leu Leu Asp Trp Asn Ser Leu Ile Asp Ser Arg Thr Arg Leu
210                 215                 220

Ser Arg His Leu Val Val Pro Asn Val Gln Thr Gly Gln Leu Glu Pro
225                 230                 235                 240

Leu Leu Ser Arg Phe Thr Glu Glu Glu Gln Gln Met Lys Arg Met
                245                 250                 255

Leu Gln Arg Met Asp Val Leu Ala Lys Lys Ala Lys Glu Ala Gly Val
            260                 265                 270

Arg Leu Met Ile Asp Ala Glu Gln Ser Tyr Phe Gln Pro Ala Ile Ser
            275                 280                 285

Arg Leu Thr Leu Glu Met Gln Arg Arg Phe Asn Val Asp Lys Pro Phe
            290                 295                 300

Ile Phe Asn Thr Phe Gln Cys Tyr Leu Lys Asp Ala Tyr Asp Asn Val
305                 310                 315                 320

Thr Leu Asp Met Glu Leu Ala Arg Arg Glu Gly Trp Cys Ser Gly Ala
                325                 330                 335

Lys Leu Val Arg Arg Ala Tyr Met Ala Gln Glu Arg Val Arg Ala Ala
                340                 345                 350

Glu Ile Gly Tyr Glu Asp Pro Ile Asn Pro Thr Tyr Glu Ala Thr Asn
            355                 360                 365

Ala Met Tyr His Arg Cys Leu Asn Tyr Val Leu Glu Glu Leu Lys His
            370                 375                 380

Ser Thr Lys Ala Glu Val Met Val Ala Ser His Asn Glu Asp Thr Val
385                 390                 395                 400

His Phe Thr Leu Cys Arg Met Lys Glu Ile Gly Leu His Pro Ala Asp
                405                 410                 415

Gly Gln Val Cys Phe Gly Gln Leu Leu Gly Met Cys Asp Gln Ile Ser
                420                 425                 430

Phe Pro Leu Gly Gln Ala Gly Phe Pro Val Tyr Lys Tyr Val Pro Tyr
            435                 440                 445

Gly Pro Val Met
            450

<210> SEQ ID NO 9
<211> LENGTH: 2389
<212> TYPE: DNA
<213> ORGANISM: Homo sapiens

<400> SEQUENCE: 9
taatgagagg gaaacaagt atgaagctgt gtggctgaaa ccgtcttggc aagttaggga      60
aagaaaacgg aagtcactgg ggctgatcac agtgctaagc atgagagcac tgcaagatga     120
ggtcacggag gtgggcaggg accggcttgt gccaggcctt gctggcaggg tgaagagttt    180
gccttttctc tgcgtacaat ggaaaggaga agaggtttta agcaagagaa tggcttggtc    240
atgtgtatgt cttgagaca ccctggctag tctatgtatg atgcaaaagg tgggtggggc     300
agggtgacaa gaaatactg ttccggagct tcctgtggct gtgcctataa gaggtggtgg     360
tggtggtgtg gaaggaggtg tggcagtgaa taaacagaga tgtagaaaca gcgtgtacat    420
atattttaag gaacactgag gacgtgatgc tggaatttgt gatgagagag tggaaaaaat    480
ccaggaaact tctaggacag aggctattca acaagctcat gaagatgacc ttctatgggc    540
attttgtagc cggggaggac caggagtcca tccagcccct gcttcggcac tacagggcct    600
```

-continued

| | |
|---|---|
| tcggtgtcag cgccatcctg gactatggag tggaggagga cctgagcccc gaggaggcag | 660 |
| agcacaagga gatggagtcc tgcacctcag ctgcggagag ggatggcagt ggcacgaata | 720 |
| agcgggacaa gcaataccag gcccaccggg ccttcgggga ccgcaggaat ggtgtcatca | 780 |
| gtgcccgcac ctacttctac gccaatgagg ccaagtgcga cagccacatg gagacattct | 840 |
| tgcgctgcat cgaagcctca ggtagagtca gcgatgacgg cttcatagcc attaagctca | 900 |
| cagcactggg gagacccag tttctgctgc agttctcaga ggtgctggcc aagtggaggt | 960 |
| gcttctttca ccaaatggct gtggagcaag ggcaggcggg cctggctgcc atggacacca | 1020 |
| agctggaggt ggcggtgctg caggaaagtg tcgcaaagtt gggcatcgca tccagggctg | 1080 |
| agattgagga ctggttcacg gcagagaccc tgggagtgtc tggcaccatg gacctgctgg | 1140 |
| actggagcag cctcatcgac agcaggacca agctgtccaa gcacctggta gtccccaacg | 1200 |
| cacagacagg acagctggag cccctgctgt cccggttcac tgaggaggag gagctacaga | 1260 |
| tgaccaggat gctacagcgg atggatgtcc tggccaagaa agccacagag atgggcgtgc | 1320 |
| ggctgatggt ggatgccgag cagacctact tccagccggc catcagccgc ctgacgctgg | 1380 |
| agatgcagcg gaagttcaat gtggagaagc cgctcatctt caacacatac cagtgctacc | 1440 |
| tcaaggatgc ctatgacaat gtgaccctgg acgtggagct ggctcgccgt gagggctggt | 1500 |
| gttttggggc caagctggtg cggggcgcat acctggccca ggagcgagcc cgtgcggcag | 1560 |
| agatcggcta tgaggacccc atcaacccca cgtacgaggc caccaacgcc atgtaccaca | 1620 |
| ggtgcctgga ctacgtgttg gaggagctga agcacaacgc caaggccaag gtgatggtgg | 1680 |
| cctcccacaa tgaggacaca gtgcgcttcg cactgcgcag gatggaggag ctgggcctgc | 1740 |
| atcctgctga ccaccaggtg tactttggac agctgctagg catgtgtgac cagatcagct | 1800 |
| tcccgctggg ccaggccggc taccccgtgt acaagtacgt gccctatggc cccgtgatgg | 1860 |
| aggtgctgcc ctacttgtcc cgccgtgccc tggagaacag cagcctcatg aagggcaccc | 1920 |
| atcgggagcg gcagttgctg tggctggagc tcttgaggcg gctccgaact ggcaacctct | 1980 |
| tccatcgccc tgcctagcac ccgccagcac accctcagcc tccagcaccc ccgcccccg | 2040 |
| cccaggccat caccacagct gcagccaacc ccatcctcac acagattcac cttttttcac | 2100 |
| cccacacttg cagagctgct ggaggtgagg tcaggtgcct cccagccctg cccagagtat | 2160 |
| gggcactcag gtgtgggccg aacctgatac ctgcctggga cagccactgg aaacttttgg | 2220 |
| gaactctcct cgaatgtgtg gcccaaggcc cccacctctg tgaccccat gtccttggac | 2280 |
| ctagaggatt gtccaccttc tgccaaggcc agcccacaca gcccgagccc cttggggagc | 2340 |
| agtggccggg ctggggaggc ctgcctggtc aataaaccac tgttcctgc | 2389 |